US012023170B2

(12) United States Patent
Rogers et al.

(10) Patent No.: US 12,023,170 B2
(45) Date of Patent: Jul. 2, 2024

(54) SYSTEMS AND METHODS FOR WIRELESS, REAL-TIME MONITORING PARAMETERS OF SWEAT AND APPLICATIONS OF SAME

(71) Applicant: NORTHWESTERN UNIVERSITY, Evanston, IL (US)

(72) Inventors: John A. Rogers, Wilmette, IL (US); Roozbeh Ghaffari, Cambridge, MA (US); Kyeongha Kwon, Evanston, IL (US); Jong Uk Kim, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 32 days.

(21) Appl. No.: 18/014,362

(22) PCT Filed: Jul. 8, 2021

(86) PCT No.: PCT/US2021/040847
§ 371 (c)(1),
(2) Date: Jan. 4, 2023

(87) PCT Pub. No.: WO2022/011118
PCT Pub. Date: Jan. 13, 2022

(65) Prior Publication Data
US 2023/0270372 A1    Aug. 31, 2023

Related U.S. Application Data
(60) Provisional application No. 63/049,245, filed on Jul. 8, 2020.

(51) Int. Cl.
*A61B 5/00* (2006.01)
*A61B 5/01* (2006.01)
(Continued)

(52) U.S. Cl.
CPC ............ *A61B 5/4266* (2013.01); *A61B 5/002* (2013.01); *A61B 5/01* (2013.01); *A61B 5/6833* (2013.01);
(Continued)

(58) Field of Classification Search
CPC ......... A61B 5/4266; A61B 5/002; A61B 5/01; A61B 5/6833; A61B 5/7225;
(Continued)

(56) References Cited

U.S. PATENT DOCUMENTS

2017/0231571 A1    8/2017  Rogers et al.
2017/0325724 A1*  11/2017  Wang ................. A61B 5/14532
(Continued)

FOREIGN PATENT DOCUMENTS

WO    2017070640 A1    4/2017
WO    2018223033 A1   12/2018
WO    2019126188 A1    6/2019

OTHER PUBLICATIONS

Korean Intellectual Property Office (ISR/KR), "International Search Report for PCT/US2021/040847", Korea, Nov. 4, 2021.
(Continued)

*Primary Examiner* — Michael J Brown
(74) *Attorney, Agent, or Firm* — Locke Lord LLP; Tim Tingkang Xia, Esq.

(57) ABSTRACT

This invention discloses a sensor for measuring parameters of sweat from a skin, comprising a flexible structure comprising a fluid passage having inlet and outlet, the flexible structure being detachably attached to the skin and configured such that sweat enters the inlet as the sweat releases from the skin and flows through the fluid passage into the outlet; a thermal actuator disposed on the flexible structure over the fluid passage and configured to operably provide heat to flow of the sweat through the fluid passage; a first
(Continued)

thermistor disposed on the flexible structure over the fluid passage between the inlet and the thermal actuator and configured to operably measure a first temperature of the sweat thereon; and a second thermistor disposed on the flexible structure over the fluid passage between the thermal actuator and the outlet and configured to operably measure a second temperature of the sweat thereon.

54 Claims, 35 Drawing Sheets

(51) Int. Cl.
　　　*F24F 11/63*　　　(2018.01)
　　　*G05B 19/042*　　　(2006.01)
(52) U.S. Cl.
　　　CPC ............ *A61B 5/7225* (2013.01); *F24F 11/63* (2018.01); *G05B 19/042* (2013.01); *A61B 2562/0271* (2013.01); *A61B 2562/164* (2013.01); *G05B 2219/2614* (2013.01)
(58) Field of Classification Search
　　　CPC ...... A61B 2562/0271; A61B 2562/164; A61B 10/0064; A61B 5/14521; A61B 5/14532; A61B 5/14539; A61B 5/1455; A61B 5/4875; A61B 2503/10; A61B 2505/09; A61B 2562/12; F24F 11/63; G05B 19/042; G05B 2219/2614
　　　USPC .......................................................... 700/276
　　　See application file for complete search history.

(56) References Cited

U.S. PATENT DOCUMENTS

| | | | | |
|---|---|---|---|---|
| 2018/0020966 | A1* | 1/2018 | Begtrup | A61B 5/01 600/301 |
| 2018/0318543 | A1* | 11/2018 | Coleman | A61M 16/0463 |
| 2019/0008448 | A1* | 1/2019 | Begtrup | G01N 33/48792 |
| 2019/0183398 | A1 | 6/2019 | Heikenfeld et al. | |
| 2021/0190372 | A1* | 6/2021 | Montanez | F24H 15/215 |
| 2022/0175280 | A1* | 6/2022 | Pelssers | A61B 5/4266 |

OTHER PUBLICATIONS

Baker, L. B. Sweating rate and sweat sodium concentration in athletes: a review of methodology and intra/interindividual variability. Sports Med. 47, 111-128 (2017).
Gambhir, S. S., Ge, T. J., Vermesh, O. & Spitler, R. Toward achieving precision health. Sci. Transl. Med. 10, eaao3612 (2018).
Bariya, M., Nyein, H. Y. Y. & Javey, A. Wearable sweat sensors. Nat. Electron. 1, 160-171 (2018).
Sonner, Z. et al. The microfluidics of the eccrine sweat gland, including biomarker partitioning, transport and biosensing implications. Biomicrofluidics 9, 031301 (2015).
Gao, W. et al. Fully integrated wearable sensor arrays for multiplexed in situ perspiration analysis. Nature 529, 509-514 (2016).
Reeder, J. T. et al. Waterproof, electronics-enabled, epidermal microfluidic devices for sweat collection, biomarker analysis and thermography in aquatic settings. Sci. Adv. 5, eaau6356 (2019).
Bandodkar, A. J. et al. Battery-free, skin-interfaced microfluidic/ electronic systems for simultaneous electrochemical, colorimetric and volumetric analysis of sweat. Sci. Adv. 5, eaav3294 (2019).
Baker, L. B., Stofan, J. R., Hamilton, A. A. & Horswill, C. A. Comparison of regional patch collection vs. whole body washdown for measuring sweat sodium and potassium loss during exercise. J. Appl. Physiol. 107, 887-895 (2009).
Maughan, R. J. et al. Water balance and salt losses in competitive football. Int. J. Sport Nutr. Exerc. Metab. 17, 583-594 (2007).
Williams, C. A. & Blackwell, J. Hydration status, fluid intake and electrolyte losses in youth soccer players. Int. J. Sports Physiol. Perform. 7, 367-374 (2012).
Al-Omari, M. et al. A portable optical human sweat sensor. J. Appl. Phys. 116, 183102 (2014).
Bandodkar, A. J. & Wang, J. Non-invasive wearable electrochemical sensors: a review. Trends Biotechnol. 32, 363-371 (2014).
Dam, V. A. T., Zevenbergen, M. A. G. & van Schaijk, R. Toward wearable patch for sweat analysis. Sens. Actuators B Chem. 236, 834-838 (2016).
Bain, A. R., Deren, T. M. & Jay, O. Describing individual variation in local sweating during exercise in a temperate environment. Eur. J. Appl. Physiol. 111, 1599-1607 (2011).
Patterson, M. J., Galloway, S. D. R. & Nimmo, M. A. Variations in regional sweat composition in normal human males. Exp. Physiol. 85, 869-875 (2000).
Matzeu, G., Fay, C., Vaillant, A., Coyle, S. & Diamond, D. A wearable device for monitoring sweat rates via image analysis. IEEE Trans. Biomed. Eng. 63, 1672-1680 (2016).
Choi, J., Ghaffari, R., Baker, L. B. & Rogers, J. A. Skin-interfaced systems for sweat collection and analytics. Sci. Adv. 4, eaar3921 (2018).
Francis, J., Stamper, I., Heikenfeld, J. & Gomez, E. F. Digital nanoliter to milliliter flow rate sensor with in vivo demonstration for continuous sweat rate measurement. Lab Chip 19, 178-185 (2019).
Iftekhar, A. T., Ho, J. C.-T., Mellinger, A. & Kaya, T. 3D modeling and characterization of a calorimetric flow rate sensor for sweat rate sensing applications. J. Appl. Phys. 121, 094505 (2017).
Brueck, A., Iftekhar, T., Stannard, B. A., Yelamarthi, K. & Kaya, T. A real-time wireless sweat rate measurement system for physical activity monitoring. Sensors 18, 533 (2018).
Farrell, P. M. et al. Guidelines for diagnosis of cystic fibrosis in newborns through older adults: Cystic Fibrosis Foundation consensus report. J. Pediatr. 153, S4-S14 (2008).
Moyer, J., Wilson, D., Finkelshtein, I., Wong, B. & Potts, R. Correlation between sweat glucose and blood glucose in subjects with diabetes. Diabetes Technol. Ther. 14, 398-402 (2012).
Robinson, S. & Robinson, A. H. Chemical composition of sweat. Physiol. Rev. 34, 202-220 (1954).
Bass, D. E. & Dobalian, I. T. Ratio between true and apparent creatinine in sweat. J. Appl. Physiol. 5, 555-558 (1953).
Al-Tamer, Y. Y., Hadi, E. A. & Al-Badrani, I. E. I. Sweat urea, uric acid and creatinine concentrations in uraemic patients. Urol. Res. 25, 337-340 (1997).
Harvey, C. J., LeBouf, R. F. & Stefaniak, A. B. Formulation and stability of a novel artificial human sweat under conditions of storage and use. Toxicol. In Vitro 24, 1790-1796 (2010).
Huang, C.-T., Chen, M.-L., Huang, L.-L. & Mao, I.-F. Uric acid and urea in human sweat. Chin. J. Physiol. 45, 109-115 (2002).
Patterson, M. J., Galloway, S. D. R. & Nimmo, M. A. Effect of induced metabolic alkalosis on sweat composition in men. Acta Physiol. Scand. 174, 41-46 (2002).
Choi, J. et al. Soft, skin-integrated multifunctional microfluidic systems for accurate colorimetric analysis of sweat biomarkers and temperature. ACS Sens. 4, 379-388 (2019).
Zhang, Y. et al. Passive sweat collection and colorimetric analysis of biomarkers relevant to kidney disorders using a soft microfluidic system. Lab Chip 19, 1545-1555 (2019).
Emrich, H. M. et al. Sweat composition in relation to rate of sweating in patients with cystic fibrosis of the pancreas. Pediatr. Res. 2, 464-478 (1968).
Ohara, K. Chloride concentration in sweat; its individual, regional, seasonal and some other variations, and interrelations between them. Jpn J. Physiol 16, 274-290 (1966).
Coyle, S. et al. Textile sensors to measure sweat pH and sweat-rate during exercise. In Proc. 3rd International ICST Conference on Pervasive Computing Technologies for Healthcare 1-6, https://doi. org/10.4108/ICST.PERVASIVEHEALTH2009.5957 (ICST, 2009).
Oncescu, V., O'Dell, D. & Erickson, D. Smartphone based health accessory for colorimetric detection of biomarkers in sweat and saliva. Lab Chip 13, 3232-3238 (2013).

(56) References Cited

OTHER PUBLICATIONS

Torrente-Rodriguez, R. M. et al. Investigation of cortisol dynamics in human sweat using a graphene-based wireless mHealth system. Matter 2, 921-937 (2020).
Marriott, B. M. Food Components to Enhance Performance: An Evaluation of Potential Performance-Enhancing Food Components for Operational Rations (National Academic Press, 1994).
Robson, P. J. et al. Effects of exercise intensity, duration and recovery on in vitro neutrophil function in male athletes. Int. J. Sports Med. 20, 128-135 (1999).
Luger, A. et al. Acute hypothalamic-pituitary-adrenal responses to the stress of treadmill exercise. New Engl. J. Med. 316, 1309-1315 (1987).
Koc, S. The acute effect of aerobic exercise on serum cortisol levels of athletes and sedentary individuals. J. Educ. Train. Stud. 6, 29-36 (2018).
Hong, Y. J. et al. Multifunctional wearable system that integrates sweat-based sensing and vital-sign monitoring to estimate pre-/post-exercise glucose levels. Adv. Funct. Mater. 28, 1805754 (2018).
Emaminejad, S. et al. Autonomous sweat extraction and analysis applied to cystic fibrosis and glucose monitoring using a fully integrated wearable platform. Proc. Natl Acad. Sci. USA 114, 4625-4630 (2017).
Sessler, D. I. Temperature monitoring and perioperative thermoregulation. Anesthesiology 109, 318-338 (2008).
Zhang, Y. et al. Battery-free, fully implantable optofluidic cuff system for wireless optogenetic and pharmacological neuromodulation of peripheral nerves. Sci. Adv. 5, eaaw5296 (2019).
Yeung, C. et al. A 3D-printed microfluidic-enabled hollow microneedle architecture for transdermal drug delivery. Biomicrofluidics 13, 064125 (2019).
Lopez-Ramirez, M. A. et al. Built-in active microneedle patch with enhanced autonomous drug delivery. Adv. Mater. 32, 1905740 (2020).
Webb, R. C. et al. Epidermal devices for noninvasive, precise and continuous mapping of macrovascular and microvascular blood flow. Sci. Adv. 1, e1500701 (2015).
Ma, Y. et al. Relation between blood pressure and pulse wave velocity for human arteries. Proc. Natl Acad. Sci. USA 115, 11144-11149 (2018).
Cho, H., Kim, H.-Y., Kang, J. Y. & Kim, T. S. How the capillary burst microvalve works. J. Colloid Interface Sci. 306, 379-385 (2007).
Choi, J. et al. Soft, skin-mounted microfluidic systems for measuring secretory fluidic pressures generated at the surface of the skin by eccrine sweat glands. Lab Chip 17, 2572-2580 (2018).
Liu, G. et al. A wearable conductivity sensor for wireless real-time sweat monitoring. Sensors Actuators B Chem. 227, 35-42 (2015).

\* cited by examiner

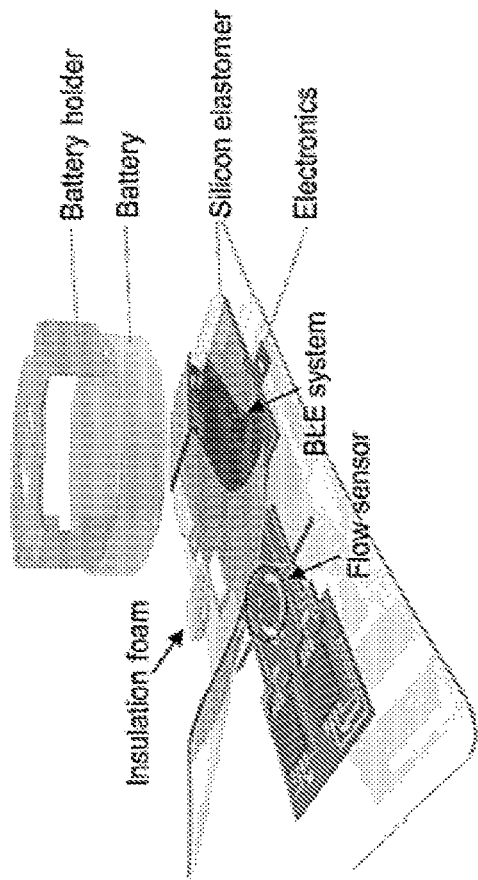
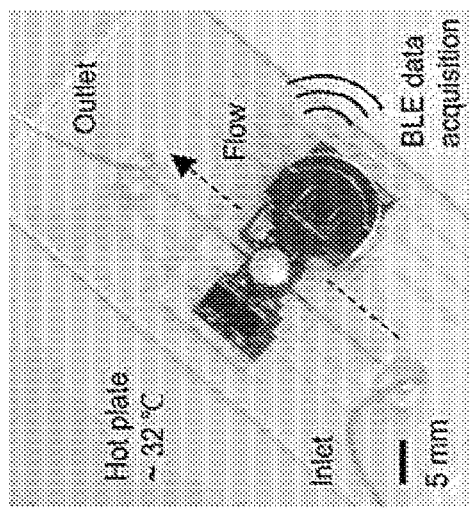
FIG. 6B
FIG. 6A

FIG. 10A
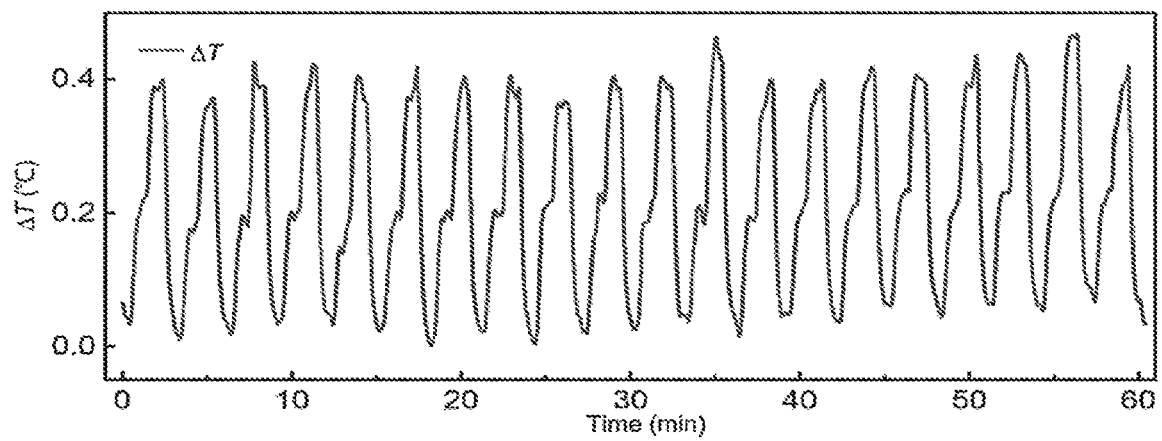
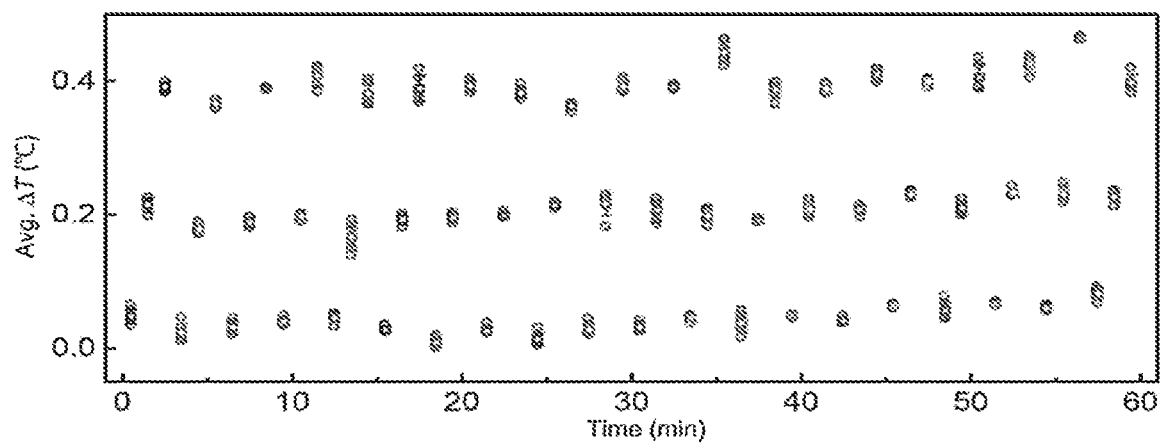
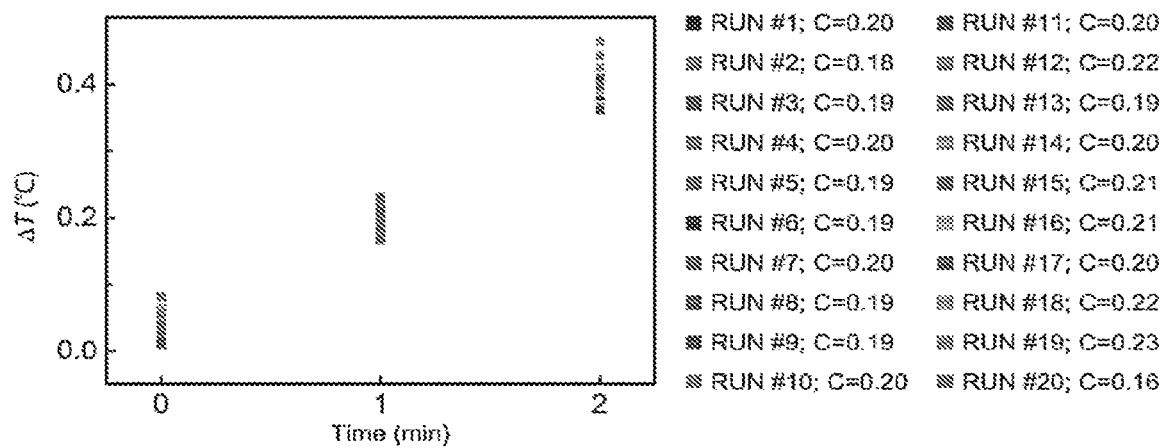
FIG. 10B

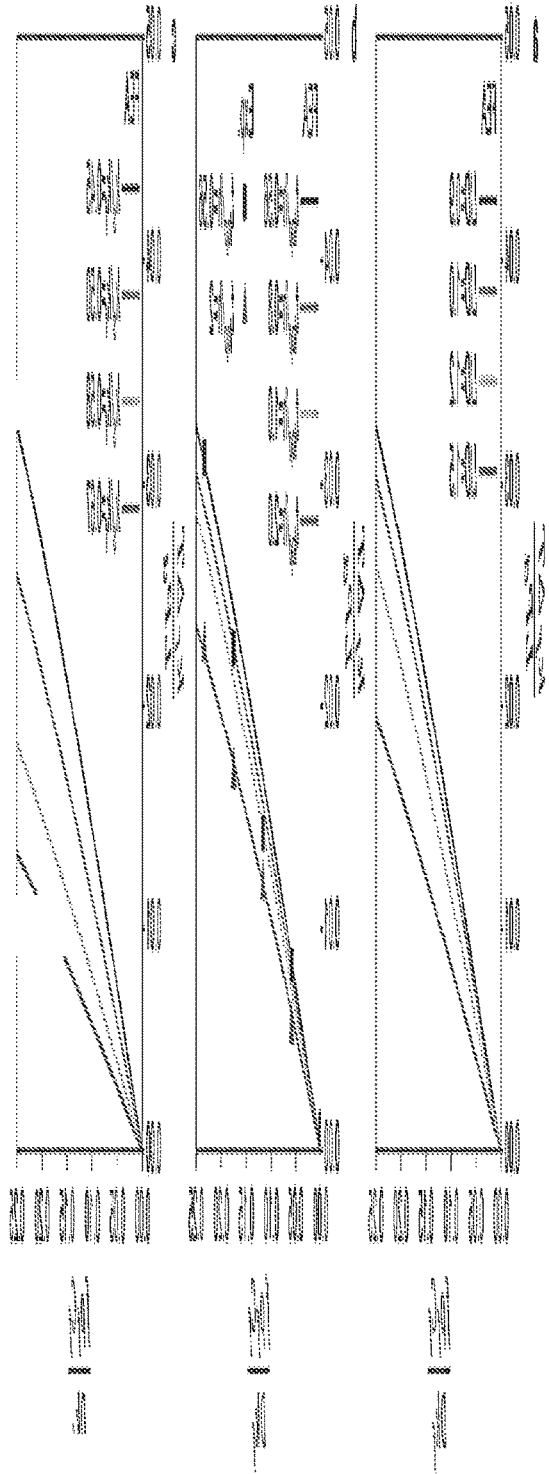
FIG. 14A
FIG. 14B
FIG. 14C
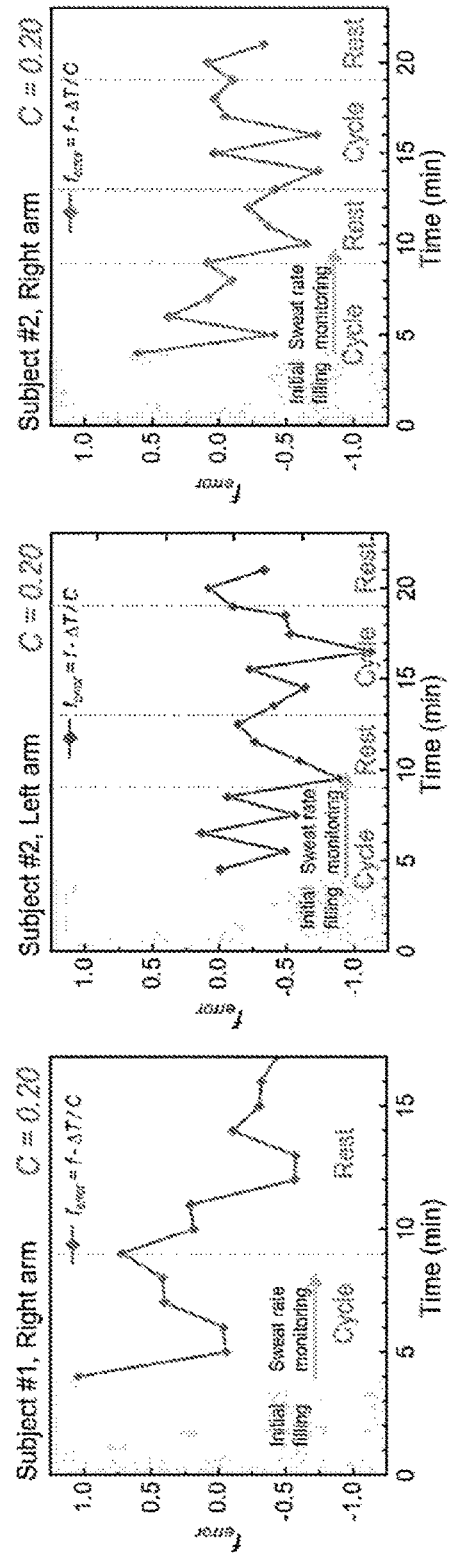
FIG. 15A
FIG. 15B
FIG. 15C

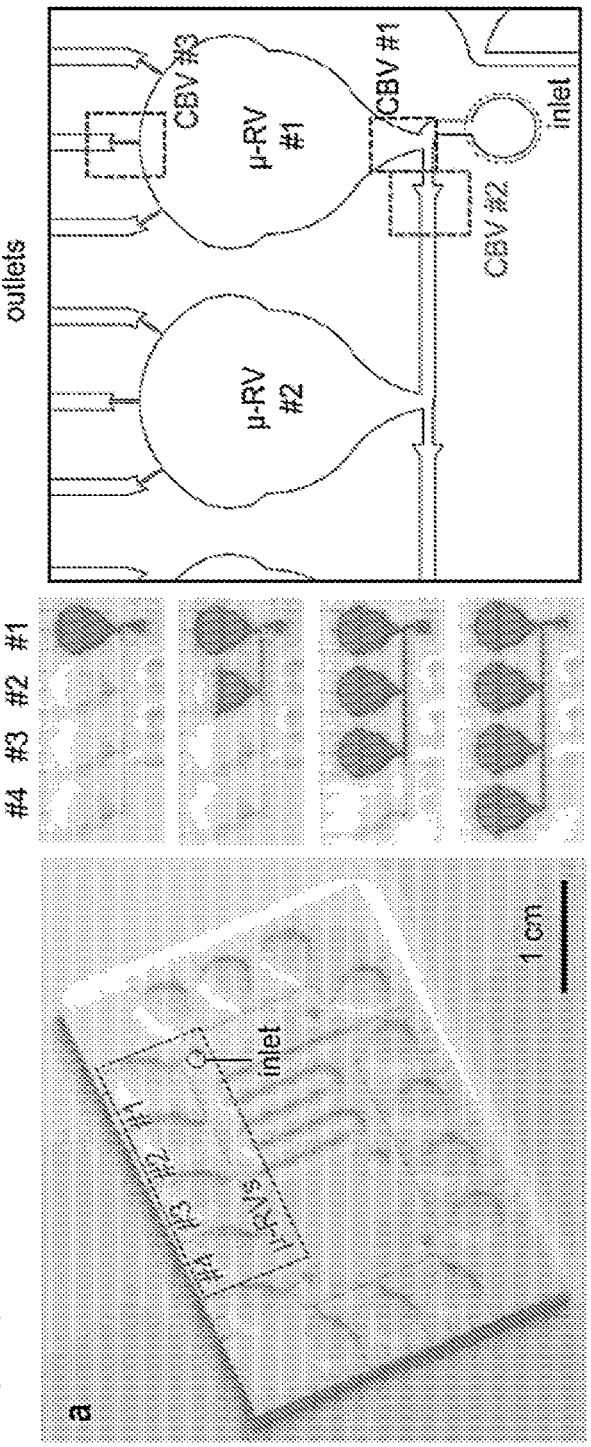
FIG. 16A
FIG. 16B
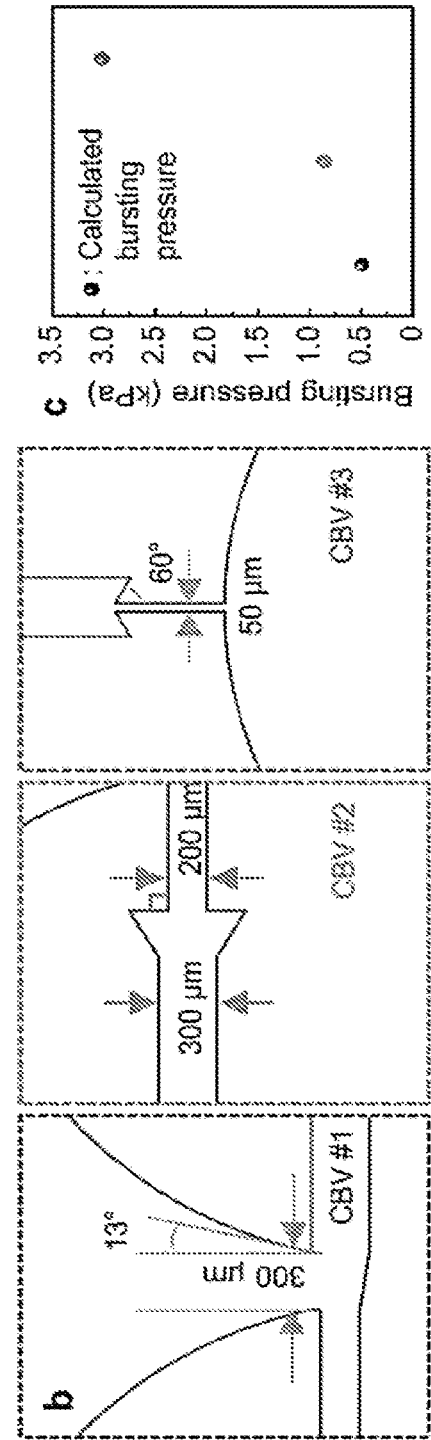
FIG. 16C

FIG. 17A
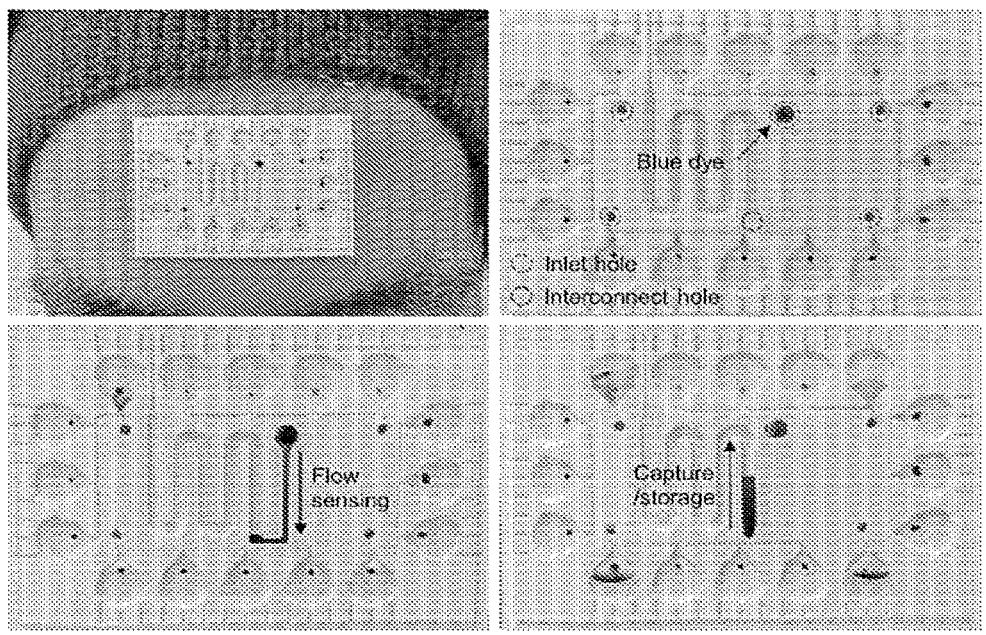
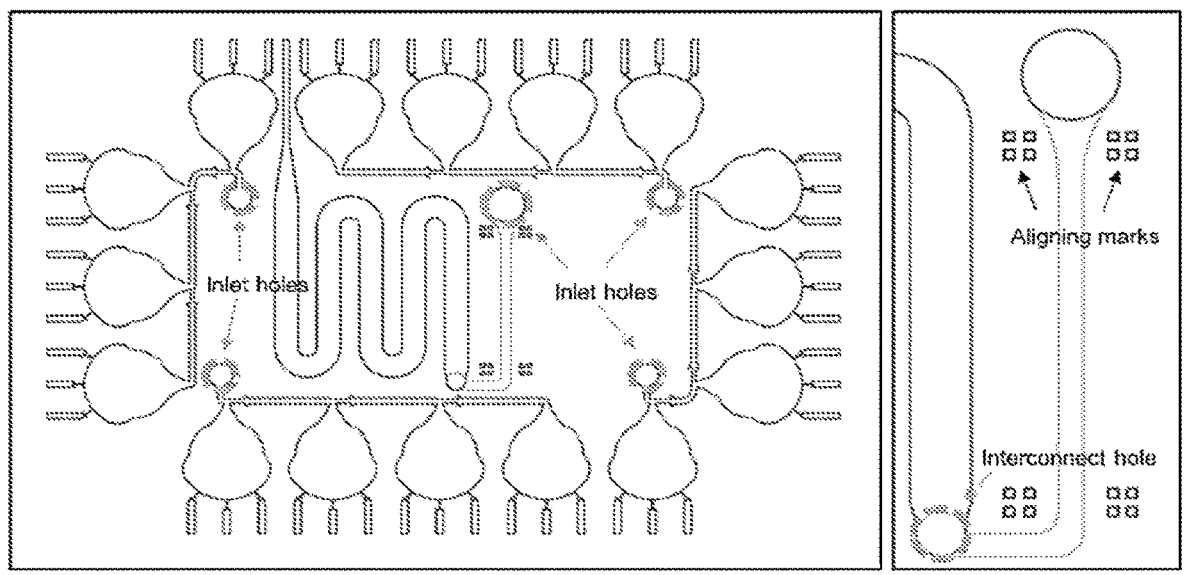
FIG. 17B

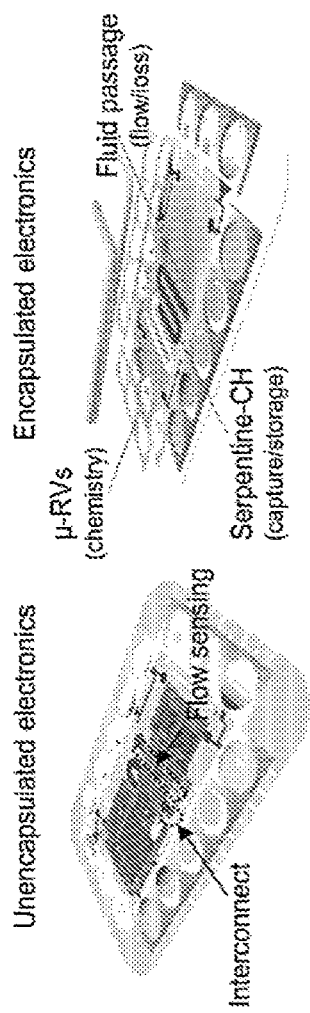
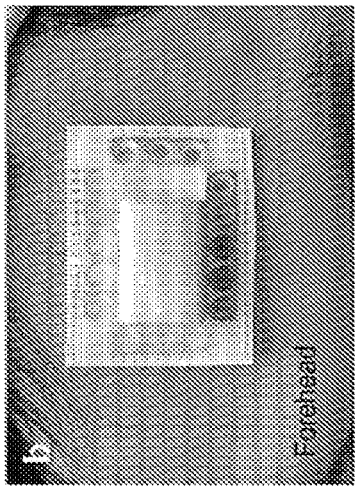
FIG. 18A
FIG. 18B

SYSTEMS AND METHODS FOR WIRELESS, REAL-TIME MONITORING PARAMETERS OF SWEAT AND APPLICATIONS OF SAME

CROSS-REFERENCE TO RELATED PATENT APPLICATION

This application claims priority to and the benefit of U.S. Provisional Patent Application No. 63/049,245, filed Jul. 8, 2020, which is incorporated herein in its entirety by reference.

STATEMENT AS TO RIGHTS UNDER FEDERALLY-SPONSORED RESEARCH

This invention was made with government support under DMR-1720139 awarded by the National Science Foundation. The government has certain rights in the invention.

FIELD OF THE INVENTION

The present invention relates generally to healthcare, and more particularly to systems and methods for wireless, real-time monitoring of the flow rate, cumulative loss and temperature of sweat and applications of the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Sweat rate is an important health marker that provides information about hydration state, stress and physical exertion. The resulting insights can be used to develop optimized strategies for fluid intake. Sweat rates are typically measured using the whole-body wash method, which requires strictly controlled laboratory conditions. Alternatively, absorbent pads can yield regional sweat rates, but they also require laboratory-based analysis and do not provide real-time information. Skin-interfaced device platforms have recently been developed that exploit optical and/or electrochemical methods and can monitor sweat loss and sweat chemistry by means of individualized, real-time measurements. Microfluidic systems that use lab-on-a-chip technologies and colour-responsive chemistries are particularly powerful because of their ability to provide visual readout of a range of key information related to sweat. Nevertheless, for certain applications (including worker safety, military training and contact sports), protective equipment limits visual inspection of such devices.

Emerging techniques, such as wearable conductivity sensors, enable real-time monitoring of sweat rate, but they rely on contact of the electrodes with sweat, which can be affected by salt build-up in the chamber, contamination and corrosion, as well as other detrimental phenomena. Systems that use calorimetric sensing for determining sweat rates have also been developed, but they also require direct electrical interfaces to the sweat, as well as high levels of power consumption (~80 mA at 5 V and 3.3 V). Such approaches demand careful cleaning and sterilization between cycles of use, and they require large batteries, which limits their re-use and comfort.

Therefore, a heretofore unaddressed need exists in the art to address the aforementioned deficiencies and inadequacies.

SUMMARY OF THE INVENTION

This invention in certain aspects discloses miniaturized, on-skin systems or systems that address these needs through a wireless electronic mode of operation that combines a thermal sensing module for non-contact measurements of a sweat rate and wireless data transfer using a Bluetooth Low Energy (BLE) system on a chip (SoC). This scheme also simplifies the device construction by eliminating the necessity for complex microfluidic networks. Computational modeling and experimental studies validate the underlying physics of operation and guide optimized selection of geometric and materials parameters for accurate, reliable performance. Continuous, on-body measurements of the sweat rate, sweat loss and temperature demonstrate the key sensing capabilities across different body locations and at different body temperatures during exercise and while at rest. Simultaneous, precise tracking of skin temperature illustrates the versatility of the electronics platform in monitoring thermoregulation. Integration with advanced skin-interfaced microfluidic systems and colorimetric chemical reagents extends the utility to hybrid operation, with examples of assessments of pH and measurements of the concentrations of chloride, creatinine and glucose. According to embodiments of the invention, comprehensive sweat analysis is performed with a single-use microfluidic platform paired with a reusable electronics module that remains isolated from sweat and other biofluid contaminants, with broad-ranging options for practical applications in patients, workers, military personnel, athletes and others.

The novel wearable microfluidic technology disclosed in the invention is supported by two main subsystems: (1) a real-time flow-sensor that uses a power-efficient thermal actuator and a collection of precision thermistors, positioned between but isolated from inlet and outlet ports that couple to the skin, and (2) a BLE SoC wireless platform that combines Wheatstone-bridge circuits with reference thermistors and variable gain amplifiers (VGAs) to ensure robust, accurate operation even for extremely low sweat rates. This type of technology allows for measurement and wireless transmission of sweat rates across the physiologically relevant range in a manner that minimizes sensitivity to environmental fluctuations or changes in body temperature over a practical span. The results of benchtop studies and computational modeling validate the key characteristics. On-body measurements demonstrate reliable operation across different body locations, at different body temperatures during exercise and while at rest. Wireless, real-time measurements of sweat rate, total sweat loss and temperature with a reusable module of this type as integrated onto a microfluidic platform for colorimetric detection of pH and concentration of chloride, glucose and creatinine highlight options in enhanced function and hybrid microfluidic/electronic design.

The real-time flow-sensor incorporates a thermal actuator and two thermistors, one for measuring the temperature upstream and the other for downstream relative to the flow direction and the position of the actuator. These components laminate on top of a thin, elastomeric structure that interfaces to an opening (inlet) where sweat enters the system as it releases from the surface of the underlying skin and then passes under the sensor to a corresponding outlet. A double-sided, skin-safe adhesive with a hole aligned to the inlet provides a robust, water-tight seal. The actuator includes eight resistors in series. Applied current generates a constant thermal power at the top surface of the structure and, by thermal diffusion, delivers heat to the flowing sweat below. The flow transports the heat from the actuator directionally downstream, thereby creating a difference between the temperature at the locations of the downstream and the upstream thermistors. Results of computational modeling connect the temperature difference to the flow rate, given the geometrical features of the system and the constitutive properties of the materials.

Soft, thin microfluidic platforms that adhere to the surface of the skin provide many important capabilities for in situ capture, storage and biomarker analysis of sweat. Intricate networks of microchannels, valves and microreservoirs support passive operation and embedded, color responsive chemistries enable visual readout, all without the need for on-board electronics or batteries. Even basic parameters measured with these types of devices, such as sweat rate, sweat loss and electrolyte concentration, have immediate relevance in areas from healthcare to athletic performance and fitness. Nevertheless, for certain applications, including many in worker safety, military training and contact sports, protective equipment prevents visual inspection of the devices; others require continuous digital data streams.

In one aspect, the invention relates to a sensor for measuring parameters of sweat from a skin. The sensor in one embodiment includes a flexible structure comprising a fluid passage having an inlet and an outlet, wherein the flexible structure is detachably attached to the skin and configured such that sweat enters the inlet as the sweat releases from a surface of the skin and flows through the fluid passage into the outlet; a thermal actuator disposed on the flexible structure over the fluid passage and configured to operably provide heat to flow of the sweat through the fluid passage; a first thermistor disposed on the flexible structure over the fluid passage between the inlet and the thermal actuator and configured to operably measure a first temperature of the sweat thereon; and a second thermistor disposed on the flexible structure over the fluid passage between the thermal actuator and the outlet and configured to operably measure a second temperature of the sweat thereon.

In one embodiment, the flexible structure comprises a single layer having a first surface on which the thermal actuator and the first and second thermistors are disposed, an opposite, second surface and a body formed therebetween. The fluid passage is defined inside the body and the inlet extents to the second surface.

In another embodiment, the flexible structure comprises a fluid passage layer having a first surface from which the fluid passage with the inlet and the outlet is defined, and an opposite, second surface, where the inlet extends from the first surface to the second surface; and a top layer disposed on the first surface of the fluid passage layer to seal the fluid passage, wherein the thermal actuator and the first and second thermistors are disposed on the top layer.

In one embodiment, the flexible structure further comprises an adhesive flexible layer have a first surface attached to the second surface of the single layer or the fluid passage layer, an opposite, second surface detachably attached to the skin, and an opening through the first and second surface and aligned to the inlet.

In one embodiment, the flexible structure is formed of a polymer, elastomer, thermoplastics, or silk fibroin. In one embodiment, the polymer comprises poly(dimethylsiloxane) (PDMS), polyurethane, silicone, polyester, or polyethylene.

In one embodiment, the fluid passage has a width of about 500 µm to about about 1 mm, and a height of about 125 µm to about 300 µm, and a thickness defined from a top of the fluid passage to the bottom of the thermal actuator is about 70 µm to about 200 µm.

In one embodiment, the thermal actuator comprises a plurality of resistors connected in series. In one embodiment, the plurality of resistors comprises eight resistors. In one embodiment, the thermal actuator has a diameter of about 0.5 mm to about 2 mm.

In one embodiment, the first and second thermistors are respectively located at a distance upstream and downstream from the center of the actuator.

In one embodiment, the flow of the sweat transports the heat from the thermal actuator directionally downstream, thereby creating a temperature difference between the first temperature at the location of the first thermistor and the second temperature at the location of the second thermistor. In one embodiment, the temperature difference is related to a flow rate of the sweat.

In one embodiment, the sensor is configured to perform continuous, real-time measurements of the flow of the sweat without any direct contact with the sweat.

In one embodiment, the sensor further includes an elastomeric encapsulation layer disposed on the thermal actuator and the first and second thermistors and extended over the flexible structure.

In one embodiment, the sensor further includes a serpentine microfluid passage in fluidic communication with the inlet to allow for manual readout of rate and volume of sweat as the basis for validating the flow measurements.

In another aspect, the invention relates to a system for measuring parameters of sweat from a skin. In one embodiment, the system includes a wireless platform incorporating the sensor as disclosed above and configured to control current to the thermal actuator, process the measured parameters and transmit the processed parameters to an external device.

In one embodiment, the wireless platform comprises a thermal flow-sensing module (TFM) comprising the thermal actuator; a Wheatstone bridge circuit including the first and second thermistors, a reference thermistor and a known resistor on each bridge; and first and second differential amplifiers (AMPs) respectively coupled to the first and second thermistors; and a BLE SoC coupled to the TFM for providing current to the thermal actuator, processing the measured parameters and transmitting the processed parameters to the external device.

In one embodiment, the Wheatstone bridge circuit is configured such that its voltage outputs under different environmental conditions remain around 0 V, thereby imposing no limitation on the amplifier gain or the accuracy of measurements.

In one embodiment, the reference thermistor is located outside the fluid passage but at the same distance from the thermal actuator as the first and second thermistors.

In one embodiment, each AMP amplifies differences between the voltages on the first and second thermistors and a voltage on the reference thermistor to eliminate the effects of temperature differences due to environmental changes.

In one embodiment, the BLE SoC comprises a central processing unit (CPU); at least three VGAs respectively coupled to the first and second AMPs and a reference voltage signal with gain automatically controlled by the CPU; at least three analog-to-digital converters (ADCs) respectively coupled to the at least three VGAs and the CPU; a general-purpose input/output (GPIO) coupled to the CPU and the thermal actuator for operably providing the current to the thermal actuator; and a BLE radio coupled to the CPU for providing two-way communication with the external device.

In one embodiment, each of VGA is configured to amplify the voltage outputs from the Wheatstone bridge circuit, with an adaptive gain to maximize the accuracy of the measurements of resistance within the required dynamic range.

In one embodiment, each of VGA is configured such that as the measured voltage increases and reaches 90% of the upper limit of dynamic range, the gain decreases, thereby increasing the dynamic range; and as the voltage decreases, the gain increases along with the accuracy.

In one embodiment, the at least three ADCs is configured to monitor the bridge voltages on upstream ($V_{UP}$), downstream ($V_{DN}$), and reference ($V_{REF}$) values and control the gain of the VGAs prior to each ADC to achieve the highest resolution within the input voltage range.

In one embodiment, the CPU operably executes digital signal processing on the ADC-sampled data ($V_{UP}$, $V_{DN}$, and $V_{REF}$) to filter out noise.

In one embodiment, the BLE radio is configured to transmit the processed parameters to the external device, and receive data from the external device to activate a GPIO pin to provide the current to the thermal actuator.

In one embodiment, electronics of the wireless platform are formed on thin, flexible copper-clad polyimide sheets that are processed to yield circuit traces that interconnect the TFM and the BLE SoC.

In one embodiment, the system further comprises a third thermistor connected in a voltage divider circuit with a known resistor for measuring temperature of the skin.

In one embodiment, the system is operably adhered to the skin with or without an encapsulated battery mounted mechanically and electrically via matching magnets.

In one embodiment, the external device is configured for real-time graphical display and storage of the parameters.

In one embodiment, the external device is a computer device, a laptop, a tablet, a smartphone, a smart watch, a smart glass, a wearable device, or a mobile device.

In yet another aspect, the invention relates to a system for measuring parameters of sweat from a skin. The parameters comprise at least one of sweat flow, sweat loss, sweat chemistry and skin temperature. In one embodiment, the system includes a flexible structure detachably attached to the skin, comprising a microfluidic network comprising a plurality of microscale reservoirs (µ-RVs); and a plurality of inlet ports for collecting sweat as the sweat releases from a surface of the skin, wherein one inlet port of the plurality of inlet ports is configured to collect the sweat for measuring the sweat flow and loss, and each of the remaining inlet ports of the plurality of inlet ports is in fluidic communication with at least one of the plurality of µ-RVs and configured to collect the sweat for measuring the sweat chemistry.

In one embodiment, the plurality of µ-RVs contain chemical and/or enzymatic assays for colorimetric detection of the sweat chemistry, wherein the sweat chemistry comprises at least one of concentrations of chloride, glucose and/or creatinine in the sweat, and pH of the sweat.

In one embodiment, the flexible structure further comprises a capping layer with a fluid passage having an inlet and an outlet defined therein for measuring the sweat rate and loss; and a color reference layer disposed on the capping layer, wherein the capping layer is disposed on a layer of the microfluidic network such that said one inlet port of the plurality of inlets of the microfluidic network is aligned to and in fluidic communication with the inlet of the fluid passage.

In one embodiment, the microfluidic network is configured such that the sweat collected from said one inlet port passes through the fluid passage of the capping layer, and the sweat collected from said remaining inlet ports enters into the plurality of µ-RVs.

In one embodiment, the microfluidic network comprises capillary bursting valves (CBVs) configured such that the sweat fills each µ-RV in a sequential manner, thereby allowing for measurements of changes in the concentrations of these species in the sweat as a function of the sweat loss.

In one embodiment, the microfluidic network further comprises at least one fluidic channel that is operably in fluidic communication with the fluid passage of the capping layer and is for capture and/or storage of the sweat as it emerges from the outlet of the fluid passage of the capping layer.

In one embodiment, the at least one fluidic channel comprises a serpentine microfluid passage.

In one embodiment, the fluidic network structure further comprises an adhesive layer having a plurality of openings and detachably attached to the skin and the layer of the microfluidic network, such that each of the plurality of openings is aligned to and in fluidic communication with a respective inlet port of the plurality of inlet ports of the microfluidic network.

In one embodiment, the system further comprises a wireless platform operably coupled to the fluid passage of the capper layer for measuring the sweat flow and loss and transmitting the sweat flow and loss to an external device.

In one embodiment, the wireless platform comprises a TFM comprising a thermal actuator disposed on the flexible structure over the fluid passage of the capper layer and configured to operably provide heat to flow of the sweat through the fluid passage; a Wheatstone bridge circuit comprising a first thermistor disposed on the flexible structure over the fluid passage between the inlet and the thermal actuator and configured to operably measure a first temperature of the sweat thereon; a second thermistor disposed on the flexible structure over the fluid passage between the thermal actuator and the outlet and configured to operably measure a second temperature of the sweat thereon; a reference thermistor; and a known resistor on each bridge; and first and second AMPs respectively coupled to the first and second thermistors.

In one embodiment, the Wheatstone bridge circuit is configured such that its voltage outputs under different environmental conditions remain around 0 V, thereby imposing no limitation on the amplifier gain or the accuracy of measurements.

In one embodiment, the reference thermistor is located outside the fluid passage but at the same distance from the thermal actuator as the first and second thermistors.

In one embodiment, each AMP amplifies differences between the voltages on the first and second thermistors and a voltage on the reference thermistor to eliminate the effects of temperature differences due to environmental changes.

In one embodiment, the wireless platform further comprises a BLE SoC coupled to the TFM for providing current to the thermal actuator, processing the measured parameters and transmitting the processed parameters to the external device.

In one embodiment, the BLE SoC comprises a CPU; at least three VGAs respectively coupled to the first and second AMPs and a reference voltage signal with gain automatically controlled by the CPU; at least three ADCs respectively coupled to the at least three VGAs and the CPU; a GPIO coupled to the CPU and the thermal actuator for operably providing the current to the thermal actuator; and a BLE radio coupled to the CPU for providing two-way communication with the external device.

In one embodiment, each of VGA is configured to amplify the voltage outputs from the Wheatstone bridge circuit, with an adaptive gain to maximize the accuracy of the measurements of resistance within the required dynamic range.

In one embodiment, each of VGA is configured such that as the measured voltage increases and reaches 90% of the upper limit of dynamic range, the gain decreases, thereby increasing the dynamic range; and as the voltage decreases, the gain increases along with the accuracy.

In one embodiment, the at least three ADCs is configured to monitor the bridge voltages on upstream ($V_{UP}$), downstream ($V_{DN}$), and reference ($V_{REF}$) values and control the gain of the VGAs prior to each ADC to achieve the highest resolution within the input voltage range.

In one embodiment, the CPU operably executes digital signal processing on the ADC-sampled data ($V_{UP}$, $V_{DN}$, and $V_{REF}$) to filter out noise.

In one embodiment, the BLE radio is configured to transmit the processed parameters to the external device, and receive data from the external device to activate a GPIO pin to provide the current to the thermal actuator.

In one embodiment, the system further comprises a third thermistor connected in a voltage divider circuit with a known resistor for measuring temperature of the skin.

In one embodiment, the external device is configured for real-time graphical display and storage of the parameters. In one embodiment, the external device is a computer device, a laptop, a tablet, a smartphone, a smart watch, a smart glass, a wearable device, or a mobile device.

In one embodiment, the system can be used in industrial safety applications where alerts can be relayed to the worker or to a manager. The approach disclosed in the invention has the potential to be used in personalized hydration strategies, with additional promise for monitoring and managing health disorders.

In one embodiment, the system can be configured to activate alerts to remind users to respond appropriately to avoid heat stress and the risks of dehydration, or to provide prompts to inform rehydration protocols in working or training environments that involve high heat stress conditions or heavy personal protective equipment.

In a further aspect, the invention relates to a method for measuring parameters of sweat from a skin. In one embodiment, the method comprises providing a flexible structure detachably attached to the skin, the flexible structure comprising a fluid passage having an inlet and an outlet configured such that sweat enters the inlet as the sweat releases from a surface of the skin and flows through the fluid passage into the outlet; heating flow of the sweat through the fluid passage at a location between the inlet and the outlet; and measuring a first temperature at a first location of the fluid passage and a second temperature at a second location of the fluid passage, wherein the first location is between the inlet and said location on which the flow of the sweat is heated, the second location is between said location and the outlet, and a distance defined between the first location and said location is identical to that said location and the second location, where the flow of the sweat transports the heat from said location directionally downstream, thereby creating a temperature difference between the first temperature at the first location and the second temperature at the second location.

In one embodiment, the method further comprises processing the measured parameters of the first and second temperatures and wirelessly transmitting the processed parameters to an external device.

In one embodiment, the temperature difference is related to a flow rate of the sweat.

In one embodiment, the method is performed without any direct contact with the sweat.

In one embodiment, the flexible structure further comprises a microfluidic network comprising a plurality of μ-RVs; and a plurality of inlet ports for collecting sweat as the sweat releases from a surface of the skin, wherein one inlet port of the plurality of inlet ports is operably aligned to and in fluidic communication with the inlet of the fluid passage and configured to collect the sweat for measuring the sweat flow and loss, and each of the remaining inlet ports of the plurality of inlet ports is in fluidic communication with at least one of the plurality of μ-RVs and configured to collect the sweat for measuring the sweat chemistry.

In one embodiment, the method further comprises providing chemical and/or enzymatic assays the plurality of μ-RVs; and measuring the sweat chemistry with colorimetric analysis.

In one embodiment, the sweat chemistry comprises at least one of concentrations of chloride, glucose and/or creatinine in the sweat, and pH of the sweat.

In one embodiment, the method further comprises measuring a temperature of the skin.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 1A: Exploded view illustration of the module and its interface with the skin. A straight passage (length>3.4 mm) molded into a structure of PDMS interfaces to the skin through an inlet opening to allow entry of sweat as it emerges from the surface of the skin. A thermal actuator and two thermistors mount on the outer top surface of this passage to support measurements of flow rate, by thermal processes without physical contact with the sweat. FIG. 1B: Picture of a thermal flow sensing module on an index finger. FIG. 1C: Finite element analysis (FEA) of the distribution of temperature through the passage filled with sweat flowing at a rate of 4 μL·min$^{-1}$. The sweat transfers heat from the thermal actuator to a downstream thermistor, thereby increasing its temperature relative to that of an upstream thermistor located at an identical distance from the thermal actuator in the upstream direction ($TH_{UP}$ and $TH_{DN}$). FIG. 1D: Pictures of a thermal actuator on a fluid passage formed with PDMS doped with a thermochromic dye that changes its color from black to pink at temperatures above 25° C. Flow in the passage transfers heat (pink region) in the downstream direction. Top: heat off. Middle Top: heat on, flow at 0 µL·min$^{-1}$. Middle Bottom: heat on, flow at 4 µL·min$^{-1}$. Bottom: heat on, flow at 8 µL·min$^{-1}$.

FIG. 2A: Schematic illustration of the geometry of a thermal actuator with up/down-stream thermistors ($TH_{UP}$ and $TH_{DN}$) resting on the top outer surface of a fluid passage with design parameters for benchtop studies and FEA: diameter of the thermal actuator (D), distance between the actuator and a thermistor (L), width (w) and height (h) of the passage, and thickness of the top layer ($t_{Top}$). FIG. 2B: Infrared (IR) images and FEA results for temperature distribution of an actuator mounted on a passage placed on a hot plate with surface temperature of 34° C. FIG. 2C: Linear temperature profile (inset) within the passage as a function of the distance from the actuator, for flow of 0 and 4 µL·min$^{-1}$, and the temperature difference, T(L)−T(−L), which reaches the maximum for L=1.75 mm. FIGS. 2D-2H: The temperature difference (ΔT) measured (dot) and determined by FEA (line) between the thermistors for different design parameters: the electrical power (P) consumed by a heater (FIG. 2D), D (FIG. 2E), h(f), w (FIG. 2G), and $t_{Top}$ (FIG. 2H). FIG. 2I: Measurements and FEA results for ΔT for a constant flow of 1 µL·min$^{-1}$ as a function of normalized design parameters: h/h$_0$, w/w$_0$, $t_{Top}/t_{Top,0}$ where h$_0$, w$_0$, and $t_{Top,0}$ denote 125 µm, 500 µm, and 70 µm, respectively. Data are presented as mean values (squares)±s.d. (vertical error bars) measured over a 1-min averaging window (sample size=6).

FIG. 3A: Picture of a thin, flexible, remote flow sensing module with Bluetooth Low Energy (BLE) communication capabilities, resting on the tip of an index finger. The width (w) and length (l) of the device are 11.2 mm and 24.8 mm, respectively. The inset provides a side view. FIG. 3B: Photographs of an encapsulated device on the inner wrist, without a battery (Top) and with a magnetically coupled battery (Bottom). FIG. 3C: Circuit and block diagrams of the platform and its wireless interface to a smartphone (BLE radio). The flow sensing module includes a thermal actuator (Joule heater), Wheatstone bridge circuits including thermistors (upstream, downstream, and reference; $TH_{UP}$, $TH_{DN}$, and $TH_{REF}$) with a known resistor (R) on each bridge, and two differential amplifiers (AMPs). A software toggle-switch on the user interface enables BLE-connections to the device and activates a general purpose input/output (GPIO) pin to source a pre-determined current into the thermal actuator. A central processing unit (CPU) controls digital signal processing on the ADC-sampled data (the bridge voltage on upstream, downstream, and reference; $V_{UP}$, $V_{DN}$, and $V_{REF}$) and wirelessly transmits the data over the BLE radio to a user interface. FIG. 3D: Schematic, exploded view illustration of the constituent layers: silicone encapsulation layers, a insulation foam (Flex Foam), electronics, fluid passage, and adhesives. The electronics include a BLE System-on-a-chip (SoC), instrumentation amplifiers (×2), bridge resistors (×3), thermistors (×3), and a heater.

FIG. 4A: Picture of a wireless, skin-interfaced system for continuous, wireless measurement of sweat flow rate, and microfluidic structure for visual read-out, mounted on the forearm. A water-soluble dye (blue) located at the inlet imparts color to the incoming sweat as it flows past, thereby enabling a visually identifiable filling front in the passage. FIG. 4B: Mounting positions (left) on the body: right forearm for subject #1, and both forearms for subject #2, and pictures (right) of the filling front in the fluid passage mounted on the right forearm of subject #2. FIG. 4C: Wirelessly measured temperature difference (ΔT) as a function of flow rate (f), and its linear fit. The calibration factor (C) is C=ΔT/f=0.20 ($R^2$=0.998). FIGS. 4D-4F: Wireless readout of ΔT every 1 min (purple, blue, and red markers) and manual readout of the collected sweat rate (f) every 1 min (black markers) during field testing with healthy subjects while cycling and at rest. Vertical error bars (gray line) represent the standard deviation of ΔT measured over a 1-min averaging window. FIGS. 4G-4I: Cumulative ΔT (ΣΔT; diamond markers) and sweat loss (Σf, square markers) as a function of time measured from the forearm of subject #1 (FIG. 4G), left (FIG. 4H) and right (FIG. 4I) forearms of subject #2. Manual read-out of the collected sweat multiplied by the calibration factor (C×Σf; circle markers) corresponds to the cumulative value of wireless measurements of ΔT.

FIG. 5A: Optical images of an advanced skin-interfaced microfluidic system including a short fluid passage for evaluation of sweat rate/loss and a microscale reservoirs (µ-RVs) for analysis of the sweat chemistry (top), and the device on the forearm (bottom). FIG. 5B: Exploded view illustration of the multilayered structure of the system: wireless platform, color reference markers, a capping layer with a fluid passage, colorimetric assays, microfluidic networks (µ-NETs), and an adhesive layer. FIG. 5C: Graphical images of color reference markers (left) of which color levels extracted from the optical images of color development of assay µ-RVs as a function of sample concentrations (right) of chloride, pH, creatinine, and glucose from top to bottom. FIG. 5D: Results of manual read-out of oral ($T_{oral}$; purple), axillary ($T_{axillary}$; pink), temporal ($T_{temporal}$; green), and skin ($T_{skin,ir}$; blue) temperatures, using commercial thermometers, and wireless read-out of sweat (black) and skin (red) temperatures as a function of time (min) while cycling and at rest. FIG. 5E: Multimodal sensing of sweat concentrations (bar graph) and rate/loss (red). Creatinine not collected due to concentrations below the detection range. N.D. represents data not collected due to insufficient sweat generation.

FIGS. 6A-6B show respectively an optical image of an experimental setup and a wireless electronics platform for bench studies, and an exploded view illustration of the wireless platform configured with Bluetooth Low Energy (BLE) communication capability, according embodiments of the invention.

FIG. 8A: Measurements and FEA predictions of ΔT for flow rates of 0 µL·min$^{-1}$, 1 µL·min$^{-1}$, 2 µL·min$^{-1}$, 3 µL·min$^{-1}$, and 4 µL·min$^{-1}$ at different temperature ($T_s$) settings for the hot plate. FIG. 8B: The mean and root-mean square (RMS) values of ΔT measured over a 30 s averaging window for flow rates of f=0 µL·min$^{-1}$, 1 µL·min$^{-1}$, 2 µL·min$^{-1}$, 3 µL·min$^{-1}$, and 4 µL·min$^{-1}$, and the calibration factors of C=ΔT/f, determined by the slopes of linear fit lines.

FIGS. 10A-10B show measurements of ΔT over extended periods (1 h), according embodiments of the invention. FIG. 10A: ΔT measured for f=0, 1 and 2 µL·min$^{-1}$ in 1-hour testing. FIG. 10B: The mean (dots)±SD (vertical error bars) values of ΔT over 30-s averaging window (sample size=6).

FIG. 11A: Top view. FIG. 11B: Cross-sectional view

FIGS. 14A-14C show respectively effect of normalized parameters L/D (FIG. 14A) and $t_{top}$/h (FIG. 14B), and $k_p/k_F$ (FIG. 14C) in the scaling law, according embodiments of the invention. Reducing L/D, $t_{top}$/h, or $k_p/k_F$ can increase the device sensitivity which is the slope of the normalized temperature difference with respect to the normalized flow rate. (Parameters for the base case: D=2 mm, L=1.7 mm, w=0.5 mm, h=0.125 mm, $t_{top}$=0.07 mm, $q_w$=8.9 mW·mm$^{-2}$, $k_s$=0.6 mW·mm$^{-1}$·K$^{-1}$, $ρ_F c_F$=4.17 mW·mm$^{-1}$·K$^{-1}$, $k_p$=0.27 mW·mm$^-$·K$^{-1}$, which are summarized in Table 3).

FIGS. 15A-15C shows error in flow rate of $f_e$=f−ΔT/$C_{meas}$ as a function of time during field testing with healthy subjects while cycling and at rest, according embodiments of the invention. $C_{meas}$=0.20.

FIGS. 16A-16C show respectively capillary bursting valves (CBVs), CBVs with different channel width and diverging angle, and Calculated bursting pressures of each CBV, according embodiments of the invention. FIG. 16A: Optical image and schematic illustration of the CBVs for chronological sampling. The water flow emerging from the inlet fills the µ-RVs sequentially from #1 to #4 by CBVs. FIG. 16B: Schematic illustrations of CBVs with different channel width and diverging angle. FIG. 16C: Calculated bursting pressures of each CBV.

FIGS. 17A-17B show skin-interfaced microfluidic systems designed to integrate with the flow-sensing platform, according embodiments of the invention. FIG. 17A: a, Optical images showing that sweat emerging from the forehead perfuse into the sweat flow sensing part in the capping layer and then moves to the sweat capture/storage part in the µ-NETs (a serpentine channel and a collection of µ-RVs separated by valves). FIG. 17B: Schematic illustration the device.

FIGS. 18A-18B show the full-assembled system, according embodiments of the invention. FIG. 18A: The assembled view of illustration. FIG. 18B: Optical image of the full-assembled system, mounted on the forehead of a healthy male volunteer.

FIG. 22A: Digital images of µ-RVs for chronological sampling of pH (top) and Chloride (bottom) levels, taken after 7 min, 12 min, 17 min, and 29 min of exercise. FIG. 22B: Measurements (dots, data points) using the digital images taken 20 min after 36 min of exercise. Chloride and pH levels increase as sweating during exercise. Data are represented as mean values (bar graph)±SD (vertical error bars) measured at three different locations from each assay (sample size=3).

FIG. 24A: Circuit and block diagrams of the platform for multimodal sensing of sweat rate/loss and skin temperatures, and its wireless interface to a smartphone (BLE radio). The skin temperature sensing module includes a thermistor ($TH_{skin}$, 15.5 mm away from the heater) with a known resistor (R). FIG. 24B: Pictures of a device measuring sweat rate and skin temperature with the heat on (top) and sweat/skin temperatures by turning off the heat and placing the upstream thermistor on the inlet of a microfluidic passage (bottom). FIG. 24C: Sensing points on the body for multimodal sensing of skin/sweat temperatures using a device.

FIG. 25A: The difference between $T_{sweat}$ and $T_{skin}$, ΔT=$T_{sweat}$−$T_{skin}$, every 1 min while cycling and at rest. FIG. 25B: Wireless measurements of $T_{sweat}$ and $T_{skin}$ with mean values (dots)±SD (vertical error bars) measured over 1 min averaging window (sample size=600).

FIG. 26A: Wireless readout of sweat rate (blue) and skin temperature (red) every 1 min and manual readout of the temporal temperature (black) as a function of time (min) while cycling and at rest. Data are presented as mean values±SD (sample size=600). FIG. 26B: Mounting position on the body.

DETAILED DESCRIPTION OF THE INVENTION

Figure 1A:
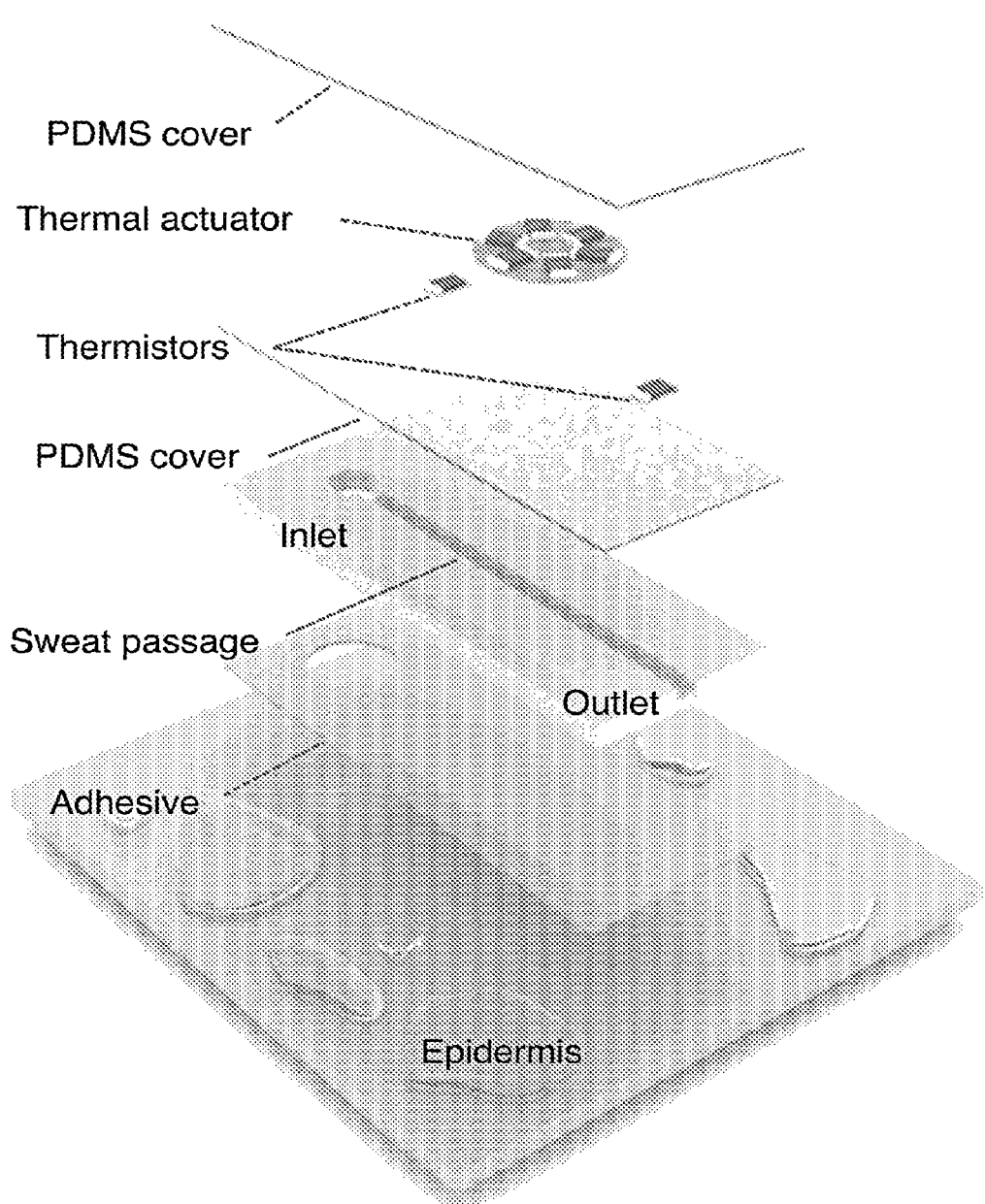
FIGS. 1A-1D show design features and operating principles of a miniaturized, flexible module for remote, on-skin sensing of sweat rate, according embodiments of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures.

It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this disclosure, the phrase "at least one of A, B, and C" should be construed to mean a logical (A or B or C), using a non-exclusive logical OR. As used herein, the term "and/or" includes any and all combinations of one or more of the associated listed items.

"Interfacing" refers to the positioning of the device with tissue such that the device may affect the tissue, and vice versa. For example, a thermal actuator of the device may result in a thermal load provided to the tissue in the form of a "thermal input". The thermal input is preferable a heating action, although the device is also compatible with a cooling action. "Thermally interfacing", therefore, refers to the ability of the device to affect a thermal challenge on underlying tissue, and to detect a response thereto, such as a change in temperature over time, including for a time period after the thermal input ends. In this manner, one or more tissue parameters may be determined, such as tissue hydration, inflammation, blood flow, UV damage.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. As used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

Any of the devices provided herein may be described in terms of elasticity or elastic. "Elasticity" refers to a measure of a non-plastic deformation, such as a deformation that can undergo deformation and relaxation back to the original undeformed, state without substantial creep, including under repeated deformatory stresses and relaxation cycles. The creep may be defined as less than a 5%, less than 2%, or less than 1% permanent deformation or change in the original material property.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island—bridge geometry. Stretchable device components include structures having stretchable interconnects, such as stretchable electrical interconnects.

"Two-way communication" refers to the ability to wirelessly communicate with the device, such that power, commands or queries are sent to, and acted on, the device and the device itself can send information or diagnostics to an external controller that is wirelessly connected to the device. Accordingly, an "external controller" refers to an off-board component that can control and received information from the device. Examples include hand-held devices, computers, smartphones, and the like.

The devices and methods provided herein are suited for long-term use in that the device may be "worn" over long periods of time and remain functional. Accordingly, "continuous" refers to the time period any of the devices provided herein are deployed on or in biological tissue and is ready for use. While the device is continuously deployed, the measurement may be described as intermittent or periodic, such as for a continuous measurement time on the order of minutes, such as greater than or equal to 1 minute, 5 minutes, 10 minutes or 20 minutes. The periodic measurement, however, can be repeated over the time period the device is worn, such as in the morning, during the day, and in the evening, including on the order of 12 hours or more, 1 day or more, or 7 days or more.

"Thermal parameter" or "thermal transport property" may refer to a rate of change of a temperature-related tissue property, such as a heat-related tissue property, over time and/or distance (velocity). In some embodiments, the heat-related tissue property may be temperature, conductivity or humidity. The heat-related tissue property may be used to determine a thermal transport property of the tissue, where the "thermal transport property" relates to heat flow or distribution at or near the tissue surface. In some embodiments, thermal transport properties include temperature distribution across a tissue surface, thermal conductivity, thermal diffusivity and heat capacity. Thermal transport properties, as evaluated in the present methods and systems, may be correlated with a physical or physiological property of the tissue. In some embodiments, a thermal transport property may correlate with a temperature of tissue. In some embodiments, a thermal transport property may correlate with a vasculature property, such as blood flow and/or direction.

"Substrate" refers to a portion of the device that provides mechanical support for a component(s) disposed on or within the substrate. The substrate may have at least one skin-related function or purpose. For example, the substrate may have a mechanical functionality, for example, providing physical and mechanical properties for establishing conformal contact at the interface with a tissue, such as skin or a nail surface. The substrate may have a thermal loading or mass small enough so as to avoid interference with measurement and/or characterization of a tissue parameter. The substrate of any of the present devices and methods may be biocompatible and/or bioinert. A substrate may facilitate mechanical, thermal, chemical and/or electrical matching to the underlying tissue, such as skin or nail of a subject such that the mechanical, thermal, chemical and/or electrical properties of the substrate and the tissue are within 20%, or 15%, or 10%, or 5% of one another.

A flexible substrate that is mechanically matched to a tissue, such as skin, provides a conformable interface, for example, useful for establishing conformal contact with the surface of the tissue. Devices and methods described herein may incorporate mechanically functional substrates comprising soft materials, for example exhibiting flexibility and/or stretchability, such as polymeric and/or elastomeric materials. A mechanically matched substrate may have a Young's modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

In some embodiments, a mechanically matched substrate is characterized by one or more mechanical properties and/or physical properties that are within a specified factor of the same parameter for an epidermal layer of the skin or nail, such as a factor of 10 or a factor of 2. For example, a substrate may have a Young's Modulus or thickness that is within a factor of 20, or optionally for some applications within a factor of 10, or optionally for some applications within a factor of 2, of a tissue, such as an epidermal layer of the skin or of the nail surface, at the interface with a device of the present invention. A mechanically matched substrate may have a mass or modulus that is equal to or lower than that of skin.

In some embodiments, a substrate that is thermally matched to skin has a thermal mass small enough that deployment of the device does not result in a thermal load on the tissue, such as skin, or small enough so as not to impact measurement and/or characterization of a physiological parameter. In some embodiments, for example, a substrate that is thermally matched to skin has a thermal mass low enough such that deployment on skin results in an increase in temperature of less than or equal to 2 degrees Celsius, and optionally for some applications less than or equal to 1 degree Celsius, and optionally for some applications less than or equal to 0.5 degree Celsius, and optionally for some applications less than or equal to 0.1 degree Celsius. In some embodiments, for example, a substrate that is thermally matched to skin has a thermal mass low enough that is does not significantly disrupt water loss from the skin, such as avoiding a change in water loss by a factor of 1.2 or greater. Therefore, the device does not substantially induce sweating or significantly disrupt transdermal water loss from the skin, while maintaining an effectiveness of determining hydration state of the skin.

The substrate may have a Young's modulus less than or equal to 100 MPa, or less than or equal to 50 MPa, or less than or equal to 10 MPa, or less than or equal to 100 kPa, or less than or equal to 80 kPa, or less than or equal to 50 kPa. Further, in some embodiments, the device may have a thickness less than or equal to 5 mm, or less than or equal to 2 mm, or less than or equal to 100 μm, or less than or equal to 50 μm, and a net bending stiffness less than or equal to 1 nN m, or less than or equal to 0.5 nN m, or less than or equal to 0.2 nN m. For example, the device may have a net bending stiffness selected from a range of 0.1 to 1 nN m, or 0.2 to 0.8 nN m, or 0.3 to 0.7 nN m, or 0.4 to 0.6 nN m.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures. The encapsulation may be described in functional terms, such as being a fluid or electrical barrier, particularly in those locations where a fluid or electrical field would lead to an adverse impact on the device.

"Conformable" refers to a device, material or substrate which has a bending stiffness that is sufficiently low to allow the device, material or substrate to adopt any desired contour profile, for example a contour profile allowing for conformal contact with a curvilinear surface, including a surface whose shape may change over time, such as with physical exertion or normal every day movement, such as skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. Devices of certain aspects are capable of establishing conformal contact with internal and external tissue. Devices of certain aspects are capable of establishing conformal contact with tissue surfaces characterized by a range of surface morphologies including planar, curved, contoured, macro-featured and micro-featured surfaces and any combination of these. Devices of certain aspects are capable of establishing conformal contact with tissue surfaces corresponding to tissue undergoing movement, including an internal organ or skin.

Any of the devices and methods provided herein may be personalized to a user. In this context, "personalized" refers to the device or method that is tailored to that of an individual user, recognizing there may be relatively significant person-to-person variability with respect to one or more baseline tissue parameters, and tissue behavior to a stimulus. For example, some people may have higher inherent thermal conductivity, or high resting hydration level. The devices or methods may accurately determine the baseline tissue parameter, with monitoring and corresponding treatment tailored to that individual's baseline tissue parameter.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Soft, thin microfluidic platforms that adhere to the surface of the skin provide many important capabilities for in situ capture, storage and biomarker analysis of sweat. Intricate networks of microchannels, valves and microreservoirs support passive operation and embedded, color responsive chemistries enable visual readout, all without the need for on-board electronics or batteries. Even basic parameters measured with these types of devices, such as sweat rate, sweat loss and electrolyte concentration, have immediate relevance in areas from healthcare to athletic performance and fitness. Nevertheless, for certain applications, including many in worker safety, military training and contact sports, protective equipment prevents visual inspection of the devices; others require continuous digital data streams.

This invention in certain aspects discloses miniaturized, on-skin systems or systems that address these needs through a wireless electronic mode of operation that combines a thermal sensing module for non-contact measurements of a sweat rate and wireless data transfer using a Bluetooth Low Energy (BLE) system on a chip (SoC). This scheme also simplifies the device construction by eliminating the necessity for complex microfluidic networks. Computational modeling and experimental studies validate the underlying physics of operation and guide optimized selection of geometric and materials parameters for accurate, reliable performance. Continuous, on-body measurements of the sweat rate, sweat loss and temperature demonstrate the key sensing capabilities across different body locations and at different body temperatures during exercise and while at rest. Simultaneous, precise tracking of skin temperature illustrates the versatility of the electronics platform in monitoring thermoregulation. Integration with advanced skin-interfaced microfluidic systems and colorimetric chemical reagents extends the utility to hybrid operation, with examples of assessments of pH and measurements of the concentrations of chloride, creatinine and glucose. According to embodiments of the invention, comprehensive sweat analysis is performed with a single-use microfluidic platform paired with a reusable electronics module that remains isolated from sweat and other biofluid contaminants, with broad-ranging options for practical applications in patients, workers, military personnel, athletes and others.

In one aspect, the invention relates to a sensor for measuring parameters of sweat from a skin. The sensor in one embodiment includes a flexible structure comprising a fluid passage having an inlet and an outlet, wherein the flexible structure is detachably attached to the skin and configured such that sweat enters the inlet as the sweat releases from a surface of the skin and flows through the fluid passage into the outlet; a thermal actuator disposed on the flexible structure over the fluid passage and configured to operably provide heat to flow of the sweat through the fluid passage; a first thermistor disposed on the flexible structure over the fluid passage between the inlet and the thermal actuator and configured to operably measure a first temperature of the sweat thereon; and a second thermistor disposed on the flexible structure over the fluid passage between the thermal actuator and the outlet and configured to operably measure a second temperature of the sweat thereon.

In one embodiment, the flexible structure comprises a single layer having a first surface on which the thermal actuator and the first and second thermistors are disposed, an opposite, second surface and a body formed therebetween. The fluid passage is defined inside the body and the inlet extents to the second surface.

In another embodiment, the flexible structure comprises a fluid passage layer having a first surface from which the fluid passage with the inlet and the outlet is defined, and an opposite, second surface, where the inlet extends from the first surface to the second surface; and a top layer disposed on the first surface of the fluid passage layer to seal the fluid passage, wherein the thermal actuator and the first and second thermistors are disposed on the top layer.

In one embodiment, the flexible structure further comprises an adhesive flexible layer having a first surface attached to the second surface of the single layer or the fluid passage layer, an opposite, second surface detachably attached to the skin, and an opening through the first and second surface and aligned to the inlet.

In one embodiment, the flexible structure is formed of a polymer, elastomer, thermoplastics, or silk fibroin. In one embodiment, the polymer comprises poly(dimethylsiloxane) (PDMS), polyurethane, silicone, polyester, or polyethylene.

In one embodiment, the fluid passage has a width of about 500 μm to about about 1 mm, and a height of about 125 μm to about 300 μm, and a thickness defined from a top of the fluid passage to the bottom of the thermal actuator is about 70 μm to about 200 μm.

In one embodiment, the thermal actuator comprises a plurality of resistors connected in series. In one embodiment, the plurality of resistors comprises eight resistors. In one embodiment, the thermal actuator has a diameter of about 0.5 mm to about 2 mm.

In one embodiment, the first and second thermistors are respectively located at a distance upstream and downstream from the center of the actuator.

In one embodiment, the flow of the sweat transports the heat from the thermal actuator directionally downstream, thereby creating a temperature difference between the first temperature at the location of the first thermistor and the second temperature at the location of the second thermistor. In one embodiment, the temperature difference is related to a flow rate of the sweat.

In one embodiment, the sensor is configured to perform continuous, real-time measurements of the flow of the sweat without any direct contact with the sweat.

In one embodiment, the sensor further includes an elastomeric encapsulation layer disposed on the thermal actuator and the first and second thermistors and extended over the flexible structure.

In one embodiment, the sensor further includes a serpentine microfluid passage in fluidic communication with the inlet to allow for manual readout of rate and volume of sweat as the basis for validating the flow measurements.

In another aspect, the invention relates to a system for measuring parameters of sweat from a skin. In one embodiment, the system includes a wireless platform incorporating the sensor as disclosed above and configured to control current to the thermal actuator, process the measured parameters and transmit the processed parameters to an external device.

In one embodiment, the wireless platform comprises a thermal flow-sensing module (TFM) comprising the thermal actuator; a Wheatstone bridge circuit including the first and second thermistors, a reference thermistor and a known resistor on each bridge; and first and second differential amplifiers (AMPs) respectively coupled to the first and second thermistors; and a BLE SoC coupled to the TFM for providing current to the thermal actuator, processing the measured parameters and transmitting the processed parameters to the external device.

In one embodiment, the Wheatstone bridge circuit is configured such that its voltage outputs under different environmental conditions remain around 0 V, thereby imposing no limitation on the amplifier gain or the accuracy of measurements.

In one embodiment, the reference thermistor is located outside the fluid passage but at the same distance from the thermal actuator as the first and second thermistors.

In one embodiment, each AMP amplifies differences between the voltages on the first and second thermistors and a voltage on the reference thermistor to eliminate the effects of temperature differences due to environmental changes.

In one embodiment, the BLE SoC comprises a central processing unit (CPU); at least three VGAs respectively coupled to the first and second AMPs and a reference voltage signal with gain automatically controlled by the CPU; at least three analog-to-digital converters (ADCs) respectively coupled to the at least three VGAs and the CPU; a general-purpose input/output (GPIO) coupled to the CPU and the thermal actuator for operably providing the current to the thermal actuator; and a BLE radio coupled to the CPU for providing two-way communication with the external device.

In one embodiment, the sensed sweat information can be used to communicate with one or more external systems, resulting in a change in operation of an external system. For example, the system can send a signal (e.g., wired or wireless) to a remote system and the signal can cause the remote system to change its operation or the operation of a system under its control (e.g. an external device such as a thermostat (e.g. Google Nest) or a personal assistant device (e.g. Amazon Echo, Google Home, Siri), or implantable device including but not limited to cardiac pacemaker or a deep brain stimulator or a vagus nerve stimulator, or a wearable device such as a skin-mounted stimulation or drug delivery device). In another example, the system can detect or predict a problematic sweat rate or skin temperature change (e.g., up or down to an unsafe level or range) and can then send a signal to a thermostat, which can cause a change in ambient temperature in the environment to offset the detected or predicted sweat rate and skin temperature.

In one embodiment, each of VGA is configured to amplify the voltage outputs from the Wheatstone bridge circuit, with an adaptive gain to maximize the accuracy of the measurements of resistance within the required dynamic range.

In one embodiment, each of VGA is configured such that as the measured voltage increases and reaches 90% of the upper limit of dynamic range, the gain decreases, thereby increasing the dynamic range; and as the voltage decreases, the gain increases along with the accuracy.

In one embodiment, the at least three ADCs is configured to monitor the bridge voltages on upstream ($V_{UP}$), downstream ($V_{DN}$), and reference ($V_{REF}$) values and control the gain of the VGAs prior to each ADC to achieve the highest resolution within the input voltage range.

In one embodiment, the CPU operably executes digital signal processing on the ADC-sampled data ($V_{UP}$, $V_{DN}$, and $V_{REF}$) to filter out noise.

In one embodiment, the BLE radio is configured to transmit the processed parameters to the external device, and receive data from the external device to activate a GPIO pin to provide the current to the thermal actuator.

In one embodiment, electronics of the wireless platform are formed on thin, flexible copper-clad polyimide sheets that are processed to yield circuit traces that interconnect the TFM and the BLE SoC.

In one embodiment, the system further comprises a third thermistor connected in a voltage divider circuit with a known resistor for measuring temperature of the skin.

In one embodiment, the system is operably adhered to the skin with or without an encapsulated battery mounted mechanically and electrically via matching magnets.

In one embodiment, the external device is configured for real-time graphical display and storage of the parameters.

In one embodiment, the external device is a computer device, a laptop, a tablet, a smartphone, a smart watch, a smart glass, a wearable device, or a mobile device.

In yet another aspect, the invention relates to a system for measuring parameters of sweat from a skin. The parameters comprise at least one of sweat flow, sweat loss, sweat chemistry and skin temperature. In one embodiment, the system includes a flexible structure detachably attached to the skin, comprising a microfluidic network comprising a plurality of microscale reservoirs (μ-RVs); and a plurality of inlet ports for collecting sweat as the sweat releases from a surface of the skin, wherein one inlet port of the plurality of inlet ports is configured to collect the sweat for measuring the sweat flow and loss, and each of the remaining inlet ports of the plurality of inlet ports is in fluidic communication with at least one of the plurality of μ-RVs and configured to collect the sweat for measuring the sweat chemistry.

In one embodiment, the plurality of μ-RVs contain chemical and/or enzymatic assays for colorimetric detection of the sweat chemistry, wherein the sweat chemistry comprises at least one of concentrations of chloride, glucose and/or creatinine in the sweat, and pH of the sweat.

In one embodiment, the flexible structure further comprises a capping layer with a fluid passage having an inlet and an outlet defined therein for measuring the sweat rate and loss; and a color reference layer disposed on the capping layer, wherein the capping layer is disposed on a layer of the microfluidic network such that said one inlet port of the plurality of inlets of the microfluidic network is aligned to and in fluidic communication with the inlet of the fluid passage.

In one embodiment, the microfluidic network is configured such that the sweat collected from said one inlet port passes through the fluid passage of the capping layer, and the sweat collected from said remaining inlet ports enters into the plurality of μ-RVs.

In one embodiment, the microfluidic network comprises capillary bursting valves (CBVs) configured such that the sweat fills each μ-RV in a sequential manner, thereby allowing for measurements of changes in the concentrations of these species in the sweat as a function of the sweat loss.

In one embodiment, the microfluidic network further comprises at least one fluidic channel that is operably in fluidic communication with the fluid passage of the capping layer and is for capture and/or storage of the sweat as it emerges from the outlet of the fluid passage of the capping layer.

In one embodiment, the at least one fluidic channel comprises a serpentine microfluid passage.

In one embodiment, the fluidic network structure further comprises an adhesive layer having a plurality of openings and detachably attached to the skin and the layer of the microfluidic network, such that each of the plurality of openings is aligned to and in fluidic communication with a respective inlet port of the plurality of inlet ports of the microfluidic network.

In one embodiment, the system further comprises a wireless platform operably coupled to the fluid passage of the capper layer for measuring the sweat flow and loss and transmitting the sweat flow and loss to an external device.

In one embodiment, the wireless platform comprises a TFM comprising a thermal actuator disposed on the flexible structure over the fluid passage of the capper layer and configured to operably provide heat to flow of the sweat through the fluid passage; a Wheatstone bridge circuit comprising a first thermistor disposed on the flexible structure over the fluid passage between the inlet and the thermal actuator and configured to operably measure a first temperature of the sweat thereon; a second thermistor disposed on the flexible structure over the fluid passage between the thermal actuator and the outlet and configured to operably measure a second temperature of the sweat thereon; a reference thermistor; and a known resistor on each bridge; and first and second AMPS respectively coupled to the first and second thermistors.

In one embodiment, the Wheatstone bridge circuit is configured such that its voltage outputs under different environmental conditions remain around 0 V, thereby imposing no limitation on the amplifier gain or the accuracy of measurements.

In one embodiment, the reference thermistor is located outside the fluid passage but at the same distance from the thermal actuator as the first and second thermistors.

In one embodiment, each AMP amplifies differences between the voltages on the first and second thermistors and a voltage on the reference thermistor to eliminate the effects of temperature differences due to environmental changes.

In one embodiment, the wireless platform further comprises a BLE SoC coupled to the TFM for providing current to the thermal actuator, processing the measured parameters and transmitting the processed parameters to the external device.

In one embodiment, the BLE SoC comprises a CPU; at least three VGAs respectively coupled to the first and second AMPs and a reference voltage signal with gain automatically controlled by the CPU; at least three ADCs respectively coupled to the at least three VGAs and the CPU; a GPIO coupled to the CPU and the thermal actuator for operably providing the current to the thermal actuator; and a BLE radio coupled to the CPU for providing two-way communication with the external device.

In one embodiment, each of VGA is configured to amplify the voltage outputs from the Wheatstone bridge circuit, with an adaptive gain to maximize the accuracy of the measurements of resistance within the required dynamic range.

In one embodiment, each of VGA is configured such that as the measured voltage increases and reaches 90% of the upper limit of dynamic range, the gain decreases, thereby increasing the dynamic range; and as the voltage decreases, the gain increases along with the accuracy.

In one embodiment, the at least three ADCs is configured to monitor the bridge voltages on upstream ($V_{UP}$), downstream ($V_{DN}$), and reference ($V_{REF}$) values and control the gain of the VGAs prior to each ADC to achieve the highest resolution within the input voltage range.

In one embodiment, the CPU operably executes digital signal processing on the ADC-sampled data ($V_{UP}$, $V_{DN}$, and $V_{REF}$) to filter out noise.

In one embodiment, the BLE radio is configured to transmit the processed parameters to the external device, and receive data from the external device to activate a GPIO pin to provide the current to the thermal actuator.

In one embodiment, the system further comprises a third thermistor connected in a voltage divider circuit with a known resistor for measuring temperature of the skin. In one embodiment, the external device is configured for real-time graphical display and storage of the parameters. In one embodiment, the external device is a computer device, a laptop, a tablet, a smartphone, a smart watch, a smart glass, a wearable device, or a mobile device. In one embodiment, the external device can analyze the sweat sensor data and initiate an environmental response. For example, the external device can receive processed parameters of the sensed sweat rate and skin temperature data to directly control the heating and/or cooling (e.g., turn the HVAC system on or off, or adjust the thermostat) for the room.

In one embodiment, the external device can analyze the sweat sensor data in combination with other data to initiate a set of commands relayed to a personal assistant device (e.g. Amazon Echo, Google Home, Siri). For example, the sweat rate, sweat electrolytes, and skin temperature data can be transmitted to an external personal assistant over a public or private network and can be used to initiate an intervention such as an e-commerce purchase of bottled water or electrolyte-infused sports drinks to initiate a rehydration strategy.

In one embodiment, the system can be used in industrial safety applications where alerts can be relayed to the worker or to a manager. The approach disclosed in the invention has the potential to be used in personalized hydration strategies, with additional promise for monitoring and managing health disorders.

In one embodiment, the system can be configured to activate alerts to remind users to respond appropriately to avoid heat stress and the risks of dehydration, or to provide prompts to inform rehydration protocols in working or training environments that involve high heat stress conditions or heavy personal protective equipment.

In a further aspect, the invention relates to a method for measuring parameters of sweat from a skin. In one embodiment, the method comprises providing a flexible structure detachably attached to the skin, the flexible structure comprising a fluid passage having an inlet and an outlet configured such that sweat enters the inlet as the sweat releases from a surface of the skin and flows through the fluid passage into the outlet; heating flow of the sweat through the fluid passage at a location between the inlet and the outlet; and measuring a first temperature at a first location of the fluid passage and a second temperature at a second location of the fluid passage, wherein the first location is between the inlet and said location on which the flow of the sweat is heated, the second location is between said location and the outlet, and a distance defined between the first location and said location is identical to that said location and the second location, where the flow of the sweat transports the heat from said location directionally downstream, thereby creating a temperature difference between the first temperature at the first location and the second temperature at the second location.

In one embodiment, the method further comprises processing the measured parameters of the first and second temperatures and wirelessly transmitting the processed parameters to an external device.

In one embodiment, the temperature difference is related to a flow rate of the sweat.

In one embodiment, the method is performed without any direct contact with the sweat.

In one embodiment, the flexible structure further comprises a microfluidic network comprising a plurality of µ-RVs; and a plurality of inlet ports for collecting sweat as the sweat releases from a surface of the skin, wherein one inlet port of the plurality of inlet ports is operably aligned to and in fluidic communication with the inlet of the fluid passage and configured to collect the sweat for measuring the sweat flow and loss, and each of the remaining inlet ports of the plurality of inlet ports is in fluidic communication with at least one of the plurality of µ-RVs and configured to collect the sweat for measuring the sweat chemistry.

In one embodiment, the method further comprises providing chemical and/or enzymatic assays the plurality of µ-RVs; and measuring the sweat chemistry with colorimetric analysis.

In one embodiment, the sweat chemistry comprises at least one of concentrations of chloride, glucose and/or creatinine in the sweat, and pH of the sweat.

In one embodiment, the method further comprises measuring a temperature of the skin.

The soft, skin-interfaced, wireless platform/device according to the invention presents, among other things, many advantages over existing technologies. A key feature of this device is that its operation does not rely on an elaborate microfluidic structure, but only on a short, straight flow segment between an inlet interface to the skin and an outlet to the surroundings. The device is mounted on the forearm but with an extended configuration that also includes a serpentine microfluidic passage to allow for manual readout of sweat rate and volume as the basis for validating the flow measurements. The device in certain embodiments performs temperature measurements at an about 200-Hz sampling rate and transmits an averaged value every 0.1 seconds (10 Hz) to a user interface. Software applications save the wireless readings (10 data per second) into the memory of the smartphone and display the averaged value every minute, synchronized with manual reading of the position of the filling front by capture and analysis of digital images of the device. The device is also capable of measuring skin temperature, as a critical parameter that is complementary to sweat in the context of cutaneous heat loss, body heat content, and central thermoregulatory control. The device further supports noninvasive, continuous monitoring of the sweat rate/loss, and skin temperature. Integration with advanced microfluidic systems and colorimetric chemical or enzymatic reagents provide accurate colorimetric estimates of chloride concentration and pH, as well as biomarkers such as creatinine and glucose. In addition, computational modeling, experimental studies, and field trials in healthy subjects demonstrate these multifunctional capabilities in skin-compatible, wearable systems for sweat analysis, with bioassays relevant to monitoring physical activity and hydration. These approaches support comprehensive capabilities in sweat analysis, with potential use in personalized hydration strategies, with additional potential for monitoring and managing health disorders.

These and other aspects of the present invention are further described below. Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLE

Miniaturized, On-Skin Electronic Systems for Wireless, Real-Time Monitoring of Flow Rate, Cumulative Loss and Temperature of Sweat An essential requirement for measurements of the flow rate of sweat as it emerges from the surface of the skin is the capacity for robust operation during intense physical activity and variable environmental conditions (air currents, temperature fluctuations). Ideal solutions are in wireless platforms that isolate the electronics from surrounding biofluids (sweat, oils, etc.), in re-usable formats, with options for integration with microfluidic systems.

In this exemplary example, a skin-interfaced platform that can wirelessly monitor the flow rate, cumulative loss and temperature of sweat in real time is disclosed. The platform captures sweat as it emerges from the surface of the skin, using a short, straight fluid passage. The method thus avoids the need for complex microfluidic networks and it isolates the electronics from the surrounding biofluids. The platform uses a non-invasive flow sensor consisting of a power-efficient thermal actuator and a collection of precision thermistors, all thermally coupled to the sweat but not in direct contact with it. The approach can measure and wirelessly transmit sweat rates across the physiologically relevant range (from 0 to 5 µL min$^{-1}$) in a manner that minimizes sensitivity to environmental fluctuations (air currents/convection) and changes in body temperature over a practical span (such as 25° C. to 35° C.). For automatic and continuous (up to 200-Hz sampling rate) updates to user-friendly portable devices, we integrate a Bluetooth Low Energy (BLE) system-on-a-chip (SoC) wireless platform that combines Wheatstone-bridge circuits with reference thermistors and variable gain amplifiers (VGAs). In contrast to other systems, the active components remain separated from the body and the sweat, and operation does not impose limits on the measurable volumes of sweat. On-body measurements across different body locations, at different body temperatures and during exercise and while at rest, demonstrate the key capabilities. The system can also be integrated with advanced microfluidic systems for colorimetric detection of pH as well as the concentrations of chloride, glucose and creatinine.

Non-Invasive, Miniaturized, Flow Sensors

Figure 1B:
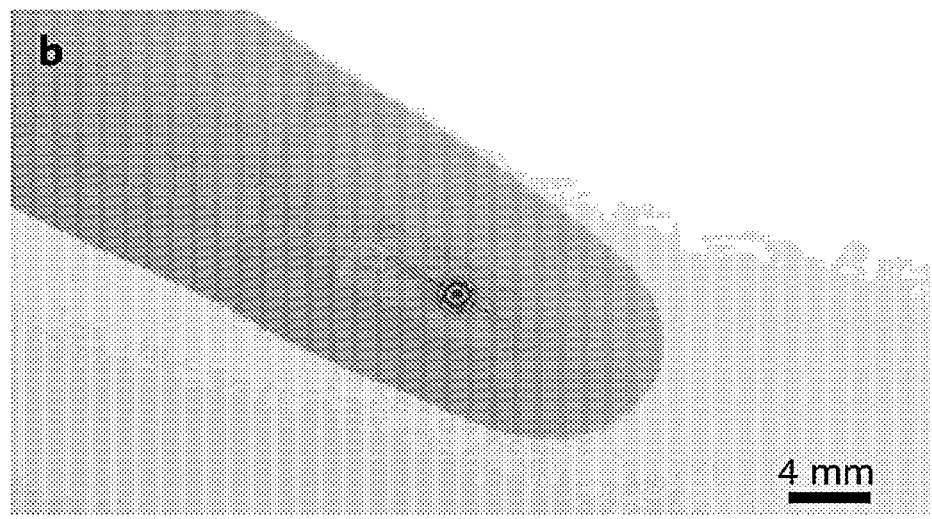
Figure 1C:
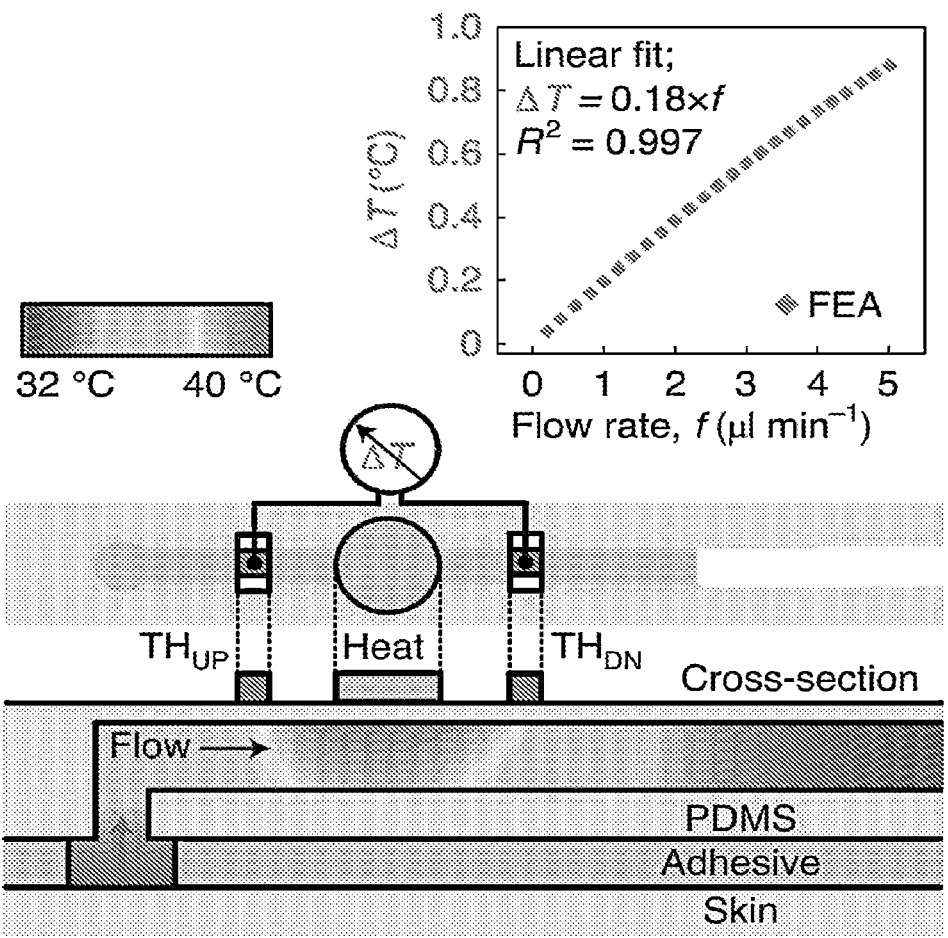

The sensor, illustrated in FIG. 1A, incorporates a thermal actuator and two thermistors, one for measuring the temperature upstream and the other for downstream relative to the flow direction and the position of the actuator. These components are laminated on top of a thin, elastomeric structure that interfaces with an opening (inlet) where sweat enters the system as it releases from the surface of the underlying skin and then passes under the sensor to a corresponding outlet. A double-sided, skin-safe adhesive with a hole (diameter=5 mm) aligned to the inlet provides a robust, water-tight seal and determines the sweat collection area ($\pi r^2$). As in the design highlighted in FIG. 1B, the actuator (diameter=2 mm) includes eight resistors (8×35.6Ω) in series, each with a width of 0.3 mm, a length of 0.6 mm, and a height of 0.25 mm. Applied current generates a constant thermal power ($P_d$=9.07 mW·mm$^{-2}$) at the top surface of the structure and, by thermal diffusion, delivers heat to the flowing sweat below (width, height, and top layer thickness of 500 µm, 125 µm, and 70 µm, respectively). The flow transports the heat from the actuator directionally downstream, thereby creating a difference between the temperature at the locations of the downstream ($TH_{DN}$) and the upstream ($TH_{UP}$) thermistors. For the device reported here, the thermistors (width and length of 0.3 mm and 0.6 mm, respectively) lie at positions 1.7 mm downstream and upstream from the center of the actuator. Results of computational modeling connect the temperature difference ($\Delta T$) to the flow rate (f), given the geometrical features of the system and the constitutive properties of the materials. FIG. 1C shows computational predictions for the temperature distribution for the case of flow at a rate of 4 µL·min$^{-1}$, which is representative for sweating on the forearm for male subjects riding a stationary bike. The inset highlights result of finite-element analysis (FEA) that establishes a simple, linear empirical relationship, $\Delta T$=0.18×f, with $R^2$=0.997, that is applicable across the full range of physiologically relevant rates of sweating during exercise for the particular system described here. The full-body sweat rate for an adult can reach 2-4 liters per hour, through about 1.6 to 5 million sweat glands distributed across the skin. The number of glands per unit area varies with position (e.g., about 200 glands per cm$^2$ on the extensor surface of the forearm, 175 on the upper arm over bicep, 280 on the thenar eminence of the hand, 150 on the anterior chest, and 100 on the medial surface of leg over gastrocnemius). Openings of a skin-compatible adhesive layer that spatially align with the inlet of the microfluidic channel define the sweat harvesting area (e.g. 0.5 cm radius, corresponding to ~200 [glands per cm$^2$]×π×0.5$^2$ [cm$^2$]=157 glands on the forearm). At a maximum sweat rate of 4 liters per hour through a total of 5 million glands, the sweat that passes through the inlet in the device (diameter=0.5 cm) when placed on the forearm corresponds to a flow of f=4 [liters per hour]/5 [million glands]×200 [glands per cm$^2$]×π×0.5$^2$ [cm$^2$]=2.1 µL·min$^{-1}$, near the midpoint of the range examined in the inset to FIG. 1C.

Figure 1D:
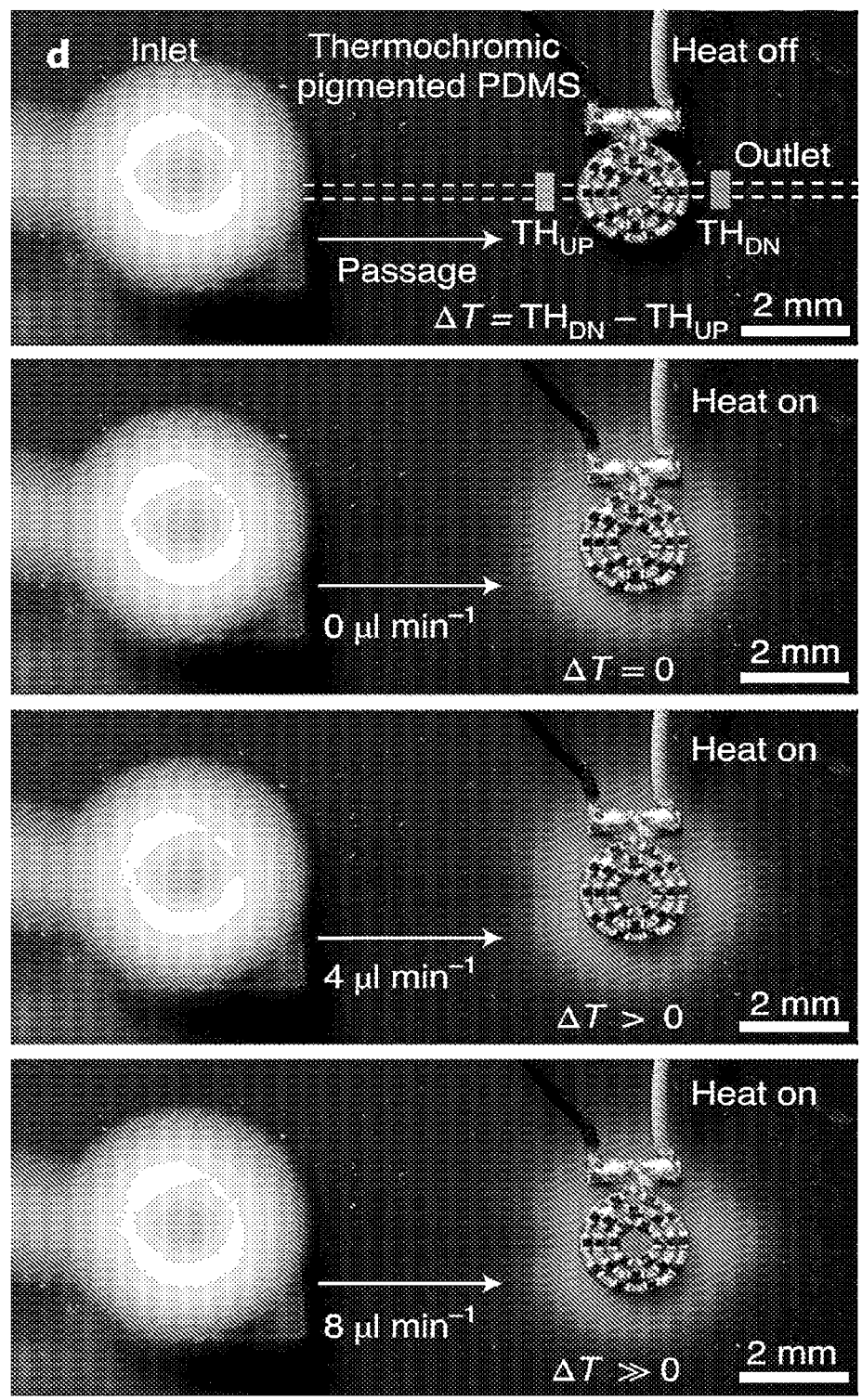

To illustrate and visualize the thermal physics, FIG. 1D shows images of a test structure formed in poly(dimethylsiloxane) (PDMS) mixed with a thermochromic powder (LCR Hallcrest) that changes in color from black to pink at a temperature above 25° C., for the cases of heat off/flow at 0 µL·min$^{-1}$, heat on/flow at 0 µL·min$^{-1}$, heat on/flow at 4 µL·min$^{-1}$ and heat on/flow at 8 µL·min$^{-1}$ from top to bottom. In this example, continuous flow of water from an inlet on the left (white circle) through a fluid passage (dashed lines) to the right introduces a corresponding skew in the shape of the pink region. The geometry of the thermal actuator and sensors, along with the dimensions of the passage and the thermal properties of the constituent materials, all affect the sensitivity of the measurement, as defined in detail in the following section.

Thermal Physics Associated with Flow Sensors

Computational predictions and benchtop studies (e.g., FIGS. 6A-6B) serve to validate the models of thermal transport and to allow for optimized selection of design parameters.

The experimental setup and wireless electronics platform for measurements with flow rates of 0 µL·min$^{-1}$, 1 µL·min$^{-1}$, 2 µL·min$^{-1}$, 3 µL·min$^{-1}$, and 4 µL·min$^{-1}$ set using a syringe pump (NE-300, New Era) appear in FIGS. 6A-6B. The sensors and associated electronics mount on the top surface of a structure that defines a passage with inlet/outlet ports sealed to polyethylene (PE) tubing (A-M Systems, No.: 801300). A BLE SoC configured with analog front-end circuits controls power to the thermal actuator and transmits the responses of the thermistors to a BLE-enabled smartphone, for real-time graphical display and storage of the time-dependent differences in temperature between the upstream and downstream locations. Subsequent sections and the Methods contain detailed information on these wireless systems and on the fabrication procedures.

Figure 2A:
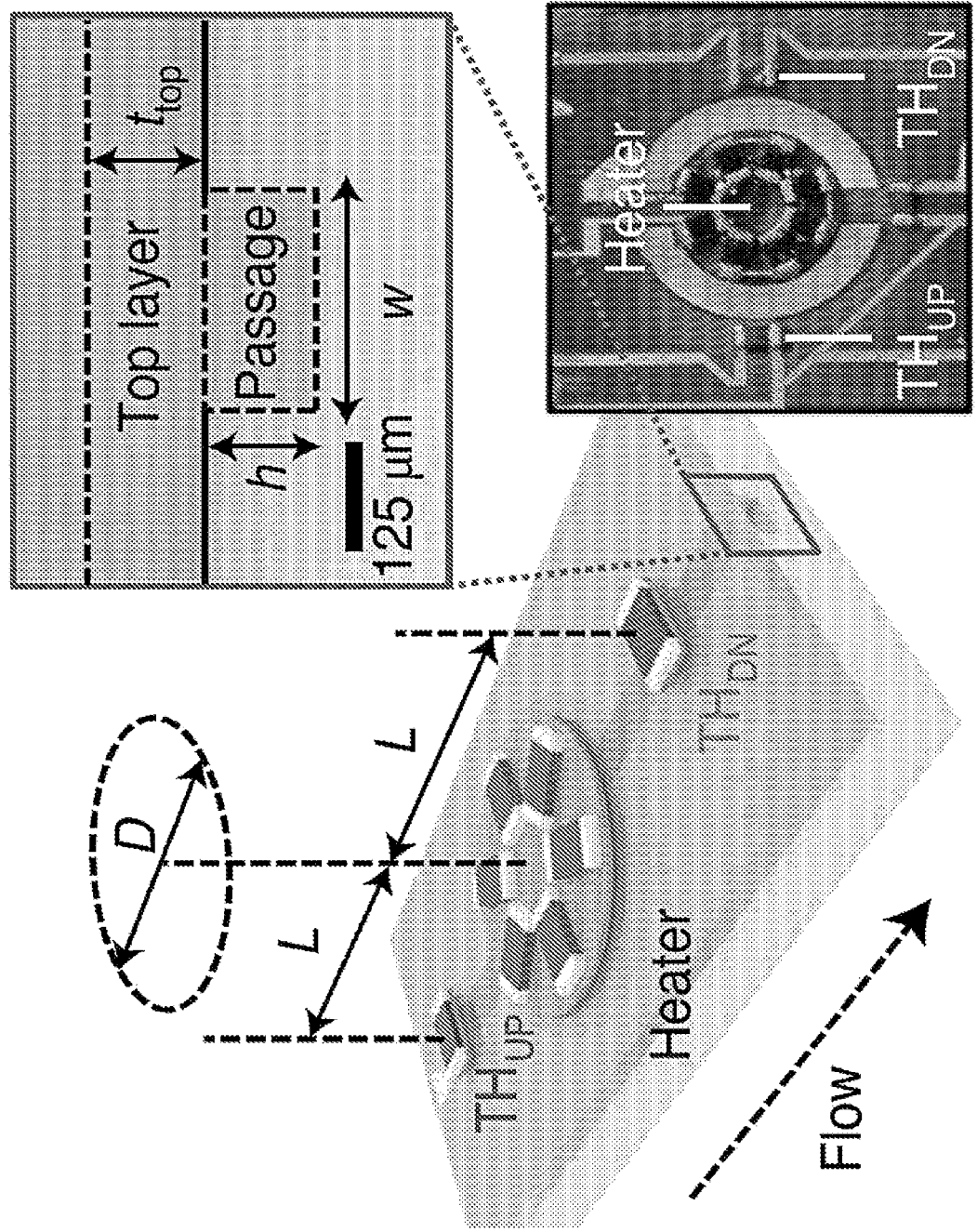
FIGS. 2A-2I show experimental studies and finite element analysis (FEA) of key characteristics of the thermal flow sensor, according embodiments of the invention.
Figure 2C:
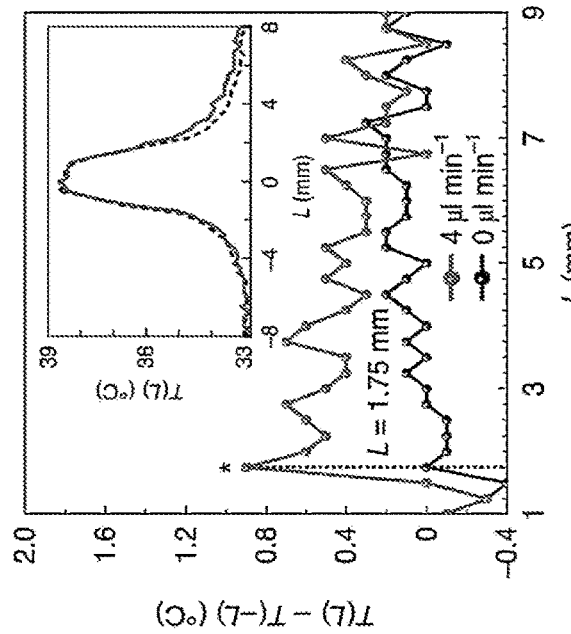
Figure 2B:
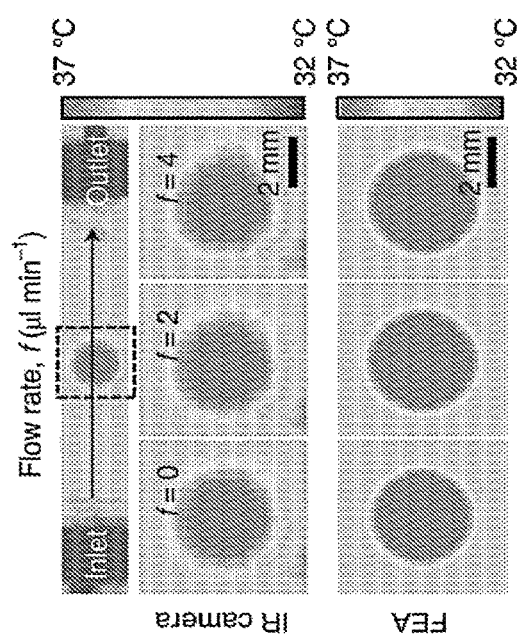

The heat transfer characteristics depend mainly on certain design parameters: the distance (L) between the center of the thermal actuator and the thermistors ($TH_{UP}$ and $TH_{DN}$), the thermal actuation power (P), the diameter of the actuator (D), and the height (h), width (w) and thickness of the top layer (hop) of the passage (FIG. 2A). The insets in FIG. 2A show a cross-sectional microscope image of a passage (top) and a picture of a heater and radially equidistant thermistors (bottom). FIG. 2B features infrared (IR) images (top) and FEA results (bottom) of anisotropic temperature distributions aligned to the direction of flow at rates (f) of 0 µL·min$^{-1}$, 2 µL·min$^{-1}$, and 4 µL·min$^{-1}$ (from left to right). Here, the thermal actuator (D=2 mm, P=28 mW) and associated thermistors mount on the surface of a structure (w×h=500 µm×125 µm, $t_{top}$=70 µm) that rests on a hot plate at a surface temperature ($T_s$) of 34° C., comparable to that of skin under ambient conditions. The IR camera (FLIR Systems, a6255sc) captures the temperature profiles, T(L), across the heater located at L=0, where L ranges from −8 mm to 8 mm along the direction of flow (FIG. 2C).

Figure 2E:
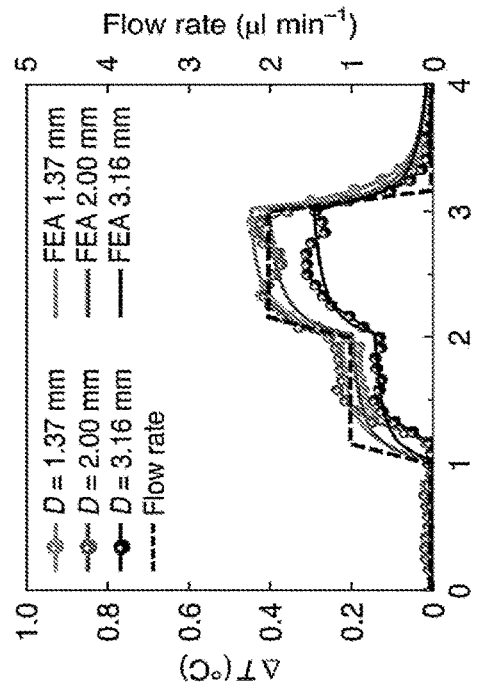
Figure 2D:
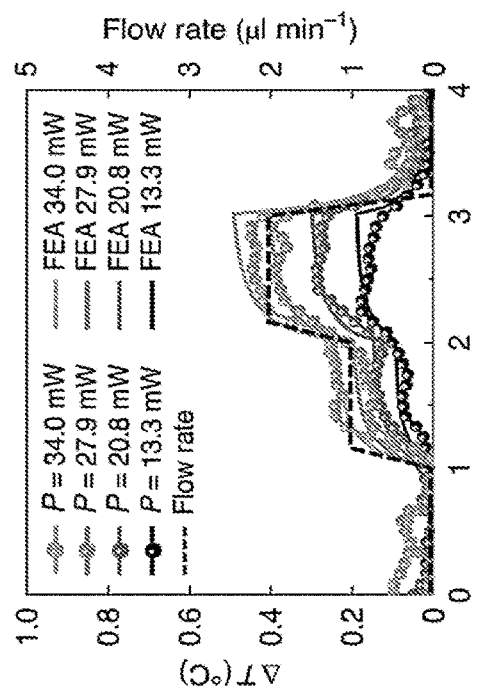
Figure 2F:
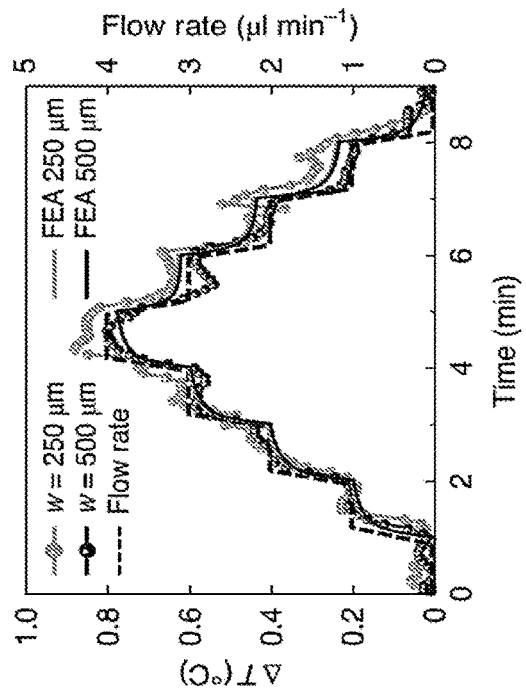
Figure 2G:
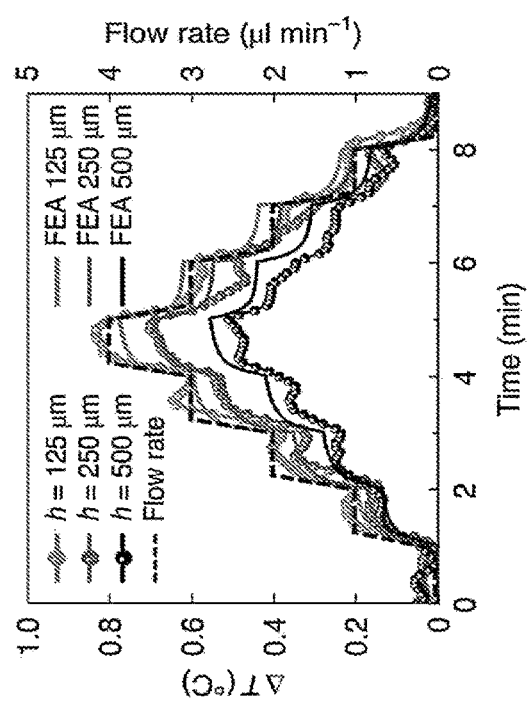
Figure 2I:
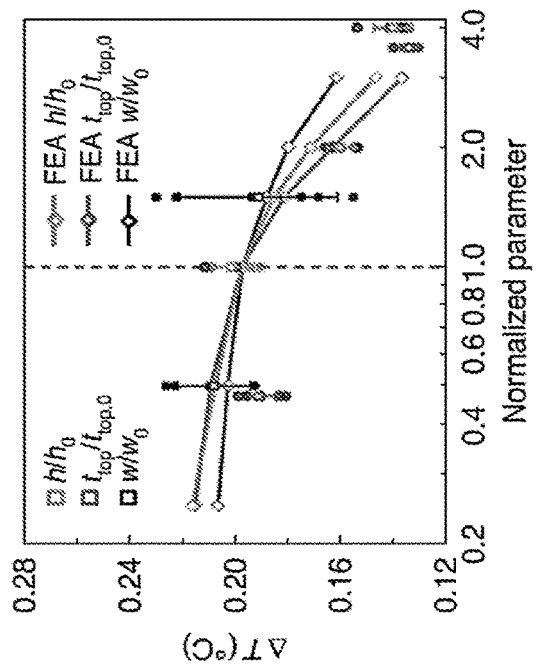
Figure 2H:
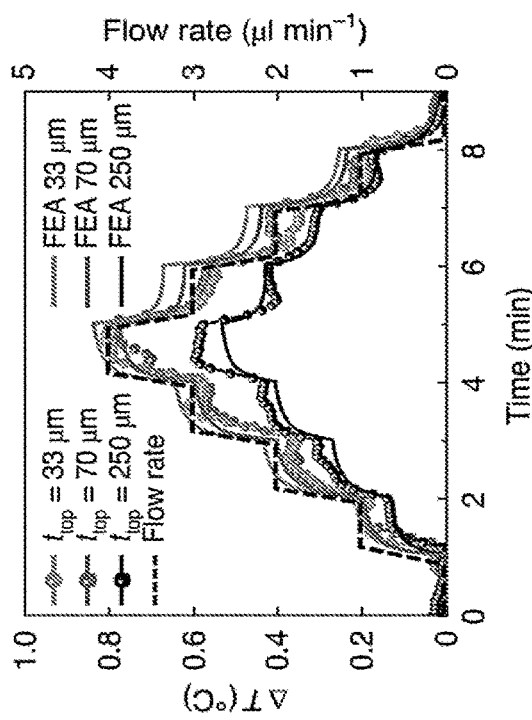
Figure 7:
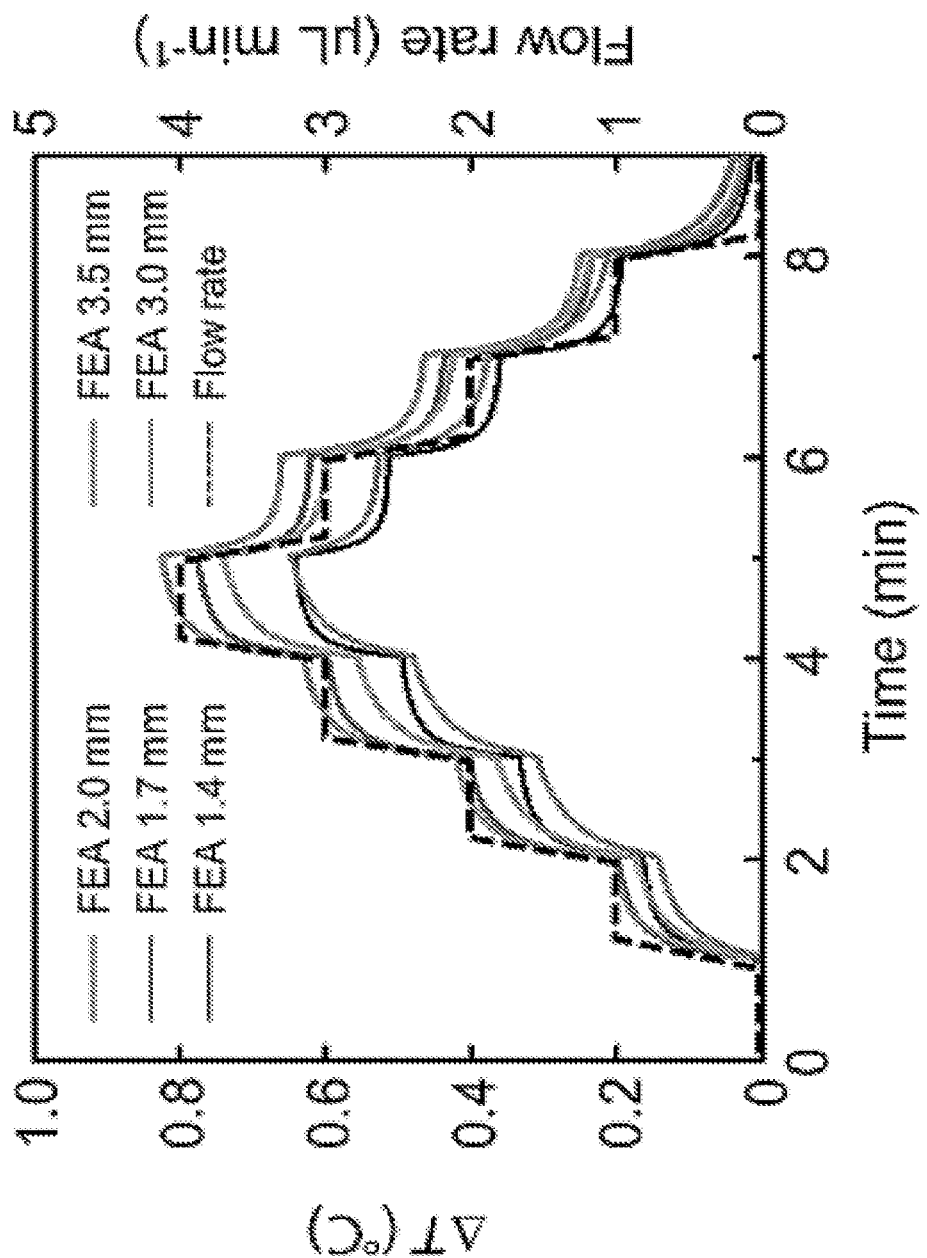
FIG. 7 shows the temperature difference (ΔT) determined by FEA for flow rates of 0 µL·min$^{-1}$, 1 µL·min$^{-1}$, 2 µL·min$^{-1}$, 3 µL·min$^{-1}$, and 4 µL·min$^{-1}$ at different L values of 1.4 mm, 1.7 mm, 2.0 mm, 3.0 mm, and 3.5 mm, according embodiments of the invention.

The profile (inset) is symmetrical with respect to the heater located L=0 for f=0 µL min$^{-1}$ (black dashed line) and skews toward the downstream direction (+L direction) at f=4 µL·min$^{-1}$ (blue line). The temperature difference, T(L)−T(−L)=ΔT for L ranging from 1.00 mm to 9.00 mm (with increments by 0.25 mm) has a small value (about 0.0° C.) for the flow rate f=0 µL·min$^{-1}$, and reaches a maximum (about 0.9° C.) at L=1.75 mm for f=4 µL·min$^{-1}$. The values of ΔT determined by FEA for f=0, 1, 2, 3 and 4 µL·min$^{-1}$ at five different L values of 1.4, 1.7, 2.0, 3.0 and 3.5 mm, are in FIG. 7. Increasing the thermal actuation power (P) or the power density ($P_d$=P/πD$^2$) increases ΔT for a constant flow rate (ΔT/f) but also increases the current consumption and therefore decreases the battery life. For L=1.75 mm, FIGS. 2D-2E show wireless measurements (symbols) and FEA results (line) for ΔT, for P=13.3, 20.8, 27.9 and 34.0 mW, and D=1.37, 2 and 3.16 mm, respectively. The black dashed line highlights changes in flow rate. The value of ΔT/f increases with increasing P or $P_d$, and the values of ΔT/f (with f=1 and 2 µL·min$^{-1}$, and P=13.3, 20.8, 27.9 and 34.0 mW) are constant as 7.1±0.1° C./µL·min$^{-1}$/W (FEA results) and 6.8±0.8° C./µL·min$^{-1}$/W (wireless measurements). Selection of P=27.9 mW and D=2 mm yields a sensitivity of 0.2° C./(µL·min$^{-1}$) with a top surface temperature of the thermal actuator that remains less than 40° C. (FIG. 2C). The data in FIGS. 2F-2H correspond to wireless measurements and FEA results for the time dependence of ΔT for changes in a flow rate with different design parameters of the fluid passage: h (FIG. 2F; w=500 µm, $t_{top}$=70 µm), (FIG. 2G; h=125 µm, $t_{top}$=70 µm), $t_{top}$ (FIG. 2H; w×h=500 um×125 um). FIG. 2I shows measurements and FEA results for ΔT for a constant flow of 1 µL·min$^{-1}$ as a function of normalized design parameters: h/$h_0$, $t_{top}$/$t_{top,0}$, where $h_0$, $w_0$, and $t_{Top,0}$ are 125 µm, 500 µm, and 70 µm, respectively. Decreasing h or $t_{top}$ corresponds to increasing the flow velocity, v=flow (f)/cross sectional area of the fluid passage (w×h) for a given f, or the heat flux between the heating elements/sensors and the flowing fluid, respectively. The result increases ΔT for a constant flow of f=1 µL·min$^{-1}$. Because decreasing w increases the flow velocity but decreases the heat flux, this parameter has a relatively small effect on sensitivity.

Additional studies focus on the reliability of the measurement under various conditions relevant to practical use, i.e., different temperature conditions, levels of airflow and mechanical vibrations, and use over extended periods (1 h) during gradual changes in flow ranging from 0 to 2 µl min$^{-1}$, as shown in FIGS. 8A-10B, which are described below.

Figures 8A, 8B:
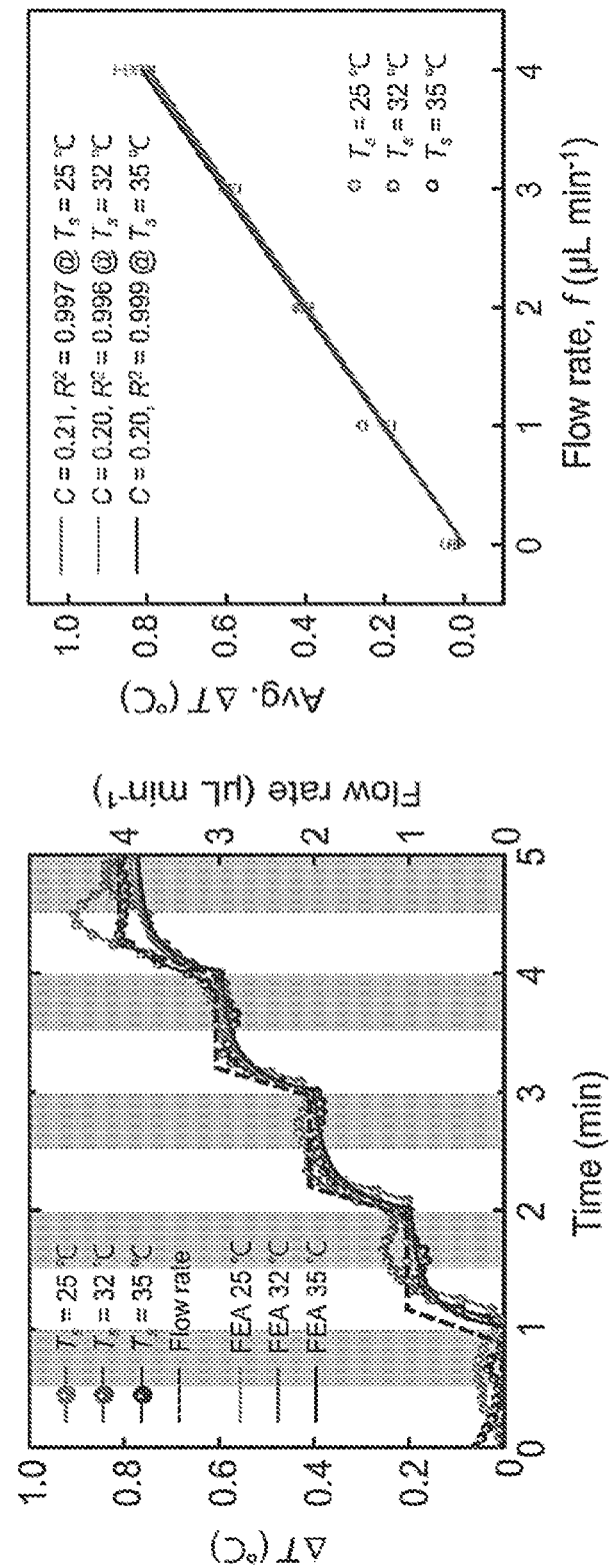
FIGS. 8A-8B show respectively measurements and FEA predictions of ΔT, and the mean and root-mean square (RMS) values of ΔT, according embodiments of the invention.

Different temperature conditions: FIG. 8A shows the measured ΔT from a device mounted on a hot plate with different temperature settings ($T_s$; from 25° C. to 35° C.). The flow rate increases from 0 µL min$^{-1}$ to 4 µL min$^{-1}$ by 1 µL min$^{-1}$ every 1 min. FIG. 8B shows the mean (circle) and root-mean square (RMS; vertical error bar) values of ΔT averaged during the last 30 s for each flow rate. At different temperatures (from 25° C. to 35° C.), measurements of ΔT for five flow rates are listed in Table 1. For $T_s$=25° C., 32° C., and 35° C., the calibration factor (C) of the measured ratio of ΔT to f is C=ΔT/f=0.21° C./µL min$^{-1}$ ($R^2$=0.997), 0.20° C./µL min$^{-1}$ ($R^2$=0.996), and, 0.20° C./µL min$^{-1}$ ($R^2$=0.999), respectively, resulting in mean values of $C_{mean}$=0.20° C./µL min$^{-1}$ and RMS values of $C_{RMS}$=0.01° C./µL min$^{-1}$.

TABLE 1

The mean ΔT for each case of f = 0, 1, 2, 3, and 4 µL·min$^{-1}$, at different temperature (25, 32, and 35° C.)

| | ΔT at 30 s averaging window | | |
|---|---|---|---|
| Flow rate (f) | $T_s$ = 25° C. | $T_s$ = 32° C. | $T_s$ = 35° C. |
| 0 | 0.05 | 0.02 | 0.03 |
| 1 | 0.20 | 0.26 | 0.19 |

TABLE 1-continued

The mean ΔT for each case of f = 0, 1, 2, 3, and 4 μL · min$^{-1}$, at different temperature (25, 32, and 35° C.)

| | ΔT at 30 s averaging window | | |
|---|---|---|---|
| Flow rate (f) | $T_s$ = 25° C. | $T_s$ = 32° C. | $T_s$ = 35° C. |
| 2 | 0.42 | 0.41 | 0.39 |
| 3 | 0.61 | 0.59 | 0.58 |
| 4 | 0.85 | 0.82 | 0.80 |

Figure 9:
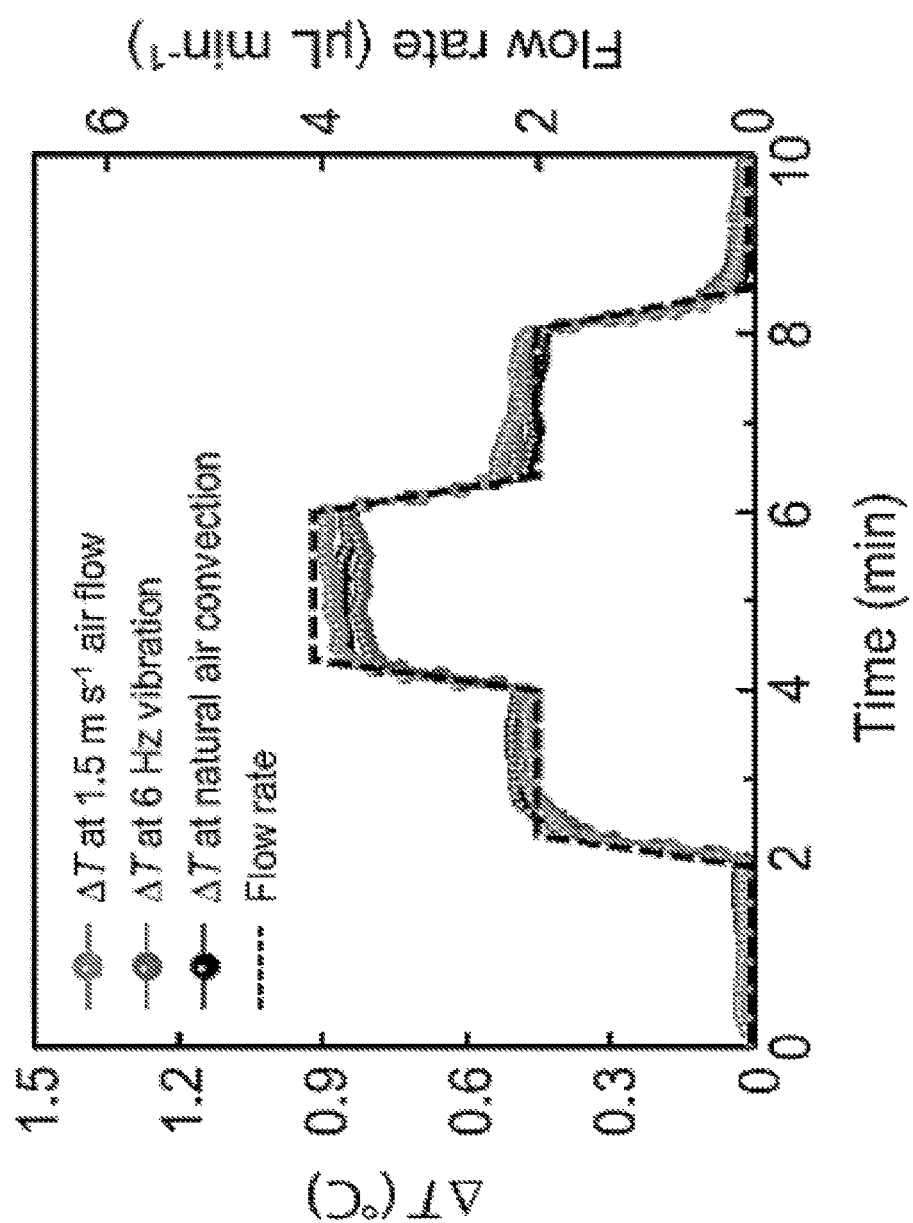
FIG. 9 shows measurements of ΔT at natural air convection (black), in airflow rates of 1.5 m/s from the top (red), and mechanical oscillations at 5 Hz with an amplitude of 2 mm (blue) for flow rates of 0 µL·min$^{-1}$, 2 µL·min$^{-1}$, and 4 µL·min$^{-1}$, according embodiments of the invention.

Different levels of airflow and mechanical vibrations: FIG. 9 shows ΔT measured in natural air convection, in airflow rates of 1.5 m/s from the top, and during mechanical oscillations at 5 Hz with an amplitude of 2 mm in the presence of flow (f=2 μL min$^{-1}$ and 4 μL min$^{-1}$). Measurements of ΔT for each case yield nearly the same signal-to-noise ratio (SNR), SNR (dB)=20×log10(ΔT$_{mean}$/ΔT$_{RMS}$)=42 dB, 40 dB, and 42 dB, respectively, as listed in Table. 2. The results indicate that the signals are typically >100 times larger than the noise.

TABLE 2

Signal-to-noise ratio (SNR) in the presence of flow (f = 2 and 4 μL · min$^{-1}$) at natural air convection, in airflow rates of 1.5 m/s from the top, and mechanical oscillations at 5 Hz with an amplitude of 2 mm.

| | Natural convection | 1.5 m s$^{-1}$ air flow | 6 Hz oscillation |
|---|---|---|---|
| 2 | 43 | 38 | 46 |
| 4 | 41 | 42 | 39 |
| Avg. SNR (dB) | 42 | 40 | 42 |

Use over extended periods during gradual changes in flow: FIG. 10A shows ΔT measured for 1 h under 20 replications of gradual changes in flow from 0 μL min$^{-1}$ to 2 μL min$^{-1}$. The mean RMS values of ΔT over 20-time measurements for f=0 μL min$^{-1}$, 1 μL min$^{-1}$ and 2 μL min$^{-1}$ are ΔT$_{mean}$±ΔT$_{RMS}$=0.04±0.02° C., 0.21±0.02° C., and 0.40±0.02° C., respectively (FIG. 10B, top). The calibration factor (FIG. 10B, bottom) has a mean value of C$_{mean}$=0.20° C./μL min$^{-1}$ and an RMS value of C$_{RMS}$=0.01° C./μL·min$^{-1}$.

The results indicate stable operation across 10° C. changes in temperature, airflow rates of 1.5 m s$^{-1}$ from the top, mechanical oscillations at 5 Hz with an amplitude of 2 mm, and for 1 h of testing. Results of field testing with volunteers, as described subsequently, confirm that the operation is stable under a range of practical conditions.

Figure 11B:
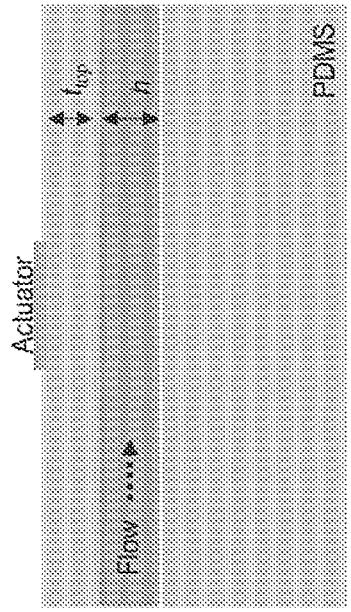
FIGS. 11A-11B show schematic illustrations of geometric modeling parameters for FEA modeling, according embodiments of the invention.
Figure 11A:
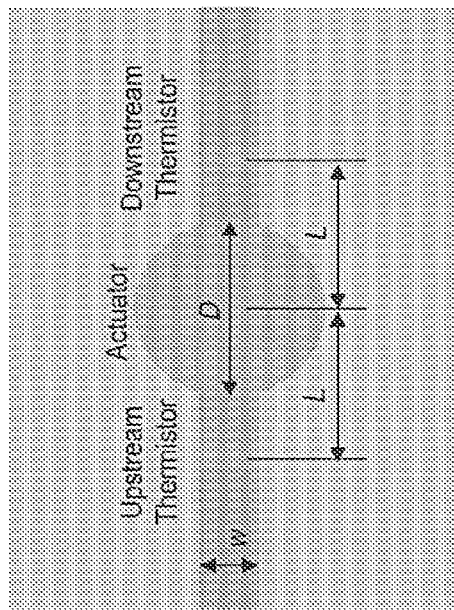
Figure 12:
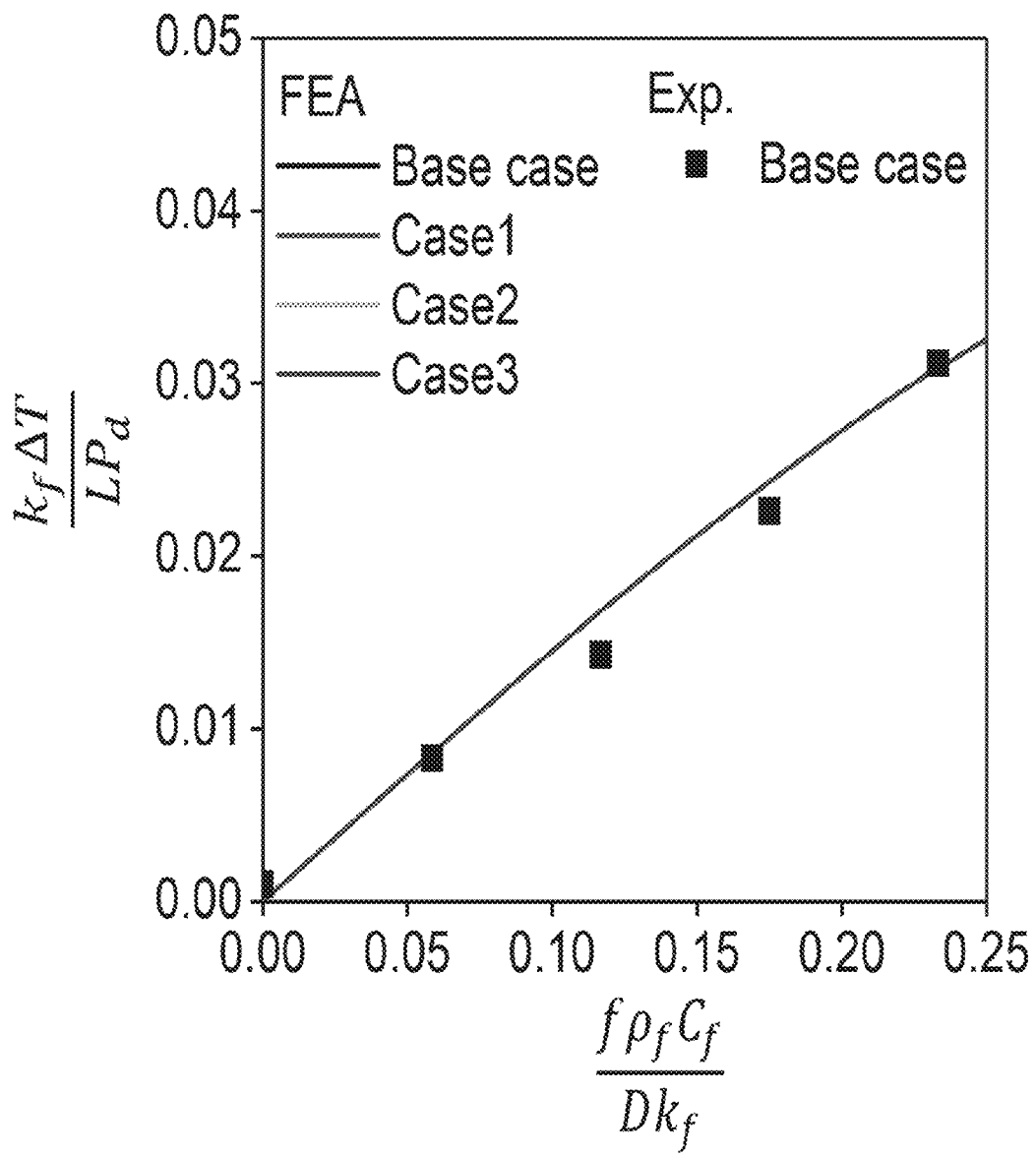
FIG. 12 shows the relationship between normalized temperature difference and normalized flow rate Parameters for the base case are summarized in Table 3. Case 1 corresponds to doubling the power density. Case 2 corresponds to doubling the thermal conductivity. Case 3 corresponds to doubling the geometric parameters (L, D, w, h and $t_{top}$ in Table 3). All results confirm the linear relationship between normalized temperature difference and normalized flow rate in the steady-state scaling law.

Variables that influence the temperature difference (ΔT), in addition to the sweat flow rate f, include thermal conductivity k, heat capacity c, and density p of the fluid (subscript "F") and the solid PDMS passage (subscript "p"), as well as the geometric parameters of the device (w, h, t$_{top}$, D and L) and the power density of the actuator (P$_d$) (FIGS. 11A-11B and Table 3).

TABLE 3

Parameters for the base case

| Parameters | unit | Values for base case | Description |
|---|---|---|---|
| D | mm | 2 | Diameter of the actuator |
| L | mm | 1.7 | Distance between the actuator and the sensor |
| t$_{top}$ | mm | 0.07 | Thickness of the top layer PDMS |
| w | mm | 0.5 | Width of the channel |
| h | mm | 0.125 | Height of the channel |
| k$_p$ | mW · mm$^{-1}$ · K$^{-1}$ | 0.27 | Thermal conductivity of PDMS passage |
| k$_F$ | mW · mm$^{-1}$ · K$^{-1}$ | 0.6 | Thermal conductivity of fluid |
| ρ$_F$c$_F$ | mJ · mm$^{-3}$ · K$^{-1}$ | 4.2 | ρ$_F$ and c$_F$ ensity and specific heat capacity of fluid |
| P$_d$ | mW · mm$^{-2}$ | 9 | Power density on the actuator |

Combining steady-state heat transfer equations and FEA, as disclosed below, (FIGS. 12A-12B and 13A-13C), a linear analytical scaling law can be obtained between the normalized temperature difference $$\frac{k_F \Delta T}{L P_d}$$

and the normalized flow rate $$\frac{f \rho_F c_F}{D k_F}.$$

Under steady state, heat transfer can be expressed as $$\Delta^2 T = 0 \text{ in the solid,}$$

$$k_F \Delta^2 T = \rho_F c_F v \cdot \Delta T \text{ in the fluid.}$$

Additionally, T$_F$=T$_p$ and k$_F$T$_F$=k$_p$ T$_p$ at the interface between the solid and the fluid, corresponding to continuity of the temperature and the temperature gradient at the interface. It is noted that ρ$_F$c$_F$ does not influence the temperature distribution under steady-state heat transfer. Hence, the steady-state scaling law can be given by $$\frac{k_F \Delta T}{L P_d} = k\left(\frac{f \rho_F c_F}{D k_F}, \frac{L}{D}, \frac{h}{D}, \frac{w}{D}, \frac{t_{top}}{k}, \frac{k_p}{k_F}\right),$$

where ΔT is the temperature difference between upstream and downstream sensors, f is the flow rate; w and h are the channel width and the channel height, $t_{top}$ is the top thickness of the channel, D is the actuator diameter, L is the sensor distance; and k is the thermal conductivity, c is the heat capacity, p is the density with subscript "F" for the fluid and subscript "p" for PDMS passage; and power density of the actuator ($P_d$). According to FEA results shown in FIGS. 12A-12B, 13A-13C and 14A-14C, at flow rates from 0 to 4 µL·min⁻¹, the normalized temperature difference increases linearly with the normalized flow rate. Therefore, the steady-state scaling becomes $$\frac{k_F \Delta T}{L P_F} = \frac{f \rho_F c_F}{D k_F} g\left(\frac{L}{D}, \frac{h}{D}, \frac{w}{D}, \frac{t_{top}}{k}, \frac{k_p}{k_F}\right).$$

Figures 13A, 13B:
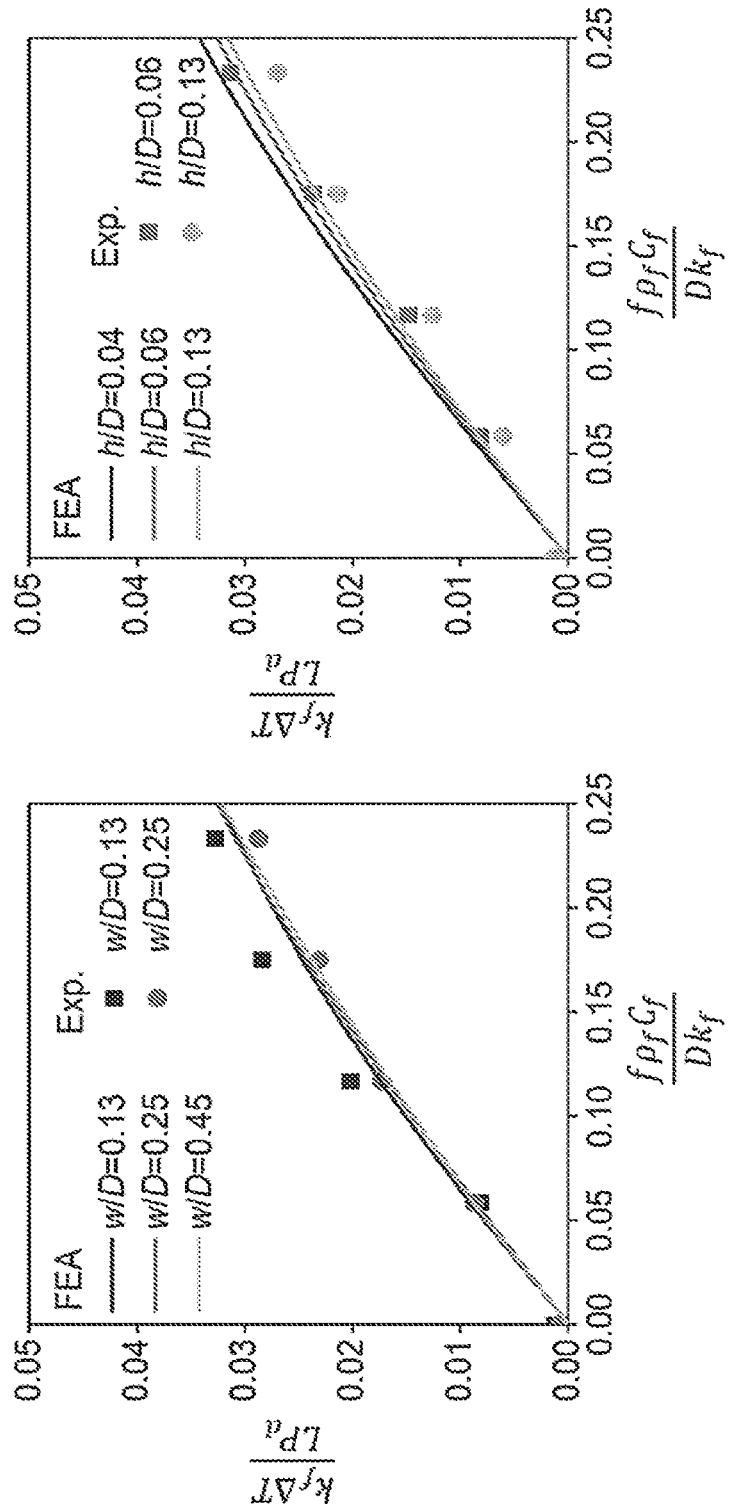
FIGS. 13A-13B show respectively effect of the normalized geometric parameters w/D (FIG. 13A) and h/D (FIG. 13B) in the scaling law, according embodiments of the invention. As w/D increases from 0.1 to 0.45 the normalized temperature difference remains almost the same. As h/D increases from 0.04 to 0.1, the normalized temperature differences are similar (about 6%). Hence, the effect of the normalized channel width can be ignored in the scaling law. (Parameters for the base case: D=2 mm, L=1.7 mm, w=0.5 mm, h=0.125 mm, $t_{top}$=0.07 mm, =8.9 mW·mm$^{-2}$, $k_s$=0.6 mW·mm-1·K-1, $ρ_s c_s$=4.17 mW·mm-1·K-1, $k_{PDMS}$=0.27 mw·mm$^{-1}$·K$^{-1}$).
Figure 19B:
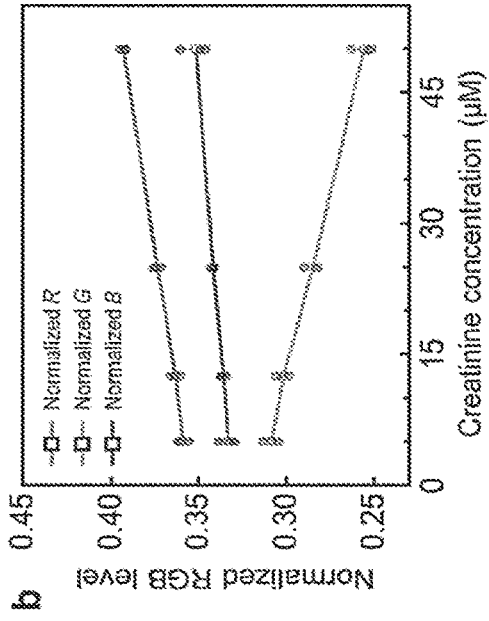
FIGS. 19A-19D show color levels of assay µ-RVs as a function of sample concentrations: chloride (FIG. 19A), creatinine FIG. 19B), Glucose (FIG. 19C), and pH (FIG. 19D), according embodiments of the invention. Data are presented as mean values±SD (sample size=3).
Figure 19A:
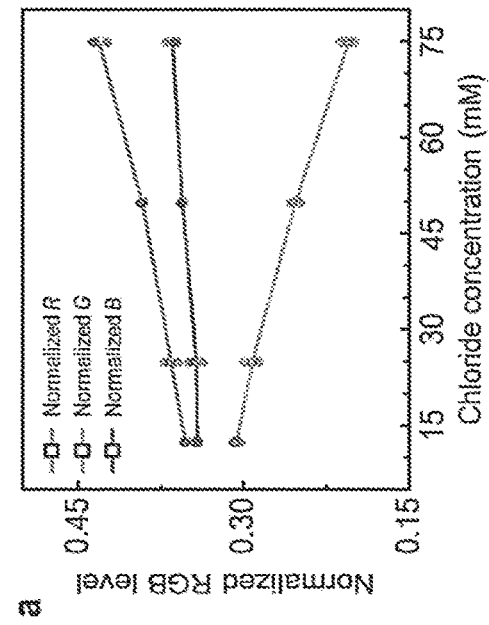
Figure 19D:
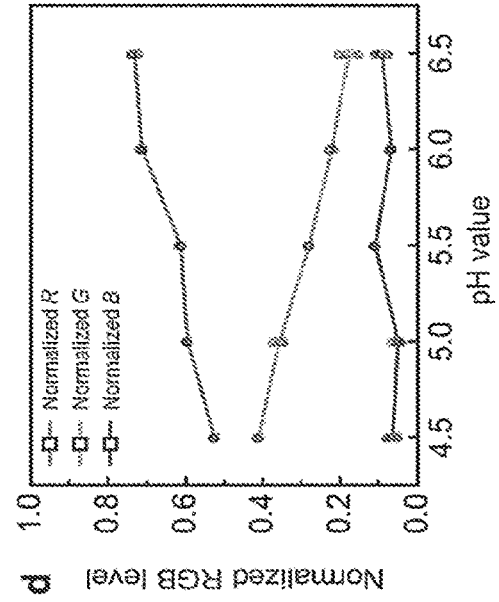
Figure 19C:
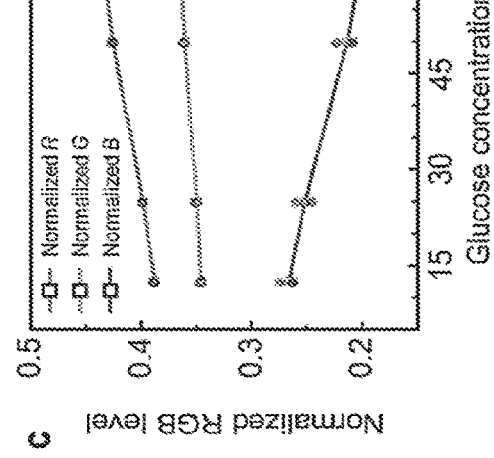

Among the four non-dimensional geometric parameters, it is found that w/D and h/D have less impact on the normalized temperature difference (FIGS. 13A-13B).

Hence, the linear analytical scaling law can be further simplified as $$\frac{k_F \Delta T}{L P_d} = \frac{f \rho_F c_F}{D k_F} g\left(\frac{L}{D}, \frac{t_{top}}{k}, \frac{k_p}{k_F}\right).$$

The function in this scaling law depends on only two non-dimensional geometric parameters and one non-dimensional thermal property: L/D and $t_{top}$/h represent the effect of heat transfer along the flow direction and the depth direction, respectively, and $k_p/k_F$, represents the effect of thermal conductivity. Reducing L/D, $h_{thp}$/h and $k_p/k_F$, can increase the device sensitivity, which is shown as the slope of the normalized temperature difference with respect to the normalized flow rate (FIGS. 14A-14C).

Circuit Designs and Operating Principles

Figure 3B:
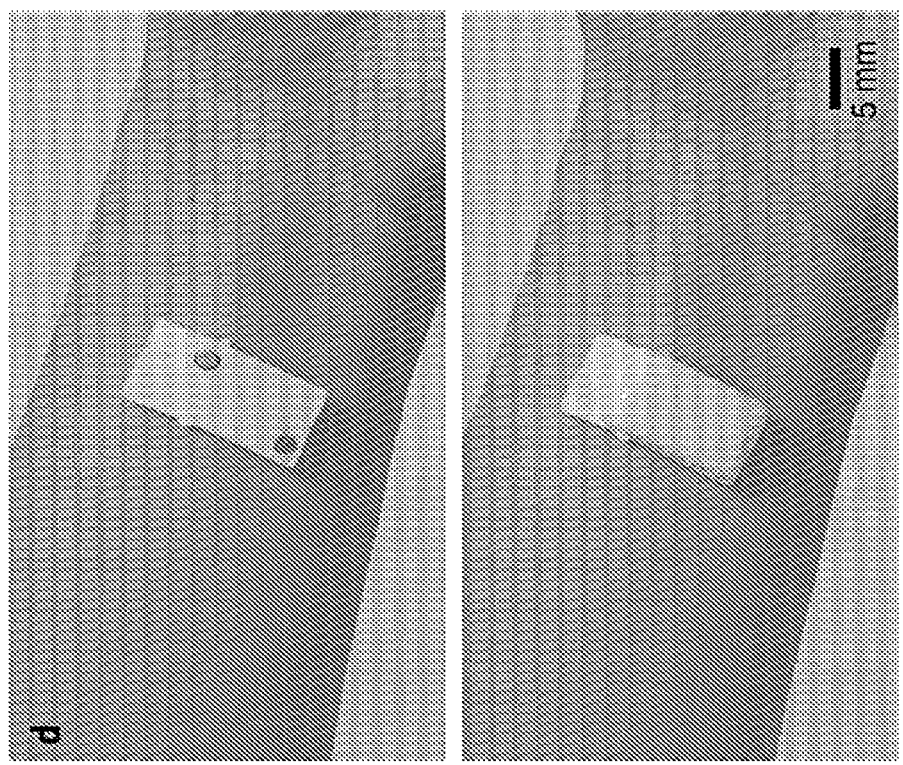
FIGS. 3A-3D show a skin-interfaced, wireless system for continuous monitoring of sweat rate, sweat loss and temperature, according embodiments of the invention.
Figure 3A:
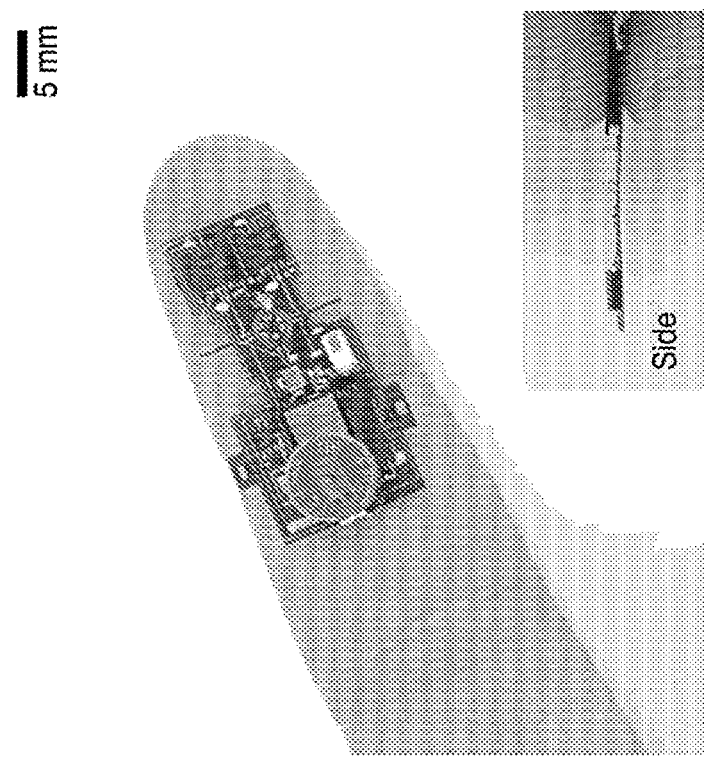
Figure 3C:
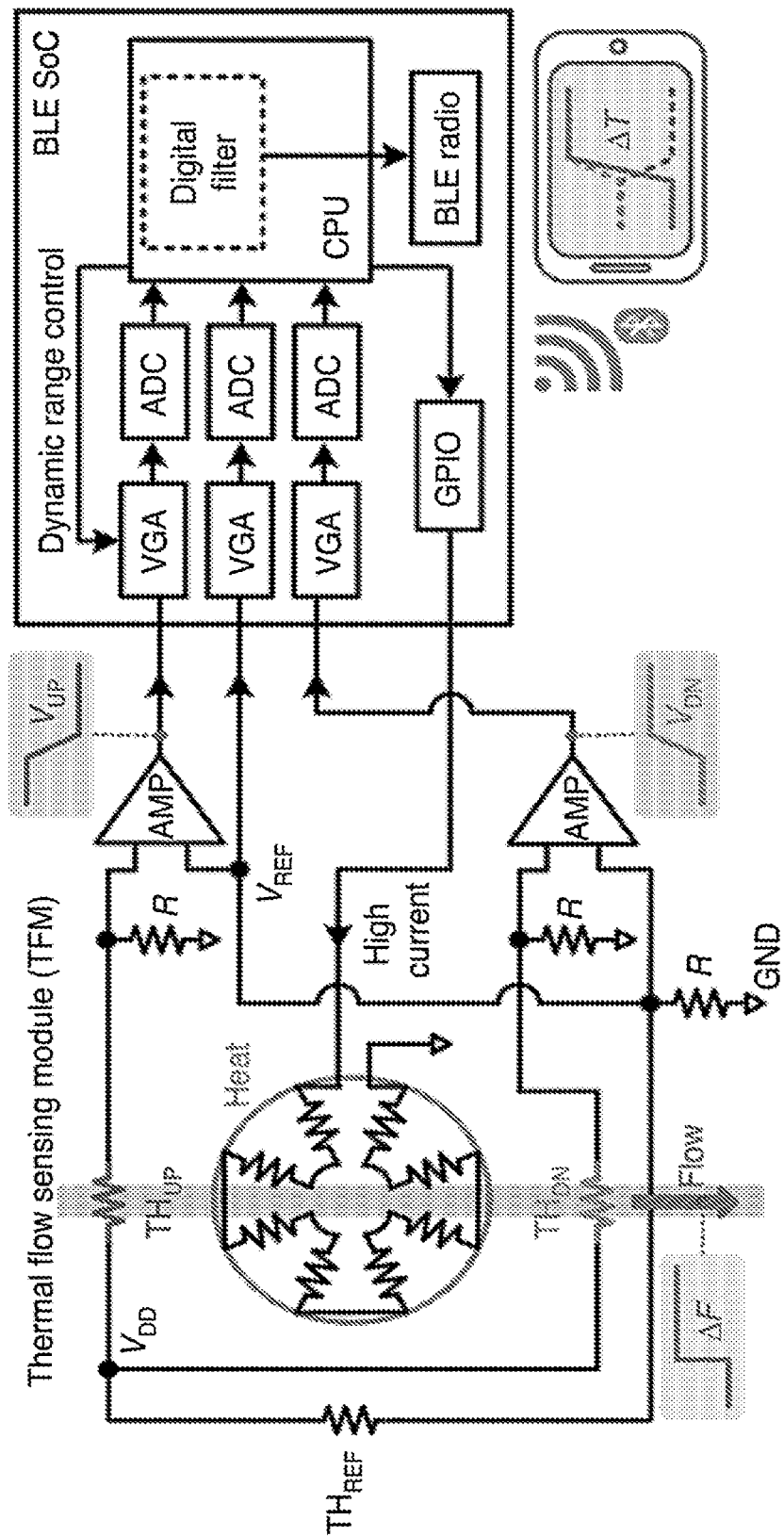

The device in FIG. 3A is a wireless, non-invasive, reusable system for continuous, real-time measurements of the flow of sweat between and an inlet and outlet, in a platform designed for real-world use and without any direct contact with sweat, based on the considerations in thermal physics and engineering design highlighted in the previous section. The width, length, height, and weight of the device, excluding a button cell battery (MS621FE), are 11.2 mm, 24.8 mm, 1.2 mm, and 203.0 mg, respectively. The inset presents a side view. The wireless platform includes a thermal flow-sensing module (TFM) and a BLE SoC for control and wireless communication (FIG. 3C). A key feature of the TFM is that it uses a reference thermistor as one leg of a Wheatstone bridge circuit followed by differential amplifiers cascaded by variable gain amplifiers (VGAs), with gain automatically controlled by the central processing unit (CPU) of the BLE SoC depending on the temperature measurements. The reference thermistor ($TH_{REF}$) resides outside the fluid passage but at the same distance from the thermal actuator as THUD and $TH_{DN}$. The changes in environmental temperature affect this $TH_{REF}$ in the same manner as the other thermistors, thereby naturally eliminating the effects of these changes (for example, due to variations in the skin and/or the surrounding air). A VGA, subsequent to the Wheatstone-bridge circuit, amplifies the voltage outputs from the bridge, with an adaptive gain (for example, from 1/6 to 4) to maximize the accuracy of the measurements of resistance (for example, from 0.22 0 to 0.01 Q) within the required dynamic range.

Standard resistive sensing modules include, by contrast, a Wheatstone bridge circuit that incorporates a reference resistor (Ro) with a fixed resistance and a differential amplifier with a fixed gain. The former measures an unknown resistance associated with a sensing element by comparing it with a known value of resistance, and the latter amplifies the differences to maximize the accuracy. Here, increasing the amplifier gain increases the accuracy (for detection of small temperature changes associated with low flow rates), but decreases the dynamic range (which leads to out-of-range conditions for large temperature changes that can arise from environmental variations or high flow rates). Even in the absence of flow, changes in environmental temperature from 25° C. to 35° C. (decreasing the resistances of the thermistors from 10.00 kΩ to 6.92 kΩ) increase the voltage outputs of the Wheatstone bridge circuits (from 0 V to 0.3V), which limits the amplifier gain (as supply voltage/0.3 V=3.3 V/0.3 V=11 V/V), and also the accuracy of the resistance measurements (as 2.20Ω). The TFM configures a reference thermistor outside the fluid passage but at the same distance from the thermal actuator as the upstream and downstream thermistors. The changes in environmental temperature affect this reference thermistor in the same manner as other thermistors, thereby naturally eliminating the effects of these changes (e.g., due to variations in the skin and/or the surrounding air). Under different environmental conditions, the voltage outputs of the Wheatstone bridge remain around 0 V, which imposes no limitation on the amplifier gain or the accuracy. A VGA, subsequent to the Wheatstone bridge circuit, amplifies the voltage outputs from the bridge, with an adaptive gain (e.g., from 1/6 to 4) to maximize the accuracy of the measurements of resistance (e.g., from 0.22Ω to 0.01Ω) within the required dynamic range. As a specific example of real-time gain adaptation, as the measured voltage increases and reaches 90% of the upper limit of dynamic range (=supply voltage/gain), the gain decreases, thereby increasing the dynamic range. As voltage decreases, the gain increases along with the accuracy.

FIG. 3C presents circuit and block diagrams of the TFM and BLE SoC for wireless communication to an external user interface (e.g., smartphone). A software toggle switch enables BLE-connection to the device and activates a general-purpose input/output (GPIO) pin to source a predetermined current (about 10 mA) into the resistive heater. As described above, the TFM includes a thermal actuator (Joule heating through 35.6 Ω×8 resistors), Wheatstone bridge circuits include three thermistors (upstream, downstream, and reference; $TH_{UP}$, $TH_{DN}$, and $TH_{REF}$) with a known resistor (R) on each bridge, and two differential amplifiers (AMPs). Each AMP amplifies the differences between the voltages on the upstream and downstream thermistors and the voltage on the reference thermistor to eliminate the effects of temperature differences due to environmental changes, as highlighted previously. The subsequent VGAs buffer the output of the AMPs to following analog-to-digital converters (ADCs). Three-channel ADCs monitor the bridge voltages on upstream ($V_{UP}$), downstream ($V_{DN}$), and reference ($V_{REF}$) values and control the gain of the VGAs prior to each ADC to achieve the highest resolution within the input voltage range. A CPU executes digital signal processing on the ADC-sampled data ($V_{UP}$, $V_{DN}$, and $V_{REF}$) to filter out noise. Wireless transmission occurs over the BLE radio to the user interface where algorithms convert the voltages into corresponding temperature values.

Figure 3D:
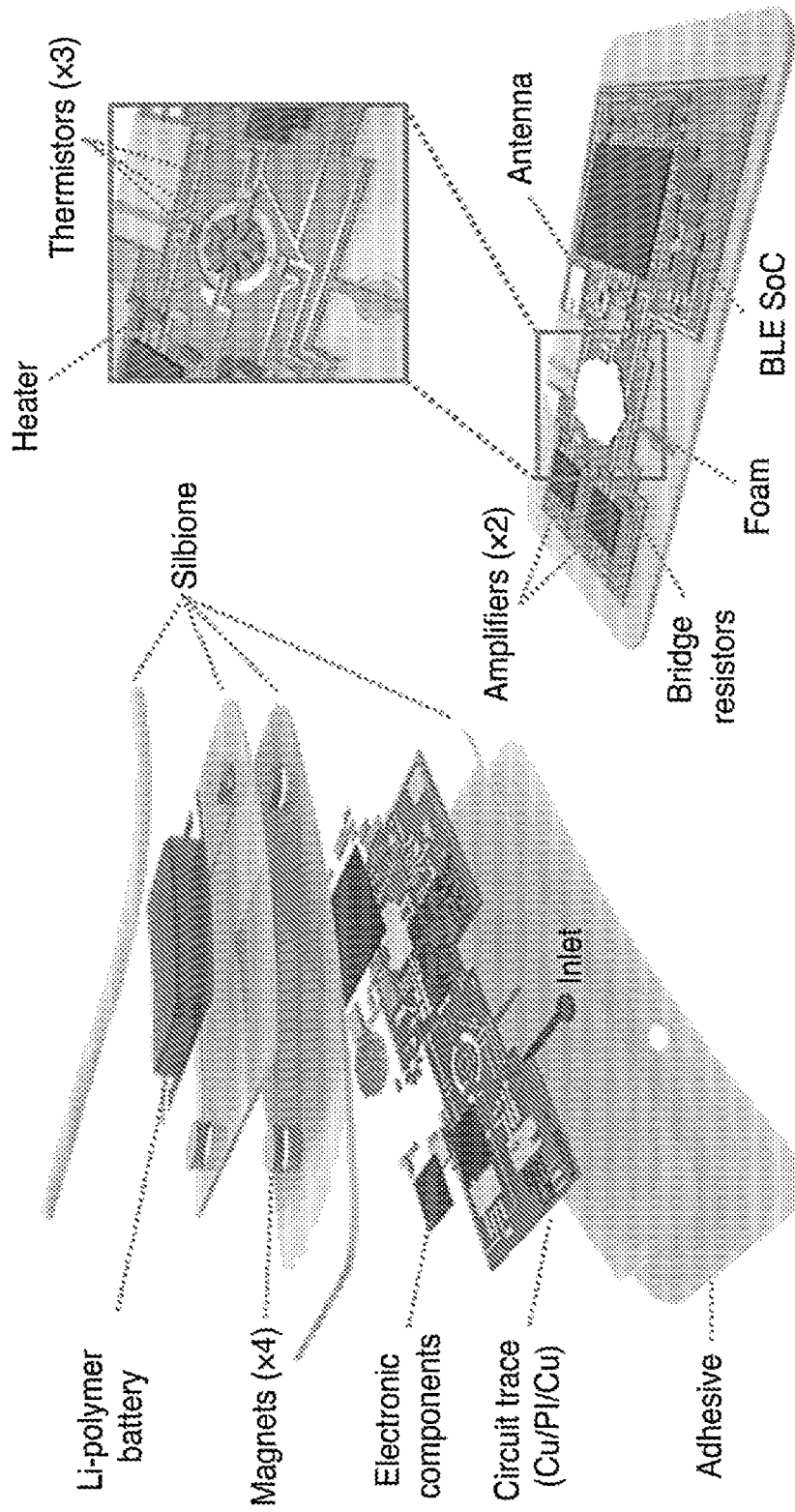

FIG. 3D provides an exploded view illustration of the constituent layers and components: silicone encapsulation layers, Li-polymer battery, mini-magnets, an insulation foam (Flex Foam), electronics, a PDMS structure to define separated inlets and outlets, and adhesives. The electronics use thin, flexible copper-clad polyimide sheets (AP8535R, Pyralux) processed with a laser cutting tool (Protolaser U4, LPKF) to yield circuit traces that interconnect the BLE SoC, amplifiers (×2), bridge resistors (×3), thermistors (×3), and thermal actuator. FIG. 3B presents a picture of an encapsulated device adhered to the skin (3M 1524) with and without an encapsulated battery mounted mechanically and electrically via matching magnets. Use for 1-h per day with flow measurements every minute and a 20% duty cycle of heating (heat on for 12 seconds before each measurement), the replaceable battery (Li-Polymer battery, GMB351223; 70 mAh) has an expected lifetime of 2 weeks.

On-Body Measurements for Physical Activity and Dehydration Monitoring

Figure 4A:
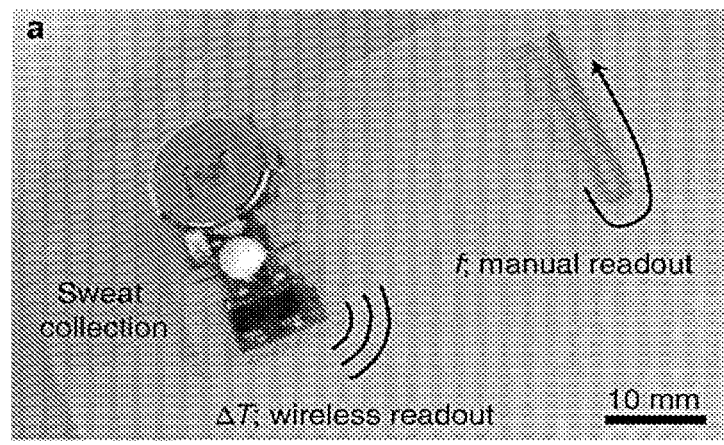
FIGS. 4A-4I show on-body measurements of sweat flow rate and total loss for physical activity and dehydration monitoring, according embodiments of the invention.
Figure 4B:
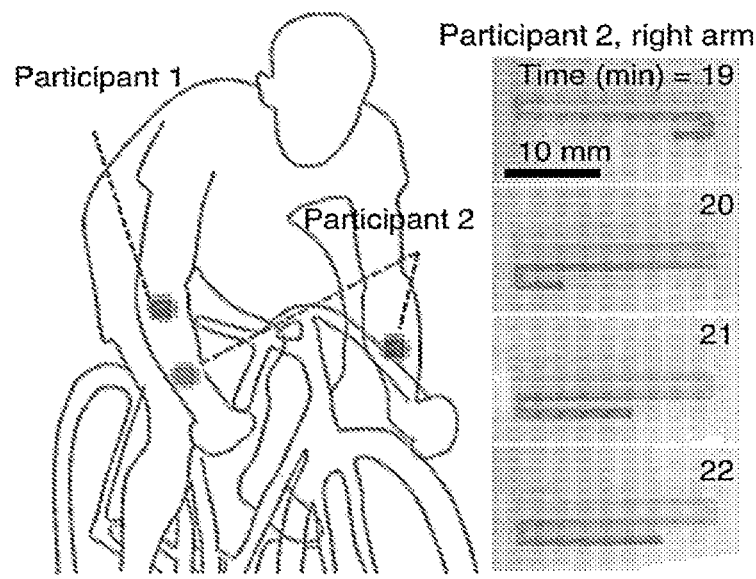
Figure 4C:
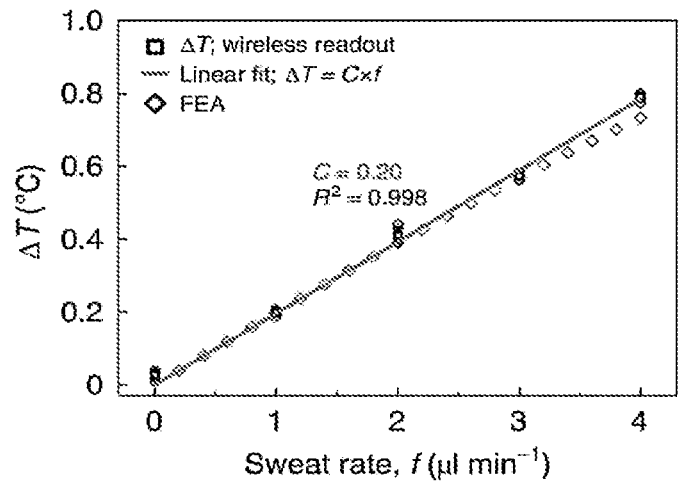

A key feature of this platform is that its operation does not rely on an elaborate microfluidic structure, but only on a short, straight flow segment between an inlet interface to the skin and an outlet to the surroundings. A photograph of a device with this simple design is presented in FIG. 4A, which is shown mounted on the forearm but with an extended configuration that also includes a serpentine microfluidic passage to allow for manual readout of sweat rate and volume as the basis for validating the flow measurements. A water-soluble dye (blue) located at the inlet of this serpentine imparts color to the incoming sweat, thereby producing an easily identifiable filling front. Studies of wireless and manual measurements of sweat rate involve the deployment of devices on the forearms of two healthy volunteers (FIG. 4B): the right forearm for subject #1, both forearms for subject #2 (left). The system performs temperature measurements at a 200-Hz sampling rate and transmits an averaged value every 0.1 seconds (10 Hz) to a user interface. Software applications save the wireless readings (10 data per second) into the memory of the smartphone and display the averaged value every minute, synchronized with manual reading of the position of the filling front by capture and analysis of digital images of the device (right, FIG. 4B). Calibration involves a constant flow of liquid (deionized water) established with a syringe pump (NE-300, New Era) over a 1-min measurement period. For flow rates (f) of 0 $\mu L \cdot min^{-1}$, 1 $\mu L \cdot min^{-1}$, 2 $\mu L \cdot min^{-1}$, 3 $\mu L \cdot min^{-1}$ and 4 $\mu L \cdot min^{-1}$, the temperature differences ($\Delta T$) are 0.03° C., 0.19° C., 0.40° C., 0.59° C., 0.81° C., respectively (FIG. 4C). As f increases, $\Delta T$ increases proportionally such that the calibration factor (C) of the measured $\Delta T$ over f is $C_{meas}=\Delta T/f=0.20°$ C./$\mu L \cdot min^{-1}$ ($R^2=0.998$). Results of FEA (diamond-shaped markers) indicate a calibration factor of 0.18° C./$\mu L \cdot min^{-1}$ ($R^2=0.997$) for a range of flow rates from 0 $\mu L \cdot min^{-1}$<f<4 $\mu L \cdot min^{-1}$. The wireless measurements (linear fit line; red line) are in good agreement (about 90%) with the FEA results.

Figure 4D:
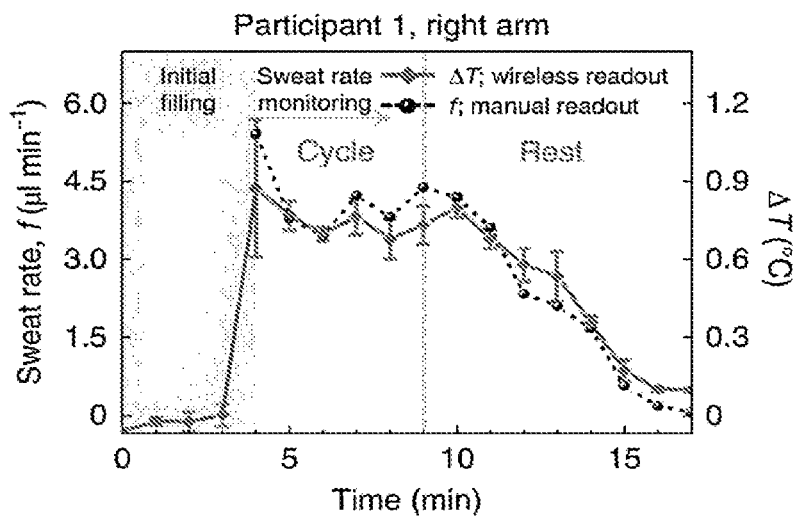
Figure 4E:
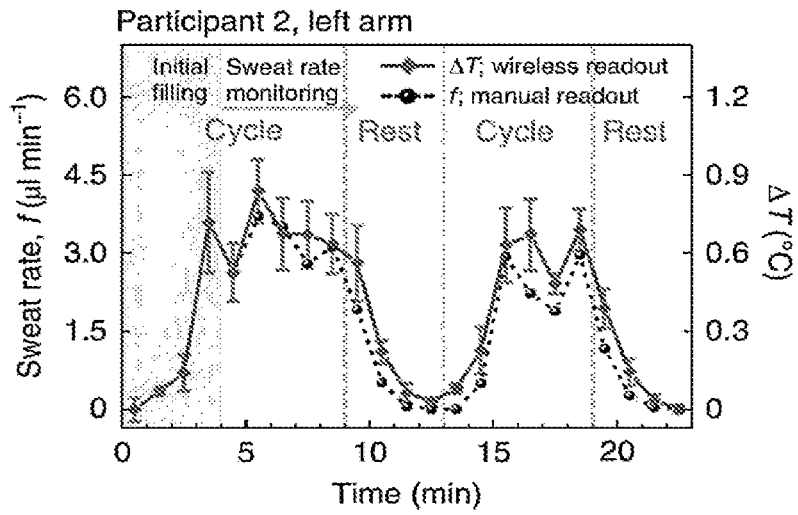
Figure 4F:
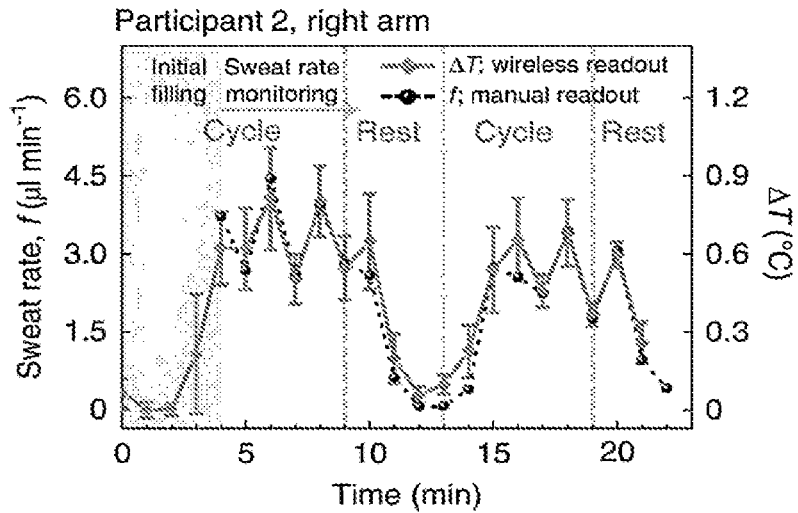
Figure 4G:
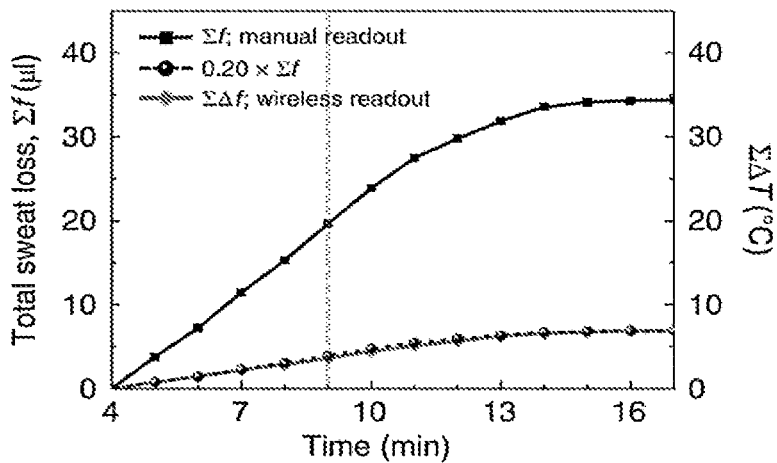
Figure 4H:
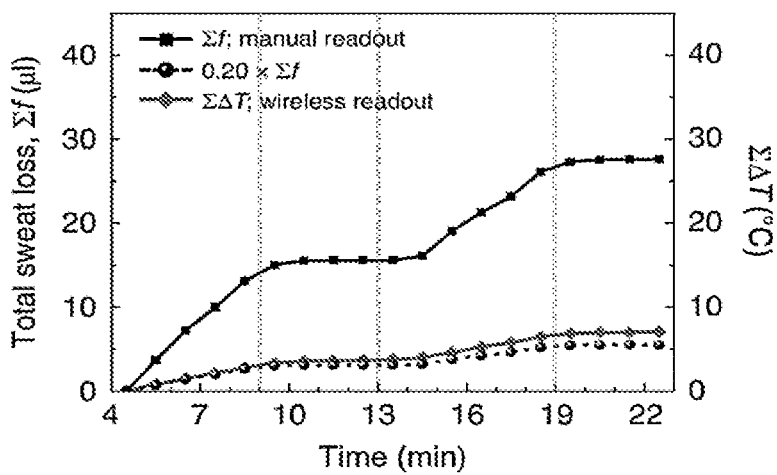
Figure 4I:
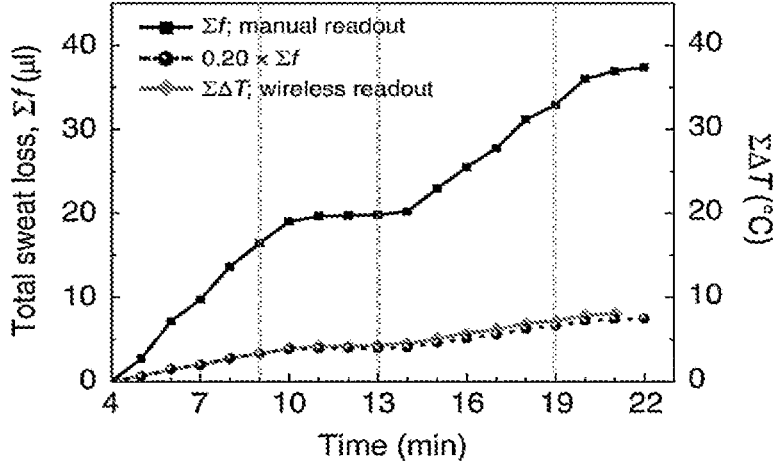

FIGS. 4D-4F show the results of manual readings off (purple, blue, and red symbols) and wireless measurements of $\Delta T$ (black markers) as a function of time (min) from the right forearm of subject #1 (FIG. 4D), and both forearms in subject #2 (FIGS. 4E-4F) while cycling and at rest. During the session labeled "Cycle", $\Delta T$ and f increase and reach a constant value, and then decrease to values approaching zero during the session labeled "Rest". The data exhibit a strong correlation between physical activity and sweat rate. Vertical error bars (gray line) on the graphs represent the standard deviation (SD) of $\Delta T$ measured over a 1-min averaging window. Errors in the flow rate, $f_e=f-\Delta T/C_{meas}$, as a function of time are summarized in FIGS. 15A-15C. Results from the right forearm of subject #1, and the left and right forearms of subject #2 have mean values of $f_{e,mean}=0.04$ $\mu L \cdot min^{-1}$, $-0.40$ $\mu L \cdot min^{-1}$, $-0.16$ $\mu L \cdot min^{-1}$, respectively, with RMS values of $f_{e,RMS}=0.48$ $\mu L \cdot min^{-1}$, 0.33 $\mu L \cdot min^{-1}$, 0.36 $\mu L \cdot min^{-1}$. FIGS. 4G-4I shows plots of cumulative $\Delta T$ (EAT; diamond markers) and local sweat loss ($\Sigma f$, square markers) as a function of time measured from the forearm of subject #1 (FIG. 4G), left (FIG. 4H) and right (FIG. 4I) forearms of subject #2. Manual readings of the collected sweat multiplied by the calibration factor ($C \times \Sigma f$, circle markers) correspond to the summed values of wireless measurements of $\Delta T$ with an average error (e) of $e=(\Sigma \Delta T/C - \Sigma f)/\Sigma f=0.13$.

Multifunctional Systems: Sweat Flow/Loss, Sweat Chemistry and Skin Temperature

Figures 5A, 5B:
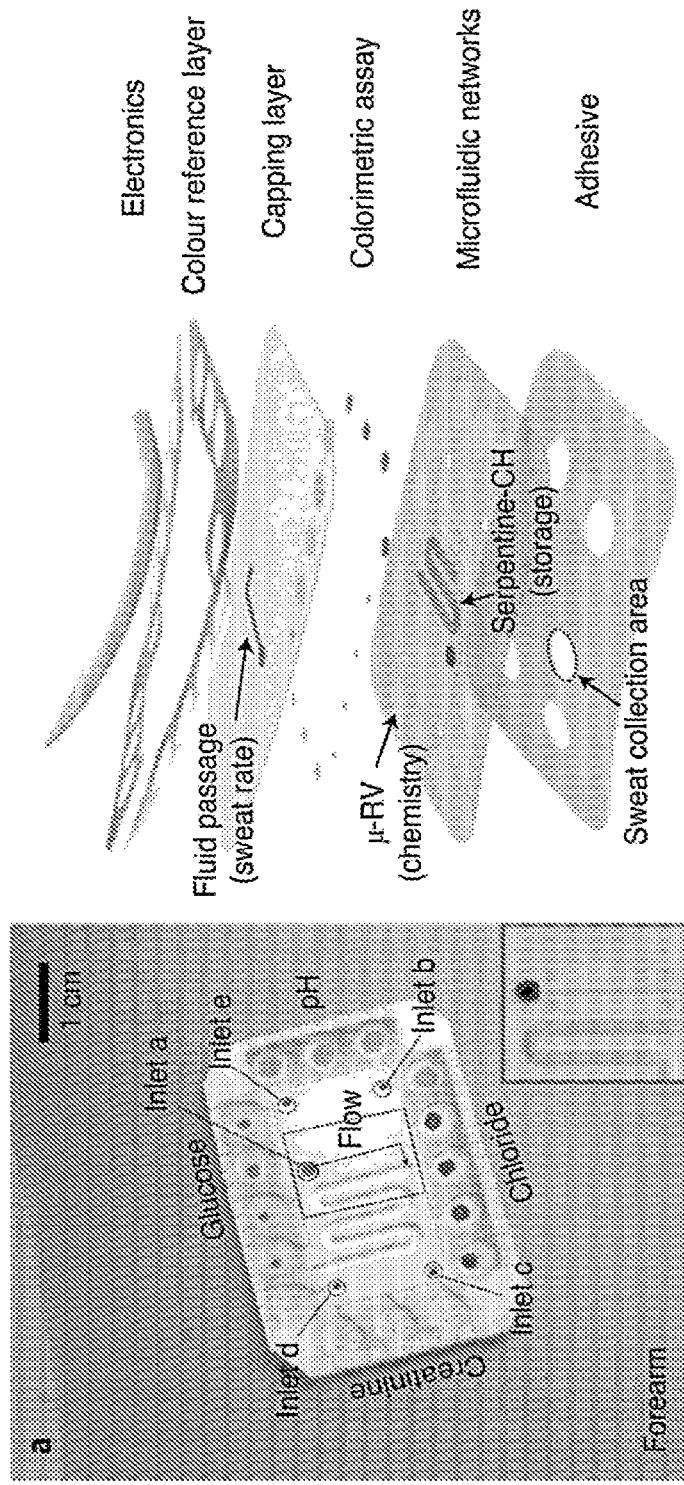
FIGS. 5A-5E show multimodal sensing of sweat rate and loss, skin temperature, and various sweat biomarkers, according embodiments of the invention.

The types of noncontact, digital wireless measurements of sweat flow rates and total sweat loss can be combined with measurements of sweat chemistry using microfluidic platforms and colorimetric chemistries and also with assessments of skin temperature using additional components in the electronics module. For the former, demonstrations focus on concentrations of chloride and glucose in sweat provide indications relevant to cystic fibrosis in newborns and infants, and diabetes, respectively. Sweat creatinine has potential as a screening marker for kidney dysfunction. The pH of sweat is an indicator of metabolic alkalosis, where the pH shows elevated values relative to the normal range (7.35-7.45) due to decreased hydrogen ion concentration and associated increased concentrations of bicarbonate. A simple platform that addresses these needs exploits corresponding colorimetric chemical reagents (pH, glucose, chloride and creatinine) loaded into a skin-interfaced microfluidic system designed to allow reversible integration with the wireless platform introduced in the previous sections. As illustrated in FIG. 5A, the system supports (1) colorimetric analysis of sweat chloride/glucose/creatinine/pH levels, as well as (2) wireless, digital evaluation of sweat rate and volume. The latter quantities are often critically important in interpreting the former, as sweat chemistry is known to depend on the sweat rate and total sweat loss.

Figure 5C:
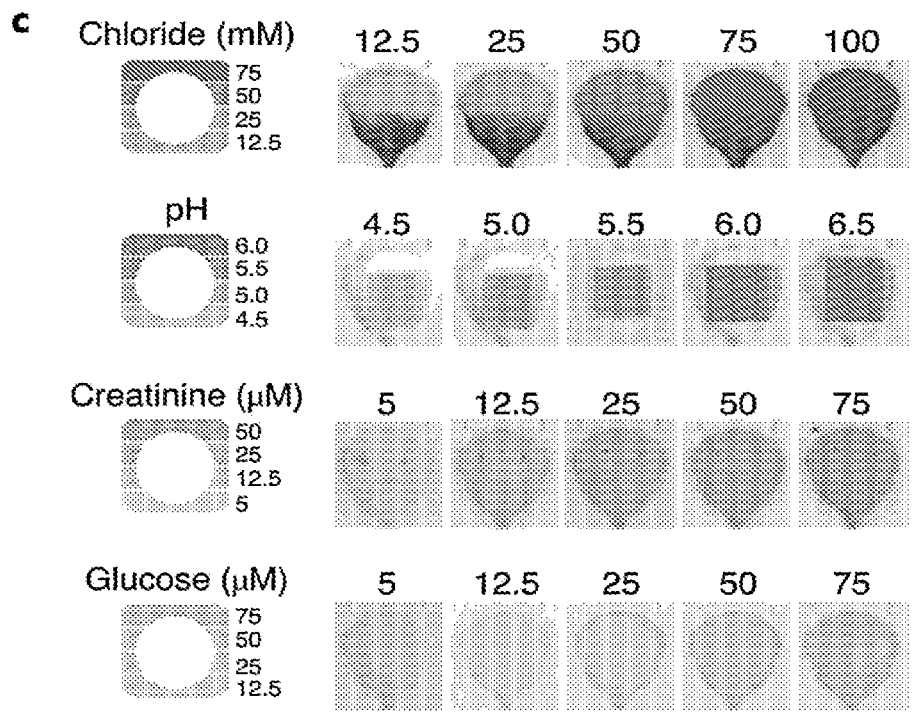
Figures 20A, 20B:
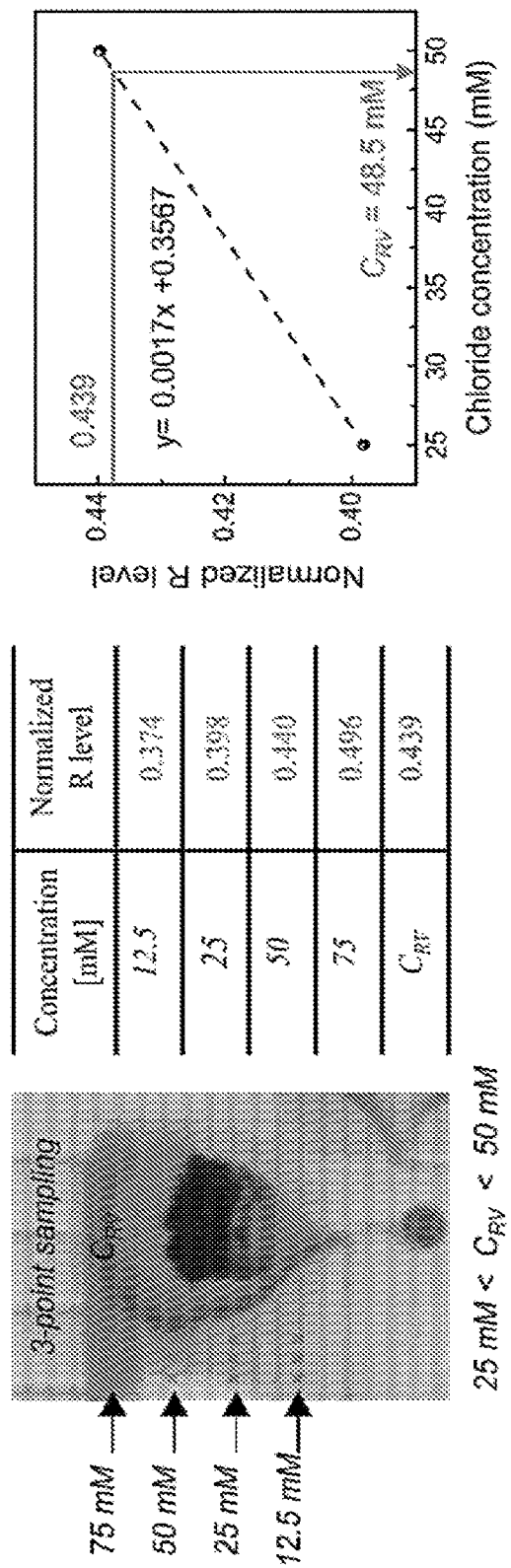
FIGS. 20A-20B show respectively interpolation method to analyze the concentration from the normalized color value of sweat filled reservoir using prepared color reference markers, according embodiments of the invention.
Figures 21A, 21B:
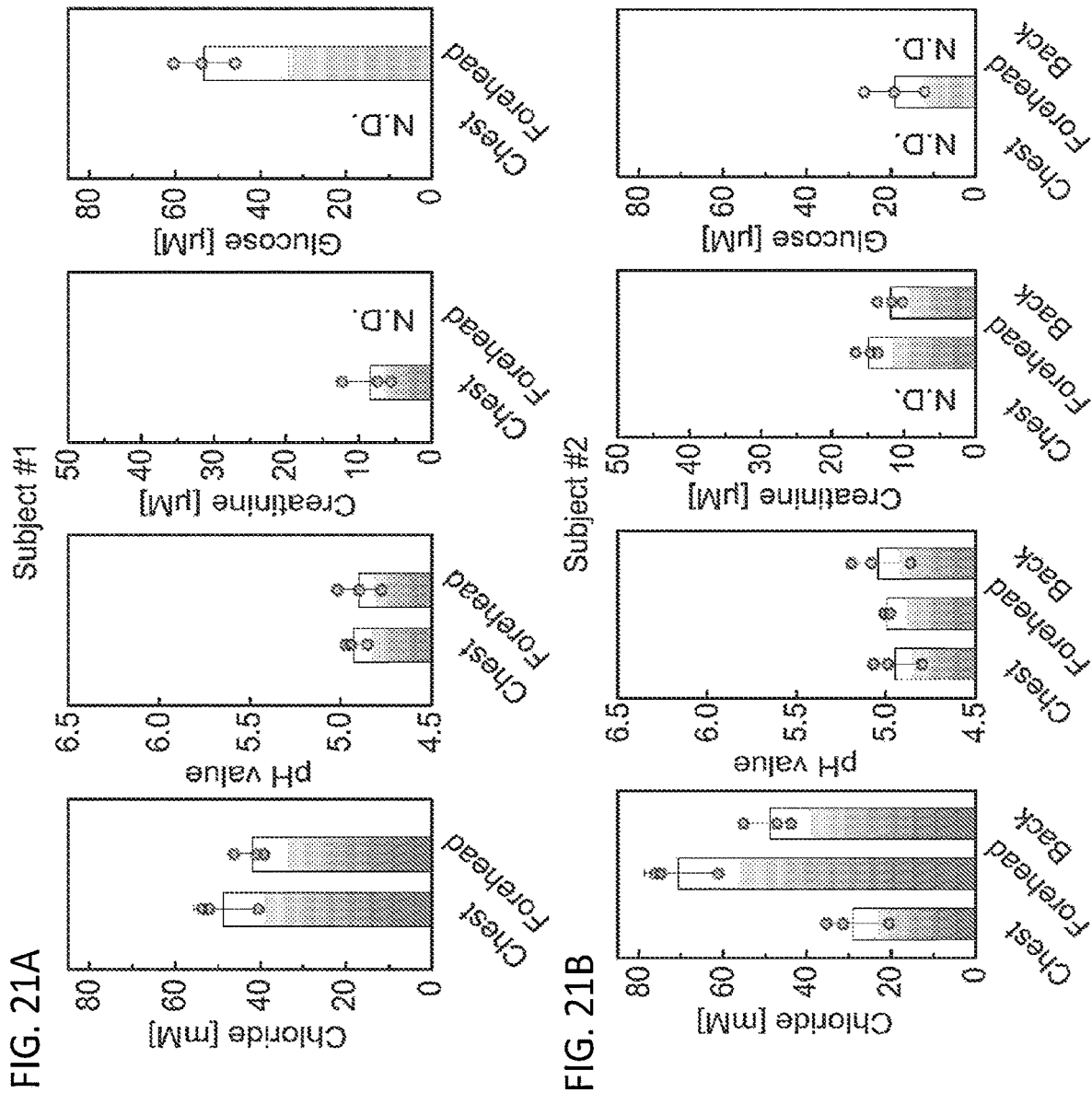
FIGS. 21A-21B show regional variations of sweat concentration (chloride, pH, creatinine, and glucose) from different body regions, according embodiments of the invention. Measurements of sweat-chloride/creatinine/glucose/pH levels (dots, data points) from a device mounted on the forehead, and torso regions from subject #1 (FIG. 21A), and #2 (FIG. 21B). Data are represented as mean values (bar graph)±SD (vertical error bars) measured at three different locations from each assay (sample size=3). N.D. represents data not collected due to insufficient sweat generation.
Figure 22A:
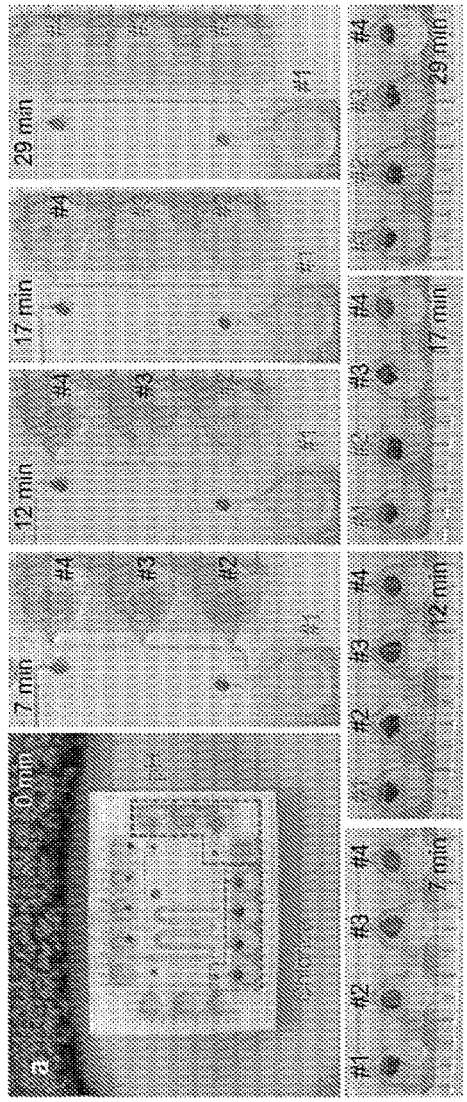
FIGS. 22A-22B show chronological measurements of chloride and pH levels from a healthy volunteer during gymnastics, according embodiments of the invention.
Figure 22B:
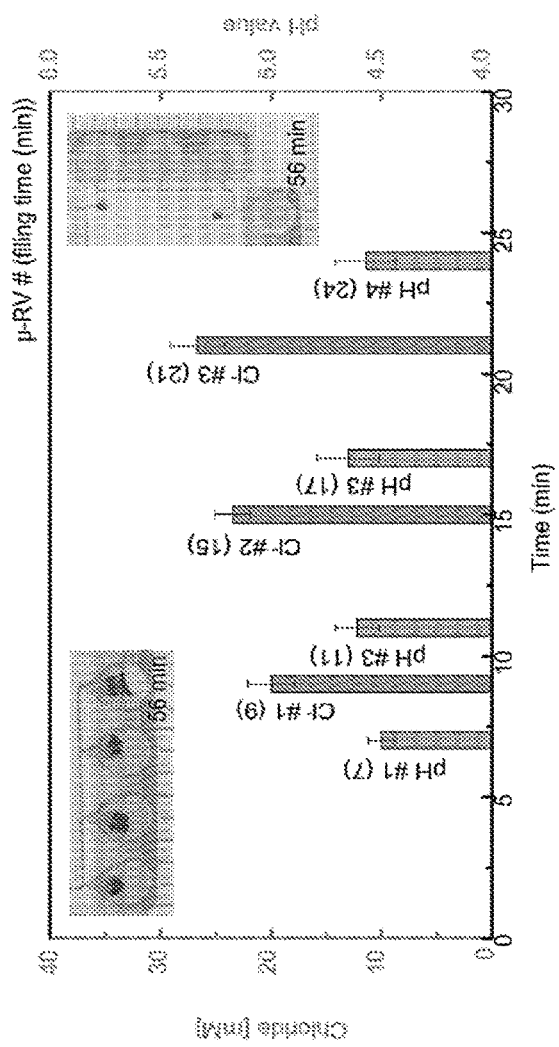

Sweat fills the inlet ports of the device and passes through a short fluid passage (width and height of 500 μm and 125 μm, respectively) from inlet a (inset, FIG. 5A) or enters into a series of microscale reservoirs (μ-RVs; volume of 10 μl) from inlets b-e (FIG. 5A). The μ-RVs from inlet b-e contain chemical and/or enzymatic assays for colorimetric detection of pH and of the concentration of chloride, creatinine, and glucose, respectively. Each μ-RV fills in a sequential manner (from #1 to #4, FIGS. 16A-16B) due to the action of capillary bursting valves (CBVs), thereby allowing for measurements of changes in the concentrations of these species in sweat as a function of sweat loss. An exploded view illustration of the system (FIG. 5B) highlights various aspects of the multilayered structure: the reusable, removable wireless platform, the color reference layer, a capping layer with a short fluid passage, colorimetric assays, microfluidic networks (μ-NETs; a serpentine channel and a collection of μ-RVs separated by CBVs), and an adhesive layer. A soft, biomedical adhesive (3M 1524) with five openings that define the sweat collection areas (19.6 mm$^2$) at the inlet ports allows for a water-tight seal and strong bond to the skin. The microfluidic layers of polydimethylsiloxane (PDMS) include (1) a capping layer (about 450 μm thickness) with a short fluid passage (blue) for measuring the sweat rate/loss and (2) μ-NETs (about 700 μm thickness) that include a serpentine microchannel for the capture/storage (about 40 μL volume) of sweat as it emerges from the outlet of the segment of the capping layer where digital flow measurements occur (FIGS. 17A-17B), and four separate sets of connected, circular μ-RVs for chronological measurements of pH and of concentrations of glucose, chloride, and creatinine. Color reference markers printed on a thin (25 μm) polyester adhesive film (THERML film SELECT® 10852, FLEXcon) allow precise extraction of color information by digital image analysis. An illustration and a picture of the full-assembled system are shown in FIGS. 18A-18B. FIG. 5C shows pictures of the reference markers for each assay (left; FIGS. 19A-19D) and images of color development in each μ-RV for samples of artificial sweat with pH levels and chloride, creatinine and glucose concentrations within physiologically relevant ranges (right). On-body trials with healthy volunteers demonstrate measurements of sweat-chloride/creatinine/glucose/pH levels using these platforms, across regions of the body with different shapes and curvatures. Image analysis at three different locations from each μ-RV provides an averaged color value to yield, after calibration to the reference markers, quantitative information for each biomarker. FIGS. 20A-20B highlight a specific example for measurement of chloride concentration. FIGS. 21A-21B show results from the forehead and torso (chest of subject #1 and chest/back of subject #2) of two male subjects while cycling (at early afternoon for #1, and at late afternoon for #2). All values are within the normal range. Additional tests (FIGS. 22A-22B) demonstrate the capabilities for chronological sampling from a device mounted on the forehead while home training. μ-RVs for monitoring pH and chloride levels in sweat fill completely after 7 min, 11 min, 17 min, and 24 min of exercise (top), and after 9 min, 15 min, and 21 min of exercise, respectively. Data show increases in concentration of chloride, and pH level during exercise, comparable to previous studies.

Figure 5D:
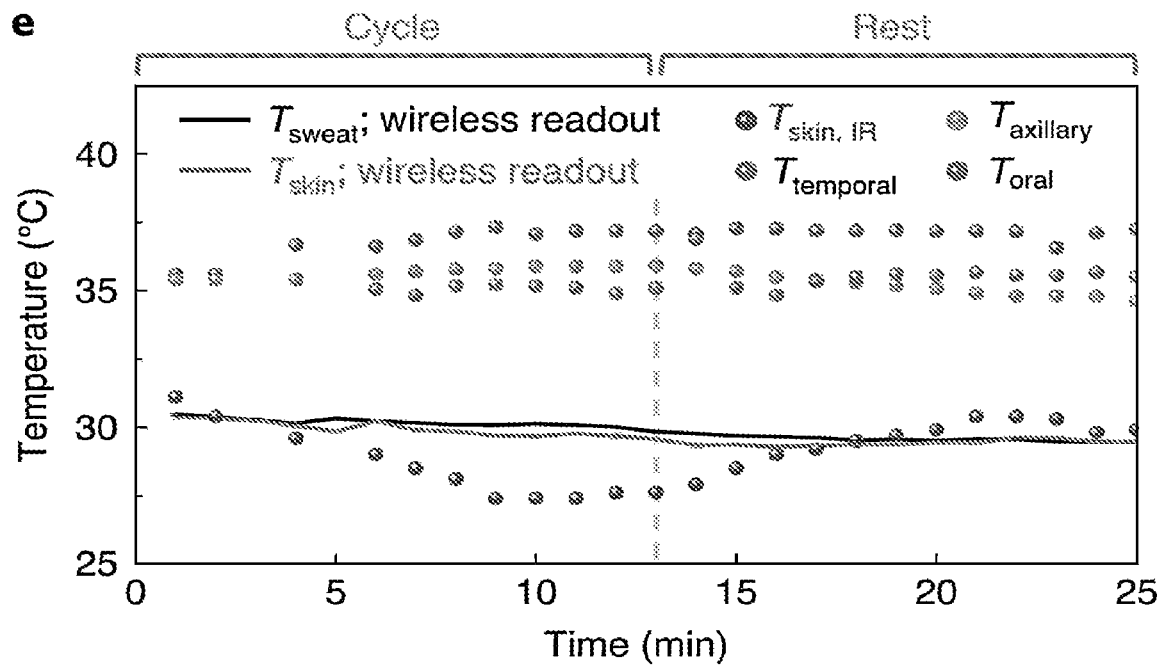
Figure 5E:
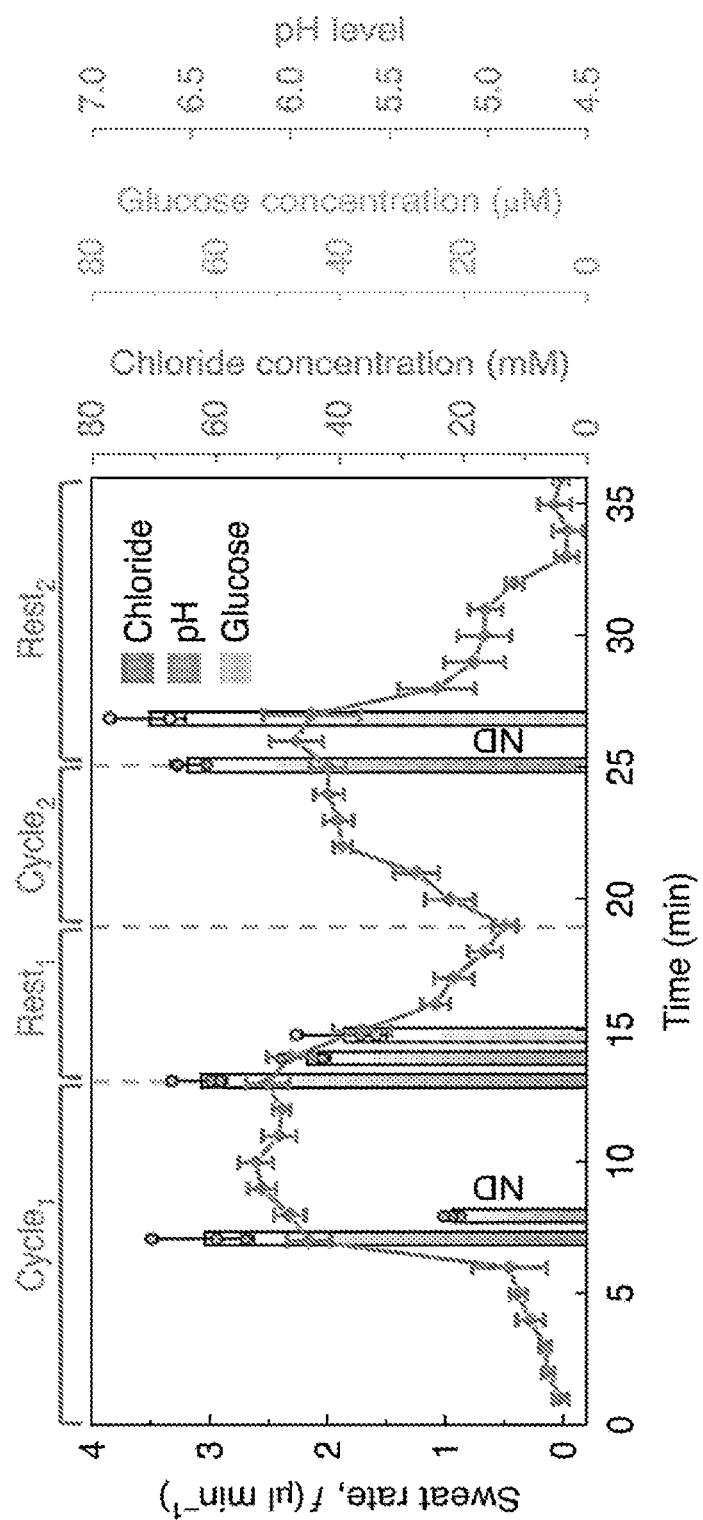

Further testing during cycling and at rest demonstrates multimodal sensing of sweat rate/loss, and the concentration of chloride and glucose in sweat, along with its pH. FIG. 5E shows sweat rate (f, red) and loss (Σf, FIG. 23) measured wirelessly every 1 min, and chloride (purple)/glucose (orange)/pH (yellow) upon filling of each μ-RV, from a device mounted on the forehead. Error bars represent the SD of the measurements of sweat rate over a 1-min averaging window (gray), and of chloride/glucose/pH at three different locations from each assay (black). During the session labeled "Cycle$_1$", the sweat rate rapidly increases after 6 min of exercise, to reach a value (about 2.4±0.1 μL·min$^{-1}$) that remains constant until the end of the cycling, and then decreases gradually during the rest state, labeled "Rests". During the session labeled "Cycle$_2$", the rate again increases at the onset of exercise, reaches a constant value (about 2.1±0.1 μL·min$^{-1}$), and then decreases to zero (about 0.0±0.05 μL·min$^{-1}$) during "Rest$_2$." The sweat volume (Σf) reaches 11.1 μL, 20.7 μL, and 31.63 μL after about 10 min, 14 min, 23 min of exercising, respectively. Measurements of concentrations of chloride are 61.7 mM, 62.3 mM, and 64.5 mM after about 8 min, 14 min, and 26 min of exercising, respectively, with SDs of 7.8 mM, 4.2 mM, and 2.8 mM. These values are within the normal range, and the times for filling each μ-RV (10 μL volume) are consistent with those obtained using the flow-sensing platform. Measurements of pH are 5.2 and 6.1 after about 8 min and 14 min of exercising, respectively, with a SD of 0.04 and 0.08. This increase in pH during exercise is consistent with results of previous studies. Measurements of concentrations of glucose are 39.2 μM and 70.6 μM after about 14 min and 23 min of exercising, respectively, with SDs of 6.8 μM and 5.6 μM. The increase in glucose is relevant to dehydration, which leads to increases in the concentration of glucose (sugar) in the blood and consequently in sweat, comparable to observations of sweat glucose in previous research.

Figure 23:
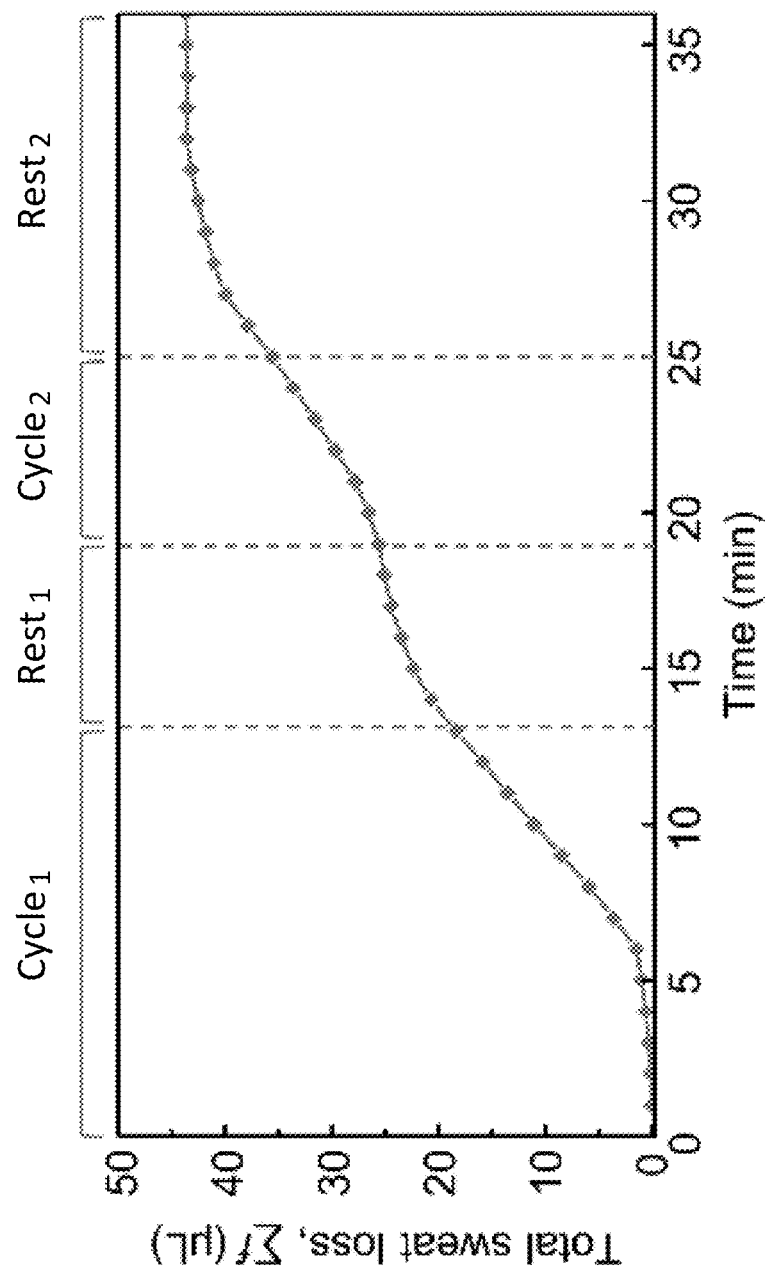
FIG. 23 shows cumulative sweat loss (Σf square markers) during work out, according embodiments of the invention.

Further testing during cycling and at rest demonstrates multi-modal sensing of sweat rate and loss, as well as sweat chloride, glucose and pH levels. FIG. 5E shows the sweat rate (f; red) and loss (Σf; FIG. 23), measured wirelessly every 1 min, and chloride (purple), glucose (yellow) and pH (orange) on filling each μ-RV, from a device mounted on the forehead. The error bars represent the s.d. values for the measurements of sweat rate over a 1-min averaging window (grey), and of chloride, glucose and pH levels at three different locations for each assay (black). The sweat volume (Σf) reaches 11.1, 20.7 and 31.63 μl after ~10, 14 and 23 min of exercising, respectively. The concentrations of chloride are measured to be 61.7, 62.3 and 64.5 mM after ~8, 14 and 26 min of exercising, respectively. These values are within the normal range, and the times for filling each μ-RV (volume, 10 μl) are consistent with those obtained using the flow-sensing platform. The increase in pH during exercise is consistent with the results of previous studies, originating from the anatomy of sweat glands and their operation. The measurements of glucose concentration are 39.2 and 70.6 μM after ~14 and 23 min of exercising, respectively. Given the reported correlation between glucose concentration in blood and sweat, the increase in glucose level might be related to release of the stress hormone cortisol during intense exercise, which causes an increase in blood glucose and consequently glucose in sweat. Additional details concerning the results are presented as follows.

Sweat rate: As shown in FIG. 5E, during the session labeled "Cycles", the sweat rate rapidly increases after 6 min of exercise, to reach a value (~2.4±0.1 μL·min$^{-1}$) that remains constant until the end of the cycling, and then decreases gradually during the rest state, labeled "Rest1." During the session labeled "Cycle$_2$", the rate again increases at the onset of exercise, reaches a constant value (~2.1±0.1 μL·min$^{-1}$), and then decreases to zero (~0.0±0.05 μL·min$^{-1}$) during "Rest$_2$".

Sweat pH: As shown in FIG. 5E, measurements of pH are 5.2 and 5.9 after ~8 min and 14 min of exercising, respectively, with a SD of 0.04 and 0.12. While the primary sweat pH is close to 7, sweat becomes acidic due to re-absorption processes in the duct and excreted on to the skin. During exercise, as the sweat excretion rates increases, the amount of time available for re-adsorption processes decreases and sweat pH increases.

Recent studies relevant to sweat glucose: A recent study presents the effect of dehydration on blood glucose, but further investigations are necessary. Results in several literature reports indicate that the glucose level in sweat gradually decreases during exercising due to the dilution effect of increasing sweat rate. Continuous glucose monitoring with comparisons to a gold-standard reference techniques (e.g. blood glucose meters) and with quantitative measurements of sweat release kinetics using systems like those introduced here, across a range of subjects, exercise types, intensities and durations, will be required to establish a comprehensive understanding of increases and decreases in glucose levels and associated physiological effects.

Figure 24A:
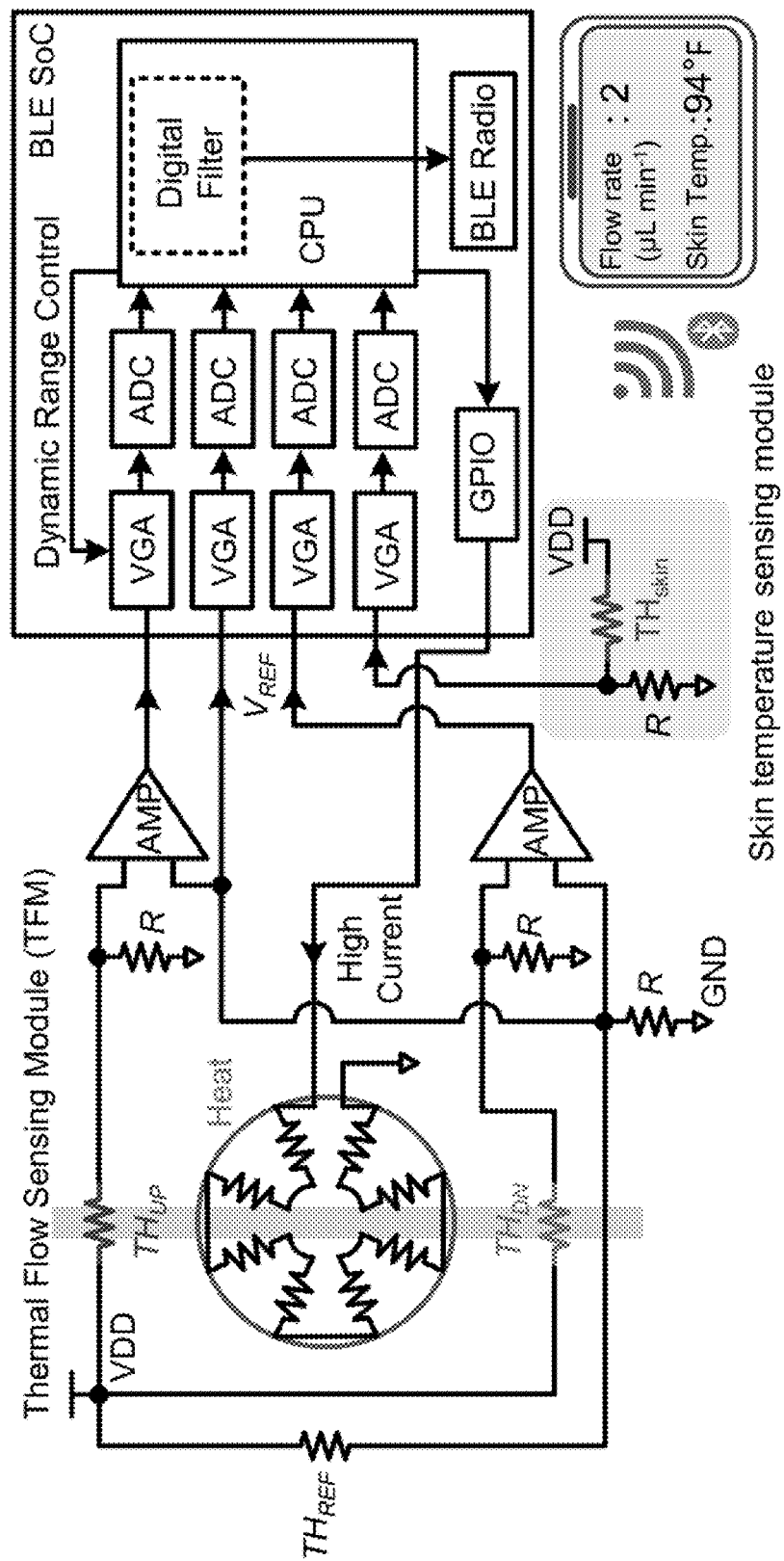
FIGS. 24A-24C show wireless platforms with capabilities for measuring skin temperature, according embodiments of the invention.
Figures 24B, 24C:
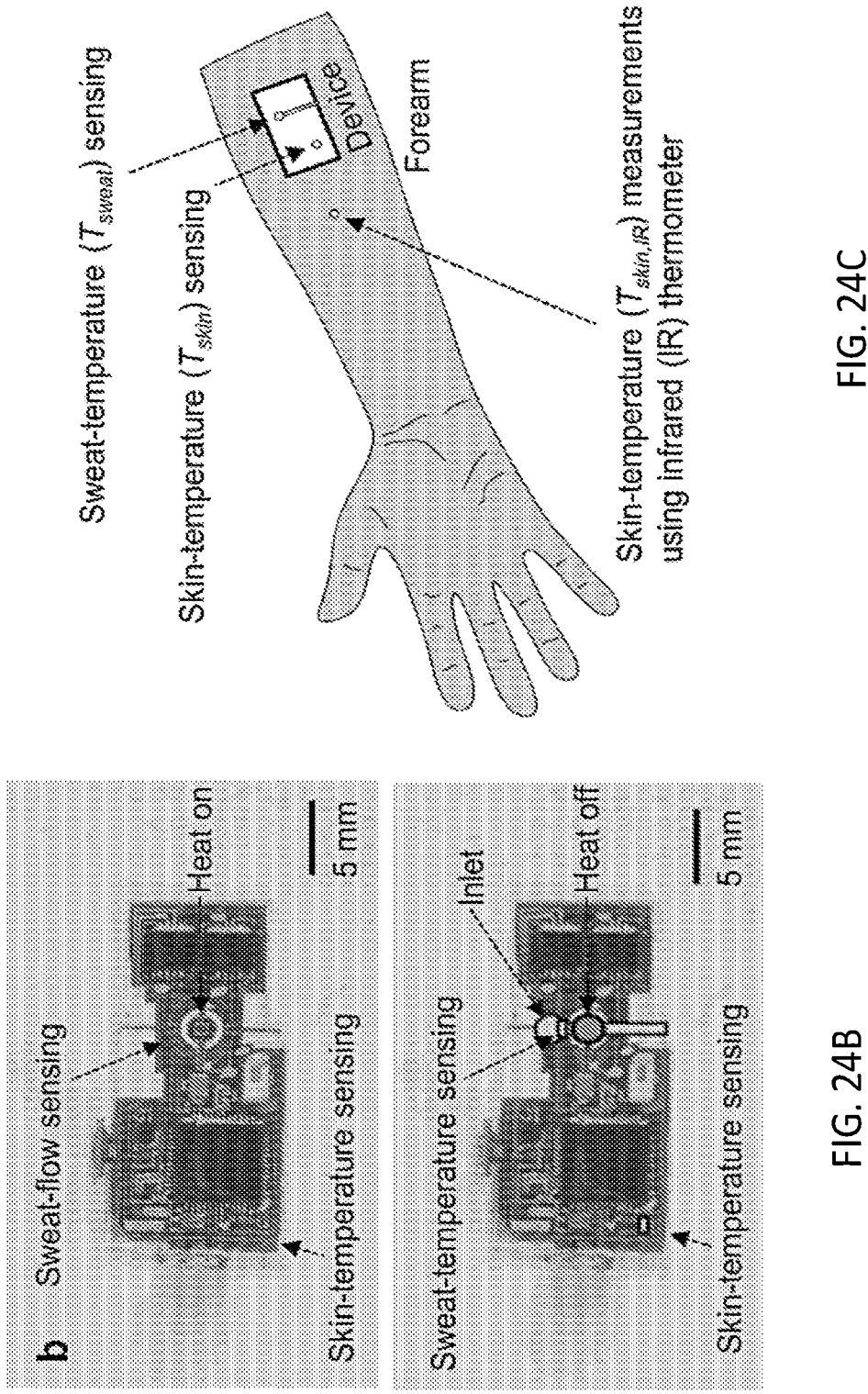
Figure 25A:
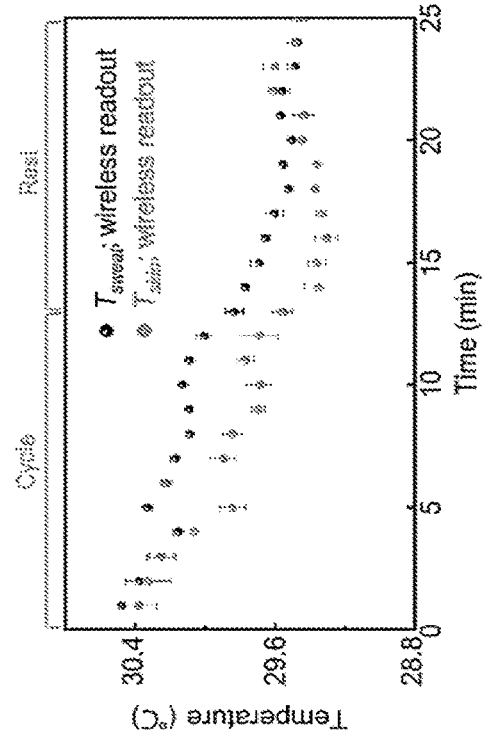
FIGS. 25A-25B show measurements of sweat ($T_{sweat}$) and skin (Tskin) temperatures, according embodiments of the invention.
Figure 26A:
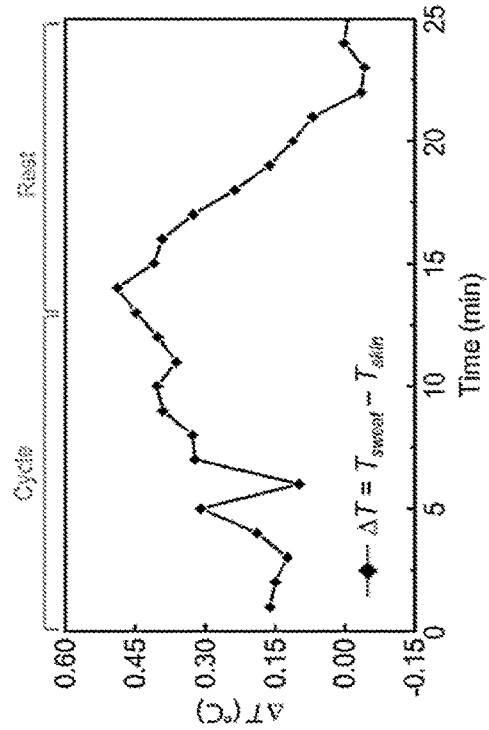
FIGS. 26A-26B show measurements of sweat rate and skin temperatures, according embodiments of the invention.
Figure 25B:
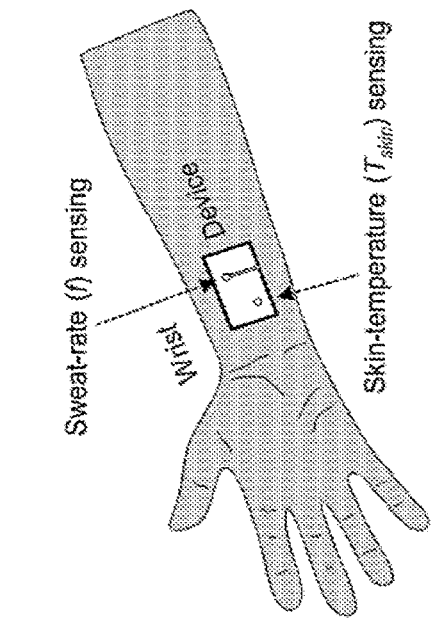
Figure 26B:
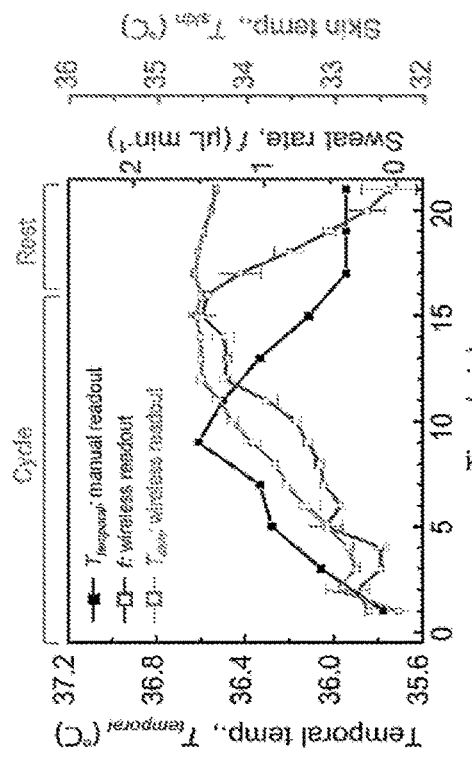

Another example of the versatility of the flow-sensing BLE SoC platform is in capabilities for measuring skin temperature, a critical parameter that is complementary to sweat in the context of cutaneous heat loss, body heat content, and central thermoregulatory control. A simple extension of the device platform involves an additional thermistor (15.5 mm away from the heater) connected in a voltage divider circuit with a known resistor (FIG. 24A), as an accurate means for measuring temperature. FIG. 5D shows the results of manual readings of oral ($T_{oral}$; purple), axillary ($T_{axillary}$; pink), temporal ($T_{temporal}$; green), and skin ($T_{skin,ir}$; blue) temperatures using basal (for $T_{oral}$ and $T_{axillary}$) and infrared (for $T_{temporal}$ and $T_{skin,IR}$) thermometers, and wireless measurements of sweat ($T_{sweat}$; black) and skin temperatures ($T_{skin}$; red) as a function of time (min) using a platform shown in FIG. 24B (bottom), mounted on the forearm of a healthy male subject (FIG. 24C) while cycling and at rest. During the session labeled "Cycle," the wireless measurements of $T_{sweat}$ and $T_{skin}$ steadily decrease, and reach a constant value (29.5° C.) during the session labeled "Rest". The difference between $T_{sweat}$ and $T_{skin}$ (FIG. 25A) steadily increases from 0.2° C. to 0.5° C. during cycling, and then decreases and reaches a constant value (0.0° C.) during "Rest", exhibiting a strong correlation with physical activity and with $T_{axillary}$ which increases from 35.4° C. to 35.9° C. during cycling, and decreases and reaches to a constant value (34.8° C.) while resting. $T_{skin,ir}$ depends strongly on cooling effects associated with evaporation of sweat, and by consequence shows large fluctuations, decreasing as evaporative cooling increases and then returning back to the baseline after exercise. $T_{oral}$ increases and reaches to a constant value ($T_{oral,mean}$=37.1° C. and $T_{oral,RMS}$=0.2° C.) after 10 min of exercise, and $T_{temporal}$ is relatively constant ($T_{temporal,mean}$=35.4° C. and $T_{temporal,RMS}$=0.5° C.). Error bars in FIG. 26B represent the SD of $T_{sweat}$ and $T_{skin}$ measured over a 1-min averaging window. Additional tests demonstrate the capabilities for measuring sweat rate and skin temperature from a device in FIG. 24B (top) mounted on the wrist during exercise (FIGS. 26A-26B).

Methods

Finite element analysis (FEA): The FEA commercial software Fluent was used to study the thermal response of the device to thermal actuation. The analysis was three-dimensional and transient, accounting for heat transfer in the fluid and solid at the ambient temperature, 25° C. The fluid in the passage was discretized by refined hexahedron elements to ensure computational accuracy, and the properties of water (specified in Fluent) used in the simulations were viscosity $v_F$=0.001 kg m$^{-3}$ s$^{-1}$, thermal conductivity $k_F$=0.6 W m$^{-1}$ K$^{-1}$ and thermal diffusivity $\alpha_F$=0.14 mm$^2$ s$^{-1}$. The flow rate, which changes with time as in experiments, was specified at the inlet of the fluid passage. The initial temperature of the fluid was the same as the ambient temperature, 25° C. As shown in FIG. 3D, the device, attached on the tissue surface, consisted of the PDMS passage, PDMS encapsulation, and electronics involving polyimide (PI) and copper. The model did not include a Li-polymer battery because of its large distance from the actuator and sensors. All solid components were discretized by tetrahedral elements. The relevant material properties were $k_p$=0.27 W m$^{-1}$ K$^{-1}$ and $\alpha_p$=0.16 mm$^2$ s$^{-1}$ for the PDMS passage, $k_{PI}$=0.21 W m$^{-1}$ K$^{-1}$ and $\alpha_{PI}$=0.11 mm2 s$^{-1}$ for PI and $k_{Cu}$=387 W m$^{-1}$ K$^{-1}$ and $\alpha_{Cu}$=113 mm$^2$ s$^{-1}$ for copper. A constant temperature of 32° C. was imposed on the bottom surface of the device in most studies, although 25° C. and 35° C. were also imposed to study the effect of this temperature.

Fabrication of the electronics: A thin, flexible film (AP8535R, Pyralux, DuPont) of copper/PI/copper (thicknesses of 18 µm, 75 µm and 18 µm) served as a substrate. An ultraviolet laser cutter (Protolaser U4, LPKF) ablated the copper to define conductive traces, bond pads and through-hole vias, resulting in a flexible printed circuit board (fPCB). A silver conductive paint (cat. no. Z05001, SPI Supplies) created conductive plugs between the top and bottom patterned copper layers through the vias when heated at 90° C. using a heat gun (AOYUE Int866). Soldering paste (TS391LT, Chip Quik) was used to join the various surface-mounted components, including the BLE SoC (nRF52832, Nordic Semiconductor), antenna (2450AT18A100, Johanson Technology), amplifier (INA333, Texas Instruments), reference and heater resistors (each with a width of 0.3 mm, a length of 0.6 mm and a height of 0.25 mm; RMCF0201FT, Stackpole Electronics) and sensor components (NTC, NCP03XH, Murata), onto the fPCB by heating at 180° C. Soft silicone materials including Silbione (RTV 4420, Bluestar Silicones) and PDMS (Sylgard 184, Dow Corning) were moulded and cured at 100° C. to form a robust encapsulating structure.

Fabrication of the flow sensing module: Fabrication of the molds began with photolithographically defined patterns of photoresist (KMPR 1010; Microchem, MA, USA) formed by spin casting at 2000 rpm for 30 s on silicon wafers (1 mm thickness), followed by baking on a hot plate at 100° C. for 5 min, exposing to UV with a dose of 600 mJ/cm$^2$, post-exposure baking on a hot plate at 100° C. for 5 min, and immersing in developer (AZ 917MIF; Integrated Micro Materials, TX, USA) for 7 min. Deep reactive ion etching (STS Pegasus ICP-DRIE; SPTS Technologies, Newport, United Kingdom) formed relief structures in the silicon to depths of 125±5 µm to define a flow sensing passage. A layer of polymethylmethacrylate (PMMA; 3000 rpm for 30 s, curing at 180° C. for 2 min on a hot plate) spin cast on these molds facilitated release of PDMS after casting and curing. Spin casting PDMS (Sylgard 184; Dow corning, MI, USA; mixing ratio of base to curing agent is 10:1) on the PMMA-coated mold at 200 rpm for 30 s, followed by degassing the sample under vacuum to remove the air bubbles, then baking on a hot plate at 150° C. for 5 min produced a solid replica of the etched features. After releasing from the Si mold, a mechanical punch tool defined an inlet hole. For benchtop and body testing as shown in FIGS. 2A-2I and 4A-4I, spin-coating a layer of PDMS (10:1 mixing ratio) on PMMA-coated unpatterned silicon wafer at 1000 rpm, followed by baking on a hot plate at 150° C. for 3 min yielded an approximately 70 µm thick ($t_{Top}$) flat capping layer. This capping layer bonded to the passage structure using oxygen plasma treatment, to complete the fabrication. For on-body testing, a CO$_2$ laser (Universal laser system, Inc.) formed the outline of a medical-grade acrylate adhesive (1524; 3M, MN, USA; 60 µm thickness). The adhesive bonded to the bottom surface of the device after UVO treatment for 4 min for water-tolerant adhesion.

Measurements of current consumed by the device: A Power Profiler Kit (PPK) board (NRF6707, Nordic Semiconductor) served as a current measurement tool for the device. The PPK supplied power to the device under test and used its ADC to measure a voltage drop across a series measurement resistor. The current consumed by the device is given by I=measured voltage drop (V)/resistor value (Ω). Through an nRF52 development kit board (nRF52-DK, Nordic semiconductor), the PPK board was connected to a computer with the PPK application, which provided a real-time display of the current measurements. Measurements of the current consumed by the device allowed estimations of battery life. With use for 1 h per day with flow measurements every minute and a 20% duty cycle of heating (heat on for 12 s before each measurement), the replaceable battery (Li-polymer battery, GMB351223; 70 mAh) in FIG. 3B (bottom) has an expected lifetime of two weeks.

Flow sensing integration with colorimetric microfluidic module: The process includes the fabrication of 1) a capping layer with a short fluid passage and 2) μ-NETs (a serpentine channel, and μ-RVs separated by CBVs). Spin-casting PDMS (10:1 mixing ratio) on a μ-CH featured (width× height: 500 μm×125 μm) mold at 400 rpm, followed by baking on a hot plate at 150° C. for 5 min produced solid replica of the etched features. After releasing from the Si mold, a mechanical punch tool (1 mm in diameter) defined an inlet, where sweat enters, flows through a passage and then to an outlet that couples to the inlet of the serpentine channel in NETs. Bonding 70 μm-thick flat capping layer to using oxygen plasma treatment completed the fabrication of structure to define the short fluid passage. A silicon wafer (1 mm thickness) patterned by abovementioned processes, served as a mold for μ-NETs with relief structures to depths of 600±5 μm. Spin casting PDMS (10:1) mixed with white silicone dye (Reynolds Advanced Materials, IL, USA)) at 3 wt % on the mold at 200 rpm, baking on a hot plate at 150° C. for 3 min, allowed releasing of a microfluidic network layer. Then, a mechanical punch tool defined five inlet holes that couple to skin (inlet a-e in FIG. 5A). After loading each colorimetric assay in each μ-RV, spin casting tacky layer of PDMS (50:1 mixing ratio) at 1000 rpm, baking at 150° C. for 3 min yielded a 75 μm-thick bonding layer between the capping layer with fluid passage and μ-NETs, in a manner aligned with the interconnect hole, through gentle contact at room temperature. A transparent polyester film with adhesive on the backside (THERMLfilm SELECT® 10852; FLEXcon, MA, USA; thickness 25 μm) mounted on the top of the device with color reference graphics with each assay. Finally, the adhesive bonded to the bottom surface of the device after UVO treatment.

Heat distribution measurement and visualization: Pictures collected with an IR camera (FLIR Systems, a6255sc) revealed the spatial distributions of surface temperature. A microfluidic module formed with PDMS mixed with a thermochromic pigment (Temperature Activated Thermochromic Bi-Color Powder Pigment, Atlanta Chemical Engineering) that changes in color from black to pink above 25° C. provided an additional means to visualize the temperature distribution.

Benchtop study: The experimental set-up and wireless electronics platform for measurements with flow rates of 0, 1, 2, 3 and 4 μl min$^{-1}$ (set using a syringe pump, NE-300, New Era) are presented in FIG. 6A-6B. The sensors and associated electronics were mounted on the top surface of a structure that defined a passage with inlet/outlet ports sealed to polyethylene (PE) tubing (A-M Systems, 801300). A BLE SoC configured with analogue front-end circuits controlled power to the thermal actuator and transmitted the responses of the thermistors to a BLE-enabled smartphone, for real-time graphical display and storage of the time-dependent differences in temperature between upstream ($TH_{UP}$) and downstream ($TH_{DN}$) locations.

Colorimetric assay: (1) chloride: The assay solution used 50 mg of silver chloranilate (MP Biomedicals, CA, USA) dispersed in 200 μL of 2% pHEMA (poly (2-hydroxyethyl methacrylate)). Spotting 2.5 μL of this solution into the μ-RVs, followed by drying under vacuum chamber for 1 h prepare the system for measurements. (2) pH: A strip of commercial indicator paper (Whatman, 2614-991, UK) served as the assay for pH measurement, cut with a razor blade into an octagonal shape to facilitate insertion into the μ-RVs. (3) glucose: combining the glucose substrate mix and glucose assay buffer yielded the glucose substrate solution. Spotting 0.5 μL of this substrate solution onto μ-RVs, and drying under vacuum in a desiccator for 1 h produced the glucose assay. Next, spotting 0.5 μL of enzyme mixed with DI water at an adjacent location, followed by drying under vacuum chamber for 1 h completed the process (Glucose Colorimetric Assay Kit II, No. K686, Biovision, CA, USA). (4) Creatinine: Thoroughly mixing a solution of creatininase, creatinase, and enzyme in a 1:1:1 ratio yielded the assay. Spotting 1.25 μL of the solution into the μ-RV, followed by drying under vacuum chamber for 1 h and then spotting 0.75 μL of creatinine probe at an adjacent location, followed by drying under vacuum chamber for 2 h, completed the process. (Creatinine Assay Kit; Sigma-Aldrich, MO, USA).

Standard color development and color reference marker preparation: Mixing sodium chloride, D(+) glucose and L(+) lactic acid (Sigma-Aldrich, MO, USA) in DI water yielded standard test solutions. Mixing 0.2 M sodium phosphate and 0.1 M citric acid produced pH buffer solutions with pH ranging from 4.5 to 6.5 defined by a pocket ion-sensitive field-effect transistor (ISFET) pH meter (Model 24004, DeltaTrak, CA, USA). The colorimetric devices were placed on a hot plate set at about 32° C. to mimic skin/body temperatures, to receive pipetted standard solutions into the μ-RVs for color development. Reaction proceeded for 25 min with chloride, creatinine and glucose assays and 5 min with the pH assay. A digital SLR camera (EOS 6D; Canon, Tokyo, Japan) captured images of the device. Corona treatment (Electro-Technic Products) of a polyester film for 30 s allowed efficient bonding prior to printing color reference markers with a color laser printer (Color image CLASS MF726Cdw, Canon) to match those determined using the methods described above. After attaching this printed polyester film on the device, a smartphone camera (iPhone 11; Apple, CA, USA) used to take additional images.

Human participant trials in practical scenarios: The experimental protocols for the on-body studies were approved by the Institutional Review Board of Northwestern University (STU00208494), and all participants provided their consent prior to test. Healthy adult volunteers (age 28-40 years, male healthy individuals) performed normal stationary cycling with no additional human-participant risk, following the provided study guidelines. Cleaning the relevant body locations with an alcohol swab enhanced adhesion by removing contaminants from the skin before device application. During cycling, a smartphone camera (iPhone 11, Apple) was used to take pictures of the devices for subsequent analysis of the digital images. Non-contact infrared (Fisher Scientific), digital (Fisher Scientific) and oral (BBT-113Ai, IProven) thermometers were used to manually measure the temperatures of the different body locations.

Digital image analysis for the evaluation of sweat concentrations: The PowerPoint eyedropper tool defined RGB values from three random points in each μ-RV and the associated reference marker in the images. Mean normalized RGB values (R for chloride, G for pH and creatinine, and B for glucose) from the references and from μ-RVs determined the range of a discrete set of known concentration points and the analyte concentration by linear interpolation (FIG. 20B), respectively.

In vitro microfluidic test and bursting pressure calculation: The bursting pressure (BP) of a CBV is $$BP = -2\sigma\left[\frac{\cos\theta_1^*}{w} + \frac{\cos\theta_A}{h}\right]$$

Where σ is surface tension of the liquid, $\theta_A$ is the critical advancing contact angle of the fluid passage, $\theta_1^* = \min(\theta_A +$ β, 180°) and β is the diverging angle of the passage, and w and h are the width and height of the diverging section, respectively. The surface tension of water is 0.072 N·m$^{-1}$ at the ambient temperature, and the advancing contact angle of water on PDMS is 125°±2°.

CONCLUSION

The exemplary study has demonstrated soft, wireless platforms for the accurate and reproducible analysis of sweat rate and loss, as well as skin temperature. The technology exploits a flexible circuit that combines a thermal sensing module for sweat monitoring with BLE functionality for wireless data transfer. The system requires only indirect contact with sweat, thereby preserving its sensitivity, accuracy and reusability for applications in practical conditions. Our platform can provide real-time information on sweat rate and loss, without the need for visual user engagement or complex, single-use micro-fluidic channels.

The approach disclosed in the invention has the potential to be used in personalized hydration strategies, with additional promise for monitoring and managing health disorders. For example, the device can be configured to activate alerts to remind users to respond appropriately to avoid heat stress and the risks of dehydration, or to provide prompts to inform rehydration protocols in working or training environments that involve high heat stress conditions or heavy personal protective equipment. Additional potential lies in the continuous monitoring of patients during normal activities to diagnose sweat-related disorders and to assess associated treatments. Scaling laws for the effects of the thermal conductivity, heat capacity and density of the sweat and the packaging materials used around the sensor component should aid in the optimization of designs for these and other applications.

For clinical applications of these devices, an improved understanding is required of the correlations between sweat-related parameters and physiological status, including variabilities among patients. In particular, monitoring sweat rate and loss in patients with hyperhidrosis and anhidrosis, before and after alcohol consumption and in cases of insensible sweating, are interesting directions for future research. Another possibility lies in determining relationships between regional and whole-body sweat rates and electrolyte concentrations. Variations exist among and within individuals, including day-to-day variabilities, in models that predict whole-body values from regional measurements. Research using a wearable unit with high temporal resolution, such as the platform introduced here, could be a valuable component in future studies.

The modular system of the invention can be integrated with various microfluidic technologies, as well as colorimetric chemical or enzymatic reagents, to provide accurate colorimetric estimates of chloride concentration, pH and biomarkers such as creatinine and glucose. Other options include microfluidic technologies for drug delivery or devices for the measurement of the pulse wave velocity of macrovascular and microvascular blood flow near the skin surface, with potential for continuous, non-invasive monitoring of blood pressure. In particular, integration of thermal flow sensing platforms with drug delivery systems can also serve as a basis for control over the delivery process, through real-time measurements of release rate and exact dosages. Such technology could organize doses of medication by day and time, and assist caregivers and family members in tracking a medication schedule.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

[1]. Baker, L. B. Sweating rate and sweat sodium concentration in athletes: a review of methodology and intra/interindividual variability. *Sports Med.* 47, 111-128 (2017).

[2]. Gambhir, S. S., Ge, T. J., Vermesh, 0. & Spitler, R. Toward achieving precision health. *Sci. Transl. Med.* 10, eaao3612 (2018).

[3]. Bariya, M., Nyein, H. Y. Y. & Javey, A. Wearable sweat sensors. *Nat. Electron.* 1, 160-171 (2018).

[4]. Sonner, Z. et al. The microfluidics of the eccrine sweat gland, including biomarker partitioning, transport and biosensing implications. *Biomicrofluidics* 9, 031301 (2015).

[5]. Gao, W. et al. Fully integrated wearable sensor arrays for multiplexed in situ perspiration analysis. *Nature* 529, 509-514 (2016).

[6]. Reeder, J. T. et al. Waterproof, electronics-enabled, epidermal microfluidic devices for sweat collection, biomarker analysis and thermography in aquatic settings. *Sci. Adv.* 5, eaau6356 (2019).

[7]. Bandodkar, A. J. et al. Battery-free, skin-interfaced microfluidic/electronic systems for simultaneous electrochemical, colorimetric and volumetric analysis of sweat. *Sci. Adv.* 5, eaav3294 (2019).

[8]. Baker, L. B., Stofan, J. R., Hamilton, A. A. & Horswill, C. A. Comparison of regional patch collection vs. whole body washdown for measuring sweat sodium and potassium loss during exercise. *J. Appl. Physiol.* 107, 887-895 (2009).

[9]. Maughan, R. J. et al. Water balance and salt losses in competitive football. *Int. J. Sport Nutr. Exerc. Metab.* 17, 583-594 (2007).

[10]. Williams, C. A. & Blackwell, J. Hydration status, fluid intake and electrolyte losses in youth soccer players. *Int. J. Sports Physiol. Perform.* 7, 367-374 (2012).

[11]. Al-omari, M. et al. A portable optical human sweat sensor. *J. Appl. Phys.* 116, 183102 (2014).

[12]. Bandodkar, A. J. & Wang, J. Non-invasive wearable electrochemical sensors: a review. *Trends Biotechnol.* 32, 363-371 (2014).

[13]. Dam, V. A. T., Zevenbergen, M. A. G. & van Schaijk, R. Toward wearable patch for sweat analysis. *Sens. Actuators B Chem.* 236, 834-838 (2016).

[14]. Bain, A. R., Deren, T. M. & Jay, O. Describing individual variation in local sweating during exercise in a temperate environment. *Eur. J. Appl. Physiol.* 111, 1599-1607 (2011).

[15]. Patterson, M. J., Galloway, S. D. R. & Nimmo, M. A. Variations in regional sweat composition in normal human males. *Exp. Physiol.* 85, 869-875 (2000).

[16]. Matzeu, G., Fay, C., Vaillant, A., Coyle, S. & Diamond, D. A wearable device for monitoring sweat rates via image analysis. *IEEE Trans. Biomed. Eng.* 63, 1672-1680 (2016).

[17]. Choi, J., Ghaffari, R., Baker, L. B. & Rogers, J. A. Skin-interfaced systems for sweat collection and analytics. *Sci. Adv.* 4, eaar3921 (2018).

[18]. Francis, J., Stamper, I., Heikenfeld, J. & Gomez, E. F. Digital nanoliter to milliliter flow rate sensor with in vivo demonstration for continuous sweat rate measurement. *Lab Chip* 19, 178-185 (2019).

[19]. Iftekhar, A. T., Ho, J. C.-T., Mellinger, A. & Kaya, T. 3D modeling and characterization of a calorimetric flow rate sensor for sweat rate sensing applications. *J. Appl. Phys.* 121, 094505 (2017).

[20]. Brueck, A., Iftekhar, T., Stannard, B. A., Yelamarthi, K. & Kaya, T. A real-time wireless sweat rate measurement system for physical activity monitoring. *Sensors* 18, 533 (2018).

[21]. Farrell, P. M. et al. Guidelines for diagnosis of cystic fibrosis in newborns through older adults: Cystic Fibrosis Foundation consensus report. *J. Pediatr.* 153, S4-S14 (2008).

[22]. Moyer, J., Wilson, D., Finkelshtein, I., Wong, B. & Potts, R. Correlation between sweat glucose and blood glucose in subjects with diabetes. *Diabetes Technol. Ther.* 14, 398-402 (2012).

[23]. Robinson, S. & Robinson, A. H. Chemical composition of sweat. *Physiol. Rev.* 34, 202-220 (1954).

[24]. Bass, D. E. & Dobalian, I. T. Ratio between true and apparent creatinine in sweat. *J. Appl. Physiol.* 5, 555-558 (1953).

[25]. Al-Tamer, Y. Y., Hadi, E. A. & Al-Badrani, I. E. I. Sweat urea, uric acid and creatinine concentrations in uraemic patients. *Urol. Res.* 25, 337-340 (1997).

[26]. Harvey, C. J., LeBouf, R. F. & Stefaniak, A. B. Formulation and stability of a novel artificial human sweat under conditions of storage and use. *Toxicol. In Vitro* 24, 1790-1796 (2010).

[27]. Huang, C.-T., Chen, M.-L., Huang, L.-L. & Mao, I.-F. Uric acid and urea in human sweat. *Chin. J. Physiol.* 45, 109-115 (2002).

[28]. Brinkman, J. E. & Sharma, S. *Physiology, Metabolic Alkalosis* (StatPearls Publishing, 2019).

[29]. Patterson, M. J., Galloway, S. D. R. & Nimmo, M. A. Effect of induced metabolic alkalosis on sweat composition in men. *Acta Physiol. Scand.* 174, 41-46 (2002).

[30]. Choi, J. et al. Soft, skin-integrated multifunctional microfluidic systems for accurate colorimetric analysis of sweat biomarkers and temperature. *ACS Sens.* 4, 379-388 (2019).

[31]. Zhang, Y. et al. Passive sweat collection and colorimetric analysis of biomarkers relevant to kidney disorders using a soft microfluidic system. *Lab Chip* 19, 1545-1555 (2019).

[32]. Emrich, H. M. et al. Sweat composition in relation to rate of sweating in patients with cystic fibrosis of the pancreas. *Pediatr. Res.* 2, 464-478 (1968).

[33]. Ohara, K. Chloride concentration in sweat; its individual, regional, seasonal and some other variations, and interrelations between them. *Jpn J. Physiol.* 16, 274-290 (1966).

[34]. Coyle, S. et al. Textile sensors to measure sweat pH and sweat-rate during exercise. In *Proc. 3rd International ICST Conference on Pervasive Computing Technologies for Healthcare* 1-6, https://doi.org/10.4108/ICST.PERVASIVEHEALTH2009.5957 (ICST, 2009).

[35]. Oncescu, V., O'Dell, D. & Erickson, D. Smartphone based health accessory for colorimetric detection of biomarkers in sweat and saliva. *Lab Chip* 13, 3232-3238 (2013).

[36]. Torrente-Rodriguez, R. M. et al. Investigation of cortisol dynamics in human sweat using a graphene-based wireless mHealth system. *Matter* 2, 921-937 (2020).

[37]. Marriott, B. M. *Food Components to Enhance Performance: An Evaluation of Potential Performance-Enhancing Food Components for Operational Rations* (National Academic Press, 1994).

[38]. Robson, P. J. et al. Effects of exercise intensity, duration and recovery on in vitro neutrophil function in male athletes. *Int. J. Sports Med.* 20, 128-135 (1999).

[39]. Luger, A. et al. Acute hypothalamic—pituitary—adrenal responses to the stress of treadmill exercise. *New Engl. J. Med.* 316, 1309-1315 (1987).

[40]. Koc, S. The acute effect of aerobic exercise on serum cortisol levels of athletes and sedentary individuals. *J. Educ. Train. Stud.* 6, 29-36 (2018).

[41]. Hong, Y. J. et al. Multifunctional wearable system that integrates sweat-based sensing and vital-sign monitoring to estimate pre-/post-exercise glucose levels. *Adv. Funct. Mater.* 28, 1805754 (2018).

[42]. Emaminejad, S. et al. Autonomous sweat extraction and analysis applied to cystic fibrosis and glucose monitoring using a fully integrated wearable platform. *Proc. Natl Acad. Sci. USA* 114, 4625-4630 (2017).

[43]. Sessler, D. I. Temperature monitoring and perioperative thermoregulation. *Anesthesiology* 109, 318-338 (2008).

[44]. Zhang, Y. et al. Battery-free, fully implantable optofluidic cuff system for wireless optogenetic and pharmacological neuromodulation of peripheral nerves. *Sci. Adv.* 5, eaaw5296 (2019).

[45]. Yeung, C. et al. A 3D-printed microfluidic-enabled hollow microneedle architecture for transdermal drug delivery. *Biomicrofluidics* 13,

[46]. 064125 (2019).

[47]. Lopez-Ramirez, M. A. et al. Built-in active microneedle patch with enhanced autonomous drug delivery. *Adv. Mater.* 32, 1905740 (2020).

[48]. Webb, R. C. et al. Epidermal devices for noninvasive, precise and continuous mapping of macrovascular and microvascular blood flow. *Sci. Adv.* 1, e1500701 (2015).

[49]. Ma, Y. et al. Relation between blood pressure and pulse wave velocity for human arteries. *Proc. Natl Acad. Sci. USA* 115, 11144-11149 (2018).

[50]. Cho, H., Kim, H.-Y., Kang, J. Y. & Kim, T. S. How the capillary burst microvalve works. *J. Colloid Interface Sci.* 306, 379-385 (2007).

[51]. Choi, J. et al. Soft, skin-mounted microfluidic systems for measuring secretory fluidic pressures generated at the surface of the skin by eccrine sweat glands. *Lab Chip* 17, 2572-2580 (2018).

[52]. Liu, G. et al. A wearable conductivity sensor for wireless real-time sweat monitoring. *Sensors Actuators B Chem.* 227, 35-42 (2015).

[53]. Buskirk, E. R. & Puhl, S. M. *Body Fluid Balance: Exercise and Sport.* (CRC Press LLC, Boca Raton (Fla.), 1996).

[54]. Sato, K., Kang, W. H., Saga, K. & Sato, K. T. Biology of sweat glands and their disorders. I. Normal sweat gland function. *J. Am. Acad. Dermatol.* 20, 537-563 (1989).

[55]. Randall, W. C. Quantitation and regional distribution of sweat glands in man. *J. Clin. Invest.* 25, 761-767 (1946).

[56]. Gomez, I. J., Arnaiz, B., Cacioppo, M., Arcudi, F. & Prato, M. Nitrogen-doped carbon nanodots for bioimaging and delivery of paclitaxel. *J. Mater. Chem. B* 6, 5540-5548 (2018).

[57]. Keller, U., Szinnai, G., Bilz, S., & Berneis, K. Effects of changes in hydration on protein, glucose and lipid metabolism in man: impact on health. *Eur. J. Clin. Nutr.* 57, S69-S74 (2003).

[58]. Ashraf M. M., & Rea R. Effect of dehydration on blood tests. *Pract. Diabetes* 34, 169-171 (2017).

[59]. Toi, P. T. et al. Highly Electrocatalytic, Durable, and Stretchable Nanohybrid Fiber for On-Body Sweat Glucose Detection. *ACS Appl. Mater. Interfaces* 11, 10707-10717 (2019).

What is claimed is:

1. A sensor for measuring parameters of sweat from a skin, comprising:
    a flexible structure comprising a fluid passage having an inlet and an outlet, wherein the flexible structure is detachably attached to the skin and configured such that sweat enters the inlet as the sweat releases from a surface of the skin and flows through the fluid passage into the outlet;
    a thermal actuator disposed on the flexible structure over the fluid passage and configured to operably provide heat to flow of the sweat through the fluid passage;
    a first thermistor disposed on the flexible structure over the fluid passage between the inlet and the thermal actuator and configured to operably measure a first temperature of the sweat thereon; and
    a second thermistor disposed on the flexible structure over the fluid passage between the thermal actuator and the outlet and configured to operably measure a second temperature of the sweat thereon.

2. The sensor of claim 1, wherein the flexible structure comprises:
    a single layer having a first surface on which the thermal actuator and the first and second thermistors are disposed, an opposite, second surface and a body formed therebetween, wherein the fluid passage is defined inside the body and the inlet extents to the second surface.

3. The sensor of claim 1, wherein the flexible structure comprises:
    a fluid passage layer having a first surface from which the fluid passage with the inlet and the outlet is defined, and an opposite, second surface, wherein the inlet extends from the first surface to the second surface; and
    a top layer disposed on the first surface of the fluid passage layer to seal the fluid passage, wherein the thermal actuator and the first and second thermistors are disposed on the top layer.

4. The sensor of claim 1, wherein the flexible structure is formed of a polymer, elastomer, thermoplastics, or silk fibroin.

5. The sensor of claim 4, wherein the polymer comprises poly(dimethylsiloxane) (PDMS), polyurethane, silicone, polyester, or polyethylene.

6. The sensor of claim 1, wherein the fluid passage has a width of about 500 µm to 1 mm, and a height of about 125 µm-300 µm, and a thickness defined from a top of the fluid passage to the bottom of the thermal actuator is about 70 µm-200 µm.

7. The sensor of claim 1, wherein the thermal actuator comprises a plurality of resistors connected in series.

8. The sensor of claim 7, wherein the plurality of resistors comprises eight resistors.

9. The sensor of claim 7, wherein the thermal actuator has a diameter of about 0.5 mm to 2 mm.

10. The sensor of claim 1, wherein the first and second thermistors are respectively located at a distance (L) upstream and downstream from the center of the actuator.

11. The sensor of claim 10, wherein the flow of the sweat transports the heat from the thermal actuator directionally downstream, thereby creating a temperature difference ($\Delta T$) between the first temperature at the location of the first thermistor and the second temperature at the location of the second thermistor.

12. The sensor of claim 11, wherein the temperature difference ($\Delta T$) is related to a flow rate (f) of the sweat.

13. The sensor of claim 1, wherein the sensor is configured to perform continuous, real-time measurements of the flow of the sweat without any direct contact with the sweat.

14. The sensor of claim 1, further comprising an elastomeric encapsulation layer disposed on the thermal actuator and the first and second thermistors and extended over the flexible structure.

15. The sensor of claim 1, wherein the flexible structure further comprises:
    an adhesive flexible layer have a first surface attached to the second surface of the single layer or the fluid passage layer, an opposite, second surface detachably attached to the skin, and an opening through the first and second surface and aligned to the inlet.

16. The sensor of claim 1, further comprising a serpentine microfluid passage in fluidic communication with the inlet to allow for manual readout of rate and volume of sweat as the basis for validating the flow measurements.

17. A system for measuring parameters of sweat from a skin, comprising:
    a wireless platform incorporating the sensor of claim 1 and configured to control current to the thermal actuator, process the measured parameters and transmit the processed parameters to an external device.

18. The system of claim 17, wherein the wireless platform comprises:
    a thermal flow-sensing module (TFM) comprising the thermal actuator; a Wheatstone bridge circuit including the first and second thermistors, a reference thermistor and a known resistor on each bridge; and first and second differential amplifiers (AMPs) respectively coupled to the first and second thermistors; and
    a Bluetooth Low Energy (BLE) system-on-chip (SoC) coupled to the TFM for providing current to the thermal actuator, processing the measured parameters and transmitting the processed parameters to the external device.

19. The system of claim 18, wherein the Wheatstone bridge circuit is configured such that its voltage outputs under different environmental conditions remain around 0 V, thereby imposing no limitation on the amplifier gain or the accuracy of measurements.

20. The system of claim 18, wherein the reference thermistor is located outside the fluid passage but at the same distance from the thermal actuator as the first and second thermistors.

21. The system of claim 18, wherein each AMP amplifies differences between the voltages on the first and second thermistors and a voltage on the reference thermistor to eliminate the effects of temperature differences due to environmental changes.

22. The system of claim 18, wherein the BLE SoC comprises
  a central processing unit (CPU);
  at least three variable gain amplifiers (VGAs) respectively coupled to the first and second AMPs and a reference voltage signal with gain automatically controlled by the CPU;
  at least three analog-to-digital converters (ADCs) respectively coupled to the at least three VGAs and the CPU;
  a general-purpose input/output (GPIO) coupled to the CPU and the thermal actuator for operably providing the current to the thermal actuator; and
  a BLE radio coupled to the CPU for providing two-way communication with the external device.

23. The system of claim 22, wherein each of VGA is configured to amplify the voltage outputs from the Wheatstone bridge circuit, with an adaptive gain to maximize the accuracy of the measurements of resistance within the required dynamic range.

24. The system of claim 23, wherein each of VGA is configured such that as the measured voltage increases and reaches 90% of the upper limit of dynamic range (=supply voltage/gain), the gain decreases, thereby increasing the dynamic range; and as the voltage decreases, the gain increases along with the accuracy.

25. The system of claim 22, wherein the at least three ADCs is configured to monitor the bridge voltages on upstream ($V_{UP}$), downstream ($V_{DN}$), and reference ($V_{REF}$) values and control the gain of the VGAs prior to each ADC to achieve the highest resolution within the input voltage range.

26. The system of claim 25, wherein the CPU operably executes digital signal processing on the ADC-sampled data ($V_{UP}$, $V_{DN}$, and $V_{REF}$) to filter out noise.

27. The system of claim 22, wherein the BLE radio is configured to transmit the processed parameters to the external device, and receive data from the external device to activate a GPIO pin to provide the current to the thermal actuator.

28. The system of claim 27, being adhered to the skin with or without an encapsulated battery mounted mechanically and electrically via matching magnets.

29. The system of claim 17, wherein electronics of the wireless platform are formed on thin, flexible copper-clad polyimide sheets that are processed to yield circuit traces that interconnect the TFM and the BLE SoC.

30. The system of claim 17, further comprising a third thermistor connected in a voltage divider circuit with a known resistor for measuring temperature of the skin.

31. The system of claim 17, wherein the external device is configured for real-time graphical display and storage of the parameters.

32. The system of claim 31, wherein the external device is a computer device, a laptop, a tablet, a smartphone, a smart watch, a smart glass, a wearable device, or a mobile device.

33. The system of claim 31, wherein the external device is configured to analyze the parameters and initiate one or more commands based on the analysis of the parameters to control the heating and/or cooling by turning turn a HVAC system on or off, or adjust a thermostat for the room.

34. The system of claim 31, wherein the external device is configured to analyze the parameters in combination with other data to initiate one or more interventions including a purchase of bottled water or electrolyte-infused sports drinks to initiate a rehydration strategy, initiate order for hydration drinks, and/or initiate change in lighting, temperature, and/or music.

35. A system for measuring parameters of sweat from a skin, the parameters comprise at least one of sweat flow, sweat loss, sweat chemistry and skin temperature, comprising:
  a flexible structure detachably attached to the skin, comprising a microfluidic network comprising a plurality of microscale reservoirs (μ-RVs); and a plurality of inlet ports for collecting sweat as the sweat releases from a surface of the skin, wherein one inlet port of the plurality of inlet ports is configured to collect the sweat for measuring the sweat flow and loss, and each of the remaining inlet ports of the plurality of inlet ports is in fluidic communication with at least one of the plurality of μ-RVs and configured to collect the sweat for measuring the sweat chemistry; and
  a wireless platform operably coupled to the fluid passage of the capper layer for measuring the sweat flow and loss and transmitting the sweat flow and loss to an external device, wherein the wireless platform comprises a thermal flow-sensing module (TFM) comprising:
    a thermal actuator disposed on the flexible structure over the fluid passage of the capper layer and configured to operably provide heat to flow of the sweat through the fluid passage;
    a Wheatstone bridge circuit comprising:
      a first thermistor disposed on the flexible structure over the fluid passage between the inlet and the thermal actuator and configured to operably measure a first temperature of the sweat thereon;
      a second thermistor disposed on the flexible structure over the fluid passage between the thermal actuator and an outlet and configured to operably measure a second temperature of the sweat thereon;
      a reference thermistor; and
      a known resistor on each bridge; and
    first and second differential amplifiers (AM Ps) respectively coupled to the first and second thermistors.

36. The system of claim 35, wherein the Wheatstone bridge circuit is configured such that its voltage outputs under different environmental conditions remain around 0 V, thereby imposing no limitation on the amplifier gain or the accuracy of measurements.

37. The system of claim 35, wherein the reference thermistor is located outside the fluid passage but at the same distance from the thermal actuator as the first and second thermistors.

38. The system of claim 35, wherein each AMP amplifies differences between the voltages on the first and second thermistors and a voltage on the reference thermistor to eliminate the effects of temperature differences due to environmental changes.

39. The system of claim 35, wherein the wireless platform further comprises a Bluetooth Low Energy (BLE) system-on-chip (SoC) coupled to the TFM for providing current to the thermal actuator, processing the measured parameters and transmitting the processed parameters to the external device.

40. The system of claim 39, wherein the BLE SoC comprises:
 a central processing unit (CPU);
 at least three variable gain amplifiers (VGAs) respectively coupled to the first and second AMPs and a reference voltage signal with gain automatically controlled by the CPU;
 at least three analog-to-digital converters (ADCs) respectively coupled to the at least three VGAs and the CPU;
 a general-purpose input/output (G P10) coupled to the CPU and the thermal actuator for operably providing the current to the thermal actuator; and
 a BLE radio coupled to the CPU for providing two-way communication with the external device.

41. The system of claim 40, wherein each of VGA is configured to amplify the voltage outputs from the Wheatstone bridge circuit, with an adaptive gain to maximize the accuracy of the measurements of resistance within the required dynamic range.

42. The system of claim 41, wherein each of VGA is configured such that as the measured voltage increases and reaches 90% of the upper limit of dynamic range (=supply voltage/gain), the gain decreases, thereby increasing the dynamic range; and as the voltage decreases, the gain increases along with the accuracy.

43. The system of claim 40, wherein the at least three ADCs is configured to monitor the bridge voltages on upstream ($V_{UP}$), downstream ($V_{DN}$), and reference ($V_{REF}$) values and control the gain of the VGAs prior to each ADC to achieve the highest resolution within the input voltage range.

44. The e system of claim 43, wherein the CPU operably executes digital signal processing on the ADC-sampled data ($V_{UP}$, $V_{DN}$, and $V_{REF}$) to filter out noise.

45. The system of claim 40, wherein the BLE radio is configured to transmit the processed parameters to the external device, and receive data from the external device to activate a GPIO pin to provide the current to the thermal actuator.

46. A system for measuring parameters of sweat from a skin, the parameters comprise at least one of sweat flow, sweat loss, sweat chemistry and skin temperature, comprising:
 a flexible structure detachably attached to the skin, comprising a microfluidic network comprising a plurality of microscale reservoirs (μ-RVs); and a plurality of inlet ports for collecting sweat as the sweat releases from a surface of the skin, wherein one inlet port of the plurality of inlet ports is configured to collect the sweat for measuring the sweat flow and loss, and each of the remaining inlet ports of the plurality of inlet ports is in fluidic communication with at least one of the plurality of μ-RVs and configured to collect the sweat for measuring the sweat chemistry;
 a thermal actuator disposed on the flexible structure over the fluid passage of a capper layer and configured to operably provide heat to flow of the sweat through the fluid passage;
 a first thermistor disposed on the flexible structure over the fluid passage between the inlet and the thermal actuator and configured to operably measure a first temperature of the sweat thereon;
 a second thermistor disposed on the flexible structure over the fluid passage between the thermal actuator and the outlet and configured to operably measure a second temperature of the sweat thereon; and
 a third thermistor connected in a voltage divider circuit with a known resistor for measuring temperature of the skin.

47. A method for measuring parameters of sweat from a skin, comprising:
 providing a flexible structure detachably attached to the skin, the flexible structure comprising a fluid passage having an inlet and an outlet configured such that sweat enters the inlet as the sweat releases from a surface of the skin and flows through the fluid passage into the outlet;
 heating flow of the sweat through the fluid passage at a location between the inlet and the outlet; and
 measuring a first temperature at a first location of the fluid passage and a second temperature at a second location of the fluid passage, wherein the first location is between the inlet and said location on which the flow of the sweat is heated, the second location is between said location and the outlet, and a distance defined between the first location and said location is identical to that said location and the second location,
 wherein the flow of the sweat transports the heat from said location directionally downstream, thereby creating a temperature difference ($\Delta T$) between the first temperature at the first location and the second temperature at the second location.

48. The method of claim 47, further comprising processing the measured parameters of the first and second temperatures and wirelessly transmitting the processed parameters to an external device.

49. The method of claim 47, wherein the temperature difference ($\Delta T$) is related to a flow rate (f) of the sweat.

50. The method of claim 47, being performed without any direct contact with the sweat.

51. The method of claim 47, wherein the flexible structure further comprises a microfluidic network comprising a plurality of microscale reservoirs (μ-RVs); and a plurality of inlet ports for collecting sweat as the sweat releases from a surface of the skin, wherein one inlet port of the plurality of inlet ports is operably aligned to and in fluidic communication with the inlet of the fluid passage and configured to collect the sweat for measuring the sweat flow and loss, and each of the remaining inlet ports of the plurality of inlet ports is in fluidic communication with at least one of the plurality of μ-RVs and configured to collect the sweat for measuring the sweat chemistry.

52. The method of claim 51, further comprising:
 providing chemical and/or enzymatic assays the plurality of μ-RVs; and
 measuring the sweat chemistry with colorimetric analysis.

53. The method of claim 52, wherein the sweat chemistry comprises at least one of concentrations of chloride, glucose and/or creatinine in the sweat, and pH of the sweat.

54. The method of claim 47, further comprising measuring a temperature of the skin.

* * * * *